(12) United States Patent
Takayuki et al.

(10) Patent No.: US 9,375,329 B2
(45) Date of Patent: *Jun. 28, 2016

(54) STENT AND LIVING ORGAN DILATOR

(71) Applicant: TERUMO KABUSHIKI KAISHA, Shibuya-ku (JP)

(72) Inventors: Kito Takayuki, Kanagawa (JP); Goto Hiroki, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 59 days.

This patent is subject to a terminal disclaimer.

(21) Appl. No.: 14/319,399

(22) Filed: Jun. 30, 2014

(65) Prior Publication Data

US 2014/0316512 A1    Oct. 23, 2014

Related U.S. Application Data

(63) Continuation of application No. 12/732,984, filed as application No. PCT/JP2008/067564 on Sep. 26, 2008, now Pat. No. 8,801,770.

(30) Foreign Application Priority Data

Sep. 27, 2007  (JP) ................................ 2007-252767
Sep. 27, 2007  (JP) ................................ 2007-252768
Sep. 27, 2007  (JP) ................................ 2007-252769

(51) Int. Cl.
*A61F 2/06*    (2013.01)
*A61F 2/86*    (2013.01)
(Continued)

(52) U.S. Cl.
CPC ... *A61F 2/86* (2013.01); *A61F 2/91* (2013.01); *A61F 2/915* (2013.01); *A61L 31/022* (2013.01);
(Continued)

(58) Field of Classification Search
CPC . A61F 2/915; A61F 2/91; A61F 2002/91558; A61F 2002/91525; A61F 2250/0071; A61F 2/88; A61F 2002/9155; A61F 2250/0031; A61F 2002/91583; A61F 2210/0004

USPC ........................................ 623/1.15, 1.16, 1.38
See application file for complete search history.

(56) References Cited

U.S. PATENT DOCUMENTS 5,464,650 A    11/1995  Berg et al.
5,624,411 A    4/1997   Tuch
(Continued)

FOREIGN PATENT DOCUMENTS

JP    8-33718 A    2/1996
JP    9-56807 A    3/1997
(Continued)

OTHER PUBLICATIONS

International Search Report (PCT/ISA/210) mailed on Dec. 22, 2008, by the Patent Office as the International Searching Authority for International Application No. PCT/JP2008/067564.
(Continued)

*Primary Examiner* — Katherine M Shi
(74) *Attorney, Agent, or Firm* — Buchanan Ingersoll & Rooney PC

(57) ABSTRACT

A stent configured to closely contact tissue in vivo by being deformed when set indwelling in vivo. The stent has a plurality of axially arranged annular members, with axially adjacent annular members being interconnected by at least one link part; and a metallic wavy-linear annular member positioned at each end of the stent. The plurality of axially arranged annular members include a plurality of linear components, the linear components including a plurality of metallic linear components and a plurality of biodegradable material-made linear components. The at least one link part is defined by one of the metallic linear components. After a predetermined period of time when the stent is left indwelling in vivo and biodegradation of the biodegradable material-made linear components proceeds, the plurality of metallic linear components and the at least one link part remain intact such that a unitary metallic structure is maintained in vivo.

17 Claims, 46 Drawing Sheets

(51) Int. Cl.
*A61F 2/91* (2013.01)
*A61F 2/915* (2013.01)
*A61L 31/02* (2006.01)
*A61L 31/12* (2006.01)
*A61L 31/14* (2006.01)
*A61M 29/00* (2006.01)
*A61F 2/88* (2006.01)

(52) U.S. Cl.
CPC ............ *A61L 31/128* (2013.01); *A61L 31/148* (2013.01); *A61M 29/00* (2013.01); *A61F 2/88* (2013.01); *A61F 2002/9155* (2013.01); *A61F 2002/91508* (2013.01); *A61F 2002/91525* (2013.01); *A61F 2002/91558* (2013.01); *A61F 2002/91583* (2013.01); *A61F 2220/0075* (2013.01); *A61F 2230/0054* (2013.01); *A61F 2250/0031* (2013.01); *A61F 2250/0071* (2013.01)

(56) References Cited

U.S. PATENT DOCUMENTS

| | | |
|---|---|---|
| 5,679,400 A | 10/1997 | Tuch |
| 5,837,008 A | 11/1998 | Berg et al. |
| 6,231,598 B1 | 5/2001 | Berry et al. |
| 7,108,714 B1 | 9/2006 | Becker |
| 7,618,445 B2 | 11/2009 | Moriuchi et al. |
| 2003/0135265 A1 | 7/2003 | Stinson |
| 2004/0172125 A1 | 9/2004 | Burgermeister |
| 2005/0038501 A1 | 2/2005 | Moore et al. |
| 2005/0165470 A1 | 7/2005 | Weber |
| 2005/0228486 A1 | 10/2005 | Case et al. |
| 2006/0122694 A1 | 6/2006 | Stinson et al. |
| 2007/0219618 A1 | 9/2007 | Cully et al. |
| 2007/0239264 A1 | 10/2007 | Fliedner |
| 2008/0071346 A1 | 3/2008 | Brown |
| 2008/0215129 A1 | 9/2008 | Venturelli et al. |

FOREIGN PATENT DOCUMENTS

| | | |
|---|---|---|
| JP | 2007-144108 A | 6/2007 |
| WO | WO 01/01888 A1 | 1/2001 |
| WO | WO 2006/029617 A1 | 3/2006 |
| WO | WO 2006/060534 A1 | 6/2006 |
| WO | WO 2007/013102 A1 | 2/2007 |

OTHER PUBLICATIONS

Supplemental European Search Report and European Search Opinion dated Nov. 25, 2010, issued by the European Patent Office in corresponding European Patent Application No. 08833752.

Communication Pursuant to Article 94(3) EPC issued on Aug. 8, 2011 by the European Patent Office in corresponding European Patent Application No. 08833752.2.

Japanese Office Action issued May 22, 2012 by Japanese Patent Office in corresponding Japanese Patent Application No. 2007-252769, and English language translation.

Japanese Office Action issued Oct. 16, 2012 by the Japanese Patent Office in Japanese Patent Application No. 2007-252769 and English translation.

STENT AND LIVING ORGAN DILATOR

This application is a continuation of U.S. application Ser. No. 12/732,984 filed on Mar. 26, 2010, which is a continuation of International Application No. PCT/JP2008/067564 filed on Sep. 26, 2008, and claims priority to Japanese Application No. 2007-252769 filed on Sep. 27, 2007, Japanese Application No. 2007-252767 filed on Sep. 27, 2007 and Japanese Application No. 2007-252768 filed on Sep. 27, 2007, the entire content of all of which is incorporated herein by reference.

TECHNICAL FIELD

The disclosure here generally relates to an in-vivo indwelling stent and a living organ dilator which are used for improvement of a stenosed lesion or occluded lesion generated in a lumen in vivo such as blood vessel, bile duct, trachea, esophagus, urethra, etc.

BACKGROUND DISCUSSION

Stents are generally tubular medical devices which, for curing of various diseases generated by stenosis or occlusion of a blood vessel or other lumen in vivo, are left indwelling in the stenosed or occluded lesion so as to dilate the lesion and secure the lumen.

The stent is so configured that for insertion into a body from outside, the stent is small in diameter when inserted, is thereafter expanded to be greater in diameter in the target stenosed or occluded lesion, and holds the lumen as it is.

Stents, in general, are hollow cylindrical bodies formed by processing metallic wire or metallic pipe. The stent is mounted to a catheter or the like in the state of being reduced in diametral size, is inserted in vivo, and is expanded in a target lesion by some method to come into close contact with and be fixed on the inner wall of a lumen, thereby maintaining the lumen shape. Stents are classified into self-expandable stents and balloon-expandable stents, according to function and method of indwelling. A balloon-expandable stent is a stent which itself does not have an expanding function. Instead, after the stent is inserted into a target lesion, a balloon is located in the stent, and the balloon is dilated so that the stent is expanded (plastically deformed) by the expanding (dilating) force of the balloon to come into close contact with and be fixed on the inner surface of the target lumen. This type of stent needs the just-mentioned stent-expanding work.

The purpose of indwelling of a stent is for preventing and restraining restenosis which might otherwise occur after such a procedure as PTCA is conducted. In recent years, use has come to be made of stents on which a physiologically active substance is carried and the physiologically active substance is locally released for a long period of time at the indwelling lesion in a lumen, for the purpose of lowering the restenosis rate. For instance, Japanese Patent Laid-Open No. Hei 8-33718 (EPC Publication No. EP0623354) discloses a stent in which a coating of a mixture of a therapeutic substance and a polymer is provided on a surface of a stent body. Besides, Japanese Patent Laid-open No. Hei 9-56807 proposes a stent in which a medicine layer is provided on a surface of a stent body and, further, a biodegradable polymer layer is provided on the surface of the medicine layer.

In addition, JP-T-2003-503152 (PCT Patent Publication No. WO01/001888) discloses a combined body of a plurality of stent pieces which are matched to one another, are aligned in a substantially annular shape and, further, are self-expanded in the radial direction. In this stent, the adjacent stent pieces are interlinked (coupled) to each other by at least one interlinking element formed from a plastically deformable material so that a flexible and limited motion is realized between the adjacent stent pieces. Besides, it is also disclosed that the interlinking element is formed from a degradable (decomposable) material.

Intensive and extensive investigations by the inventors here has led to the discovery that the blood vessel dilation maintaining force (strength) possessed by a stent may be one of the causes of restenosis. A stent having a lower blood vessel dilation maintaining force, however, cannot offer a sufficient improvement of the stenosed lesion of a blood vessel when left indwelling.

SUMMARY

The stent disclosed here, when left indwelling, has a sufficient blood vessel dilation maintaining force and can favorably improve a stenosed lesion, and which, after a predetermined period of time, becomes flexible and exhibits a high follow-up property to deformations of the blood vessel, and a living organ dilator including the stent.

The stent also exhibits a dilating force with sufficient uniformity over its whole body, and which, upon generation of restenosis after the stent is left indwelling, enables a curing activity such as re-dilation in the indwelling lesion of the stent, and a living organ dilator including the stent.

The stent disclosed here includes linear components and coming into close contact with a tissue in vivo through being deformed when set indwelling in vivo, wherein the stent has linear components which are deformed to exhibit a force for maintaining dilation when the stent is set indwelling in vivo, the linear components deformed when the stent is set indwelling in vivo are included of non-biodegradable metallic linear components and a plurality of biodegradable material-made linear components which are bonded to the non-biodegradable metallic linear components, the stent, when left indwelling in vivo, exhibits the force for maintaining the dilation owing to both the non-biodegradable metallic linear components and the biodegradable material-made linear components, and, after a predetermined period of time, biodegradation of the biodegradable material-made linear components proceeds, whereby the force for maintaining the dilation is lowered.

DETAILED DESCRIPTION

An in-vivo indwelling stent in accordance with the disclosure here is described below with reference to the following preferred embodiments.

The stent disclosed here is a stent composed of linear components and which, when set indwelling in vivo, is deformed to come into close contact with a tissue in vivo. The stent 1 has linear components which are deformed when the stent 1 is set indwelling in vivo and exhibits a force for maintaining dilation. The linear components deformed when the stent is set indwelling in vivo are composed of a plurality of non-biodegradable metallic linear components 21, 22, 23 and 24 and a plurality of biodegradable material-made linear components 3 which are bonded to the non-biodegradable metallic linear components 21, 22, 23 and 24. Furthermore, the stent 1, when left indwelling in vivo, exhibits the force for maintaining the dilation owing to both the non-biodegradable metallic linear components 21, 22, 23 and 24 and the biodegradable material-made linear components 3. After a predetermined period of time, biodegradation of the biodegradable material-made linear components 3 proceeds, whereby the force for maintaining the dilation is lowered.

The in-vivo indwelling stent 1 according to this embodiment is composed of metallic stent base body 2 formed in a substantially tubular shape from the non-biodegradable metallic linear components 21, 22, 23 and 24, and a plurality of the biodegradable material-made linear components 3 each of which is joined to the metallic linear components at one end and the other end thereof. The metallic stent base body 2 formed from the non-biodegradable metallic linear components 21, 22, 23 and 24 and the plurality of biodegradable material-made linear components 3 each joined to the metallic linear components at one end and the other end thereof are deformed, when the stent is set indwelling in vivo, to exhibit a force for maintaining dilation.

The stent 1 in this embodiment is a self-expandable stent which is compressed in the direction of the center axis of the stent at the time of being inserted in vivo, and which, when left indwelling in vivo, is expanded outwards to restore or return to its pre-compression shape. The stent disclosed here is not limited to the self-expandable stent, but may be a so-called balloon-expandable stent, namely, a stent which is formed in a substantially tubular shape, which has a diameter suitable for insertion into a lumen in vivo, and which can be expanded when an outwardly directed force dilating the stent radial outward direction from the inside of the tubular body is exerted on the stent.

Figure 1:
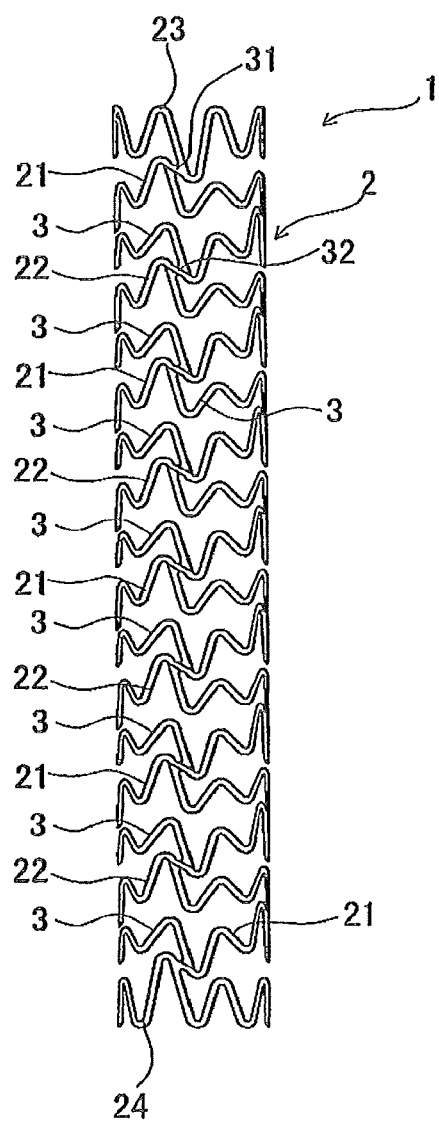
FIG. 1 is a front view of a stent according to an embodiment disclosed here.
Figure 2:
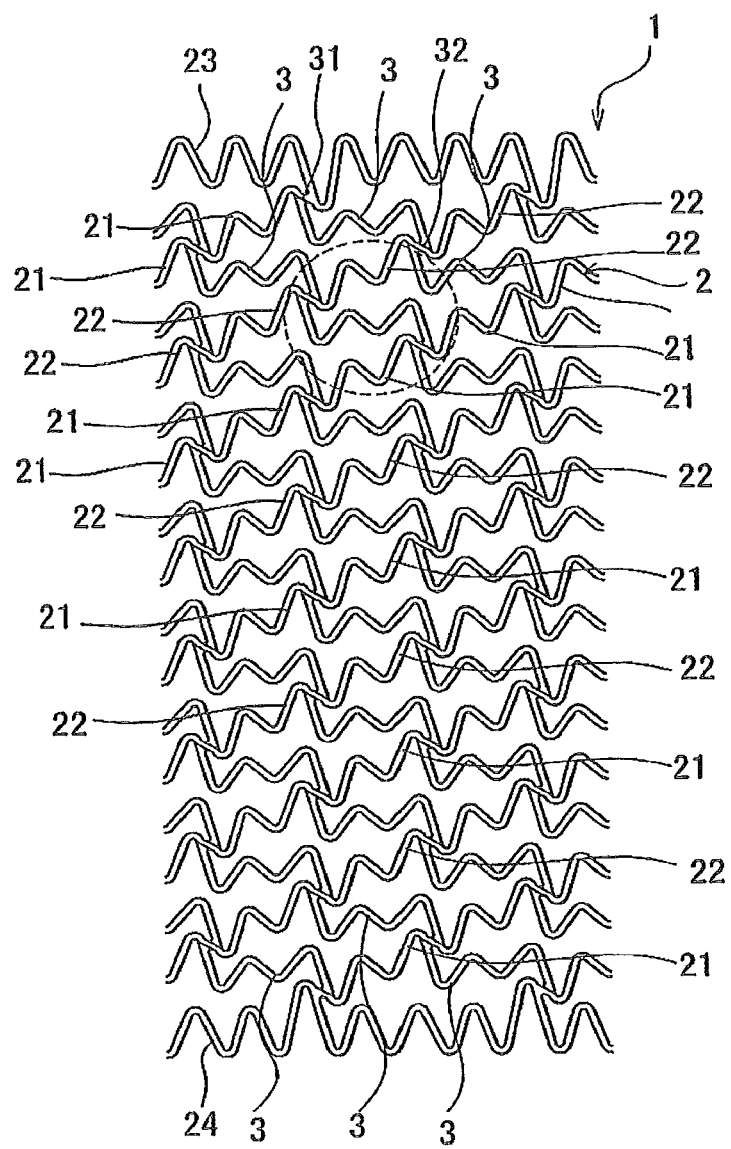
FIG. 2 is a developmental view of the stent shown in FIG. 1 illustrating the stent cut along its longitudinal extent and flattened out.
Figure 3:
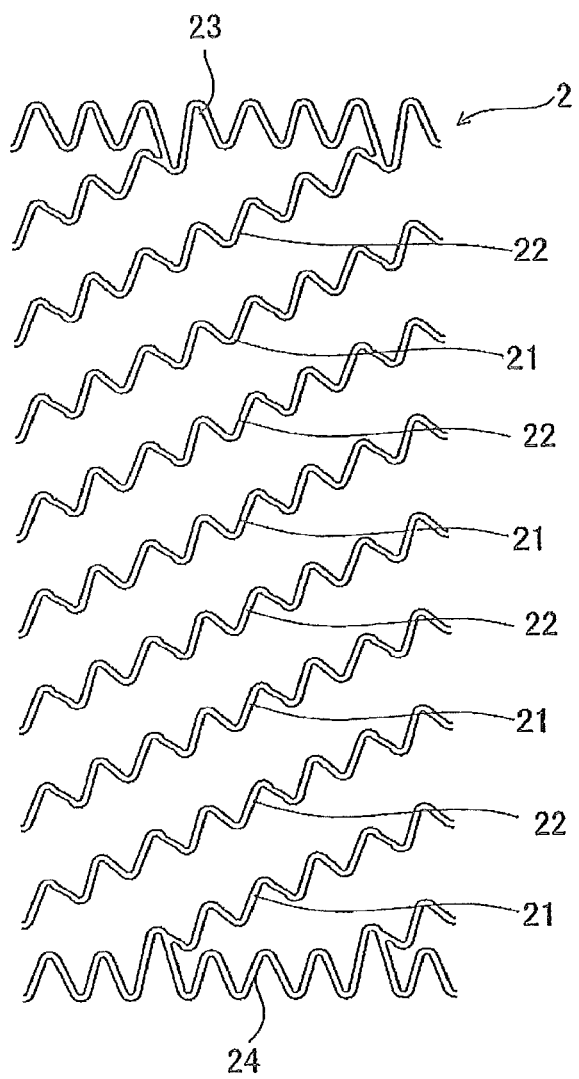
FIG. 3 is an explanatory drawing illustrating operation of the stent of FIG. 1.

As shown in FIGS. 1 to 3, the stent 1 in this embodiment is composed of the metallic stent base body 2 formed in a substantially tubular shape from the non-biodegradable metallic linear components 21, 22, 23 and 24, and the plurality of biodegradable material-made linear components 3 each of which is joined to the metallic linear components at one end and the other end thereof. FIG. 3 shows a condition where the biodegradable material-made linear components 3 have disappeared from the stent of FIG. 1, in other words, a condition where only the non-biodegradable metallic stent base body 2 is present. In this stent 1, after a predetermined period of time, the biodegradation of the biodegradable material-made linear components 3 proceeds, whereby the force for maintaining the dilation is lowered gradually.

In addition, in the disclosed stent, a basic skeleton portion of the stent is composed of the non-biodegradable metallic linear components so that the stent maintains the stent shape even after disappearance of the biodegradable material-made linear components. In the stent 1 according to this embodiment, due to the disappearance of the biodegradable material-made linear components, about half of all the linear components disappear. Although the stent shape is maintained, as shown in FIG. 3, the distance between the linear components is enlarged, in other words, the gaps in the side surface of the stent are considerably increased, resulting in a lowering of the force for maintaining the dilation and an enhancement of flexibility.

The metallic stent base body 2 comprises a plurality of linear spiral members 21 and 22 which are each composed of a zigzag metallic linear component and formed in a spiral shape in relation to the axial direction of the stent. The biodegradable material-made linear components 3 interconnect the plurality of linear spiral members, and are zigzag in shape. In the stent 1 in this embodiment, the zigzag shape of the biodegradable material-made linear components extends in a direction different from the spiral direction of the metallic linear components. In this stent 1, the metallic stent base body 2 also comprises metallic wavy-linear annular parts 23 and 24 formed in an endless (looped) shape, at portions located at both ends of the metallic stent base body. With the metallic wavy-linear annular parts 23 and 24 thus provided at both end portions of the metallic stent base body, relatively strong forces for maintaining the dilation of a blood vessel exist at both end portions of the stent.

The metallic stent base body 2 of the stent 1 in this embodiment is formed by partially eliminating material from a metallic pipe, wherein the plurality of (specifically, two) linear spiral members 21, 22 being zigzag and spiral in shape are arranged substantially in parallel to each other, as shown in FIGS. 1 to 3 (particularly, FIG. 3). The individual linear spiral members 21 and 22 can securely grow larger in diameter at the time of restoration after compression due to its zigzag structure, and are relatively highly deformable at a curved stenosed lesion due to its spiral shape.

As shown in FIG. 3, the metallic stent base body 2 in this embodiment composes: the two linear spiral members 21 and 22 arranged in parallel; a one-end-side metallic wavy-linear annular part 23 which is located on one end side of the metallic stent base body and to which one-side ends of the two linear spiral members 21 and 22 are linked; and an other-end-side metallic wavy-linear annular part 24 which is located on the other end side of the metallic stent base body and to which the other-side ends of the two linear spiral members 21 and 22 are linked. In addition, at the metallic wavy-linear annular parts 23 and 24, the height (depth) of valley and peak portions is greater at the parts of linking to the linear spiral members 21 and 22 than at the other parts. In the stent disclosed here, the number of linear spiral members may be three or more.

The distance between valley and peak portions of each linear spiral member (in other words, the distance between vertices of the zigzag shape of each linear spiral member) is preferably 2.0 to 8.0 mm. In addition, the angle (internal angle) of the linear spiral members in relation to the axial direction of the stent is preferably 30 to 70°. In a single one of the linear spiral members, the distance and the angle may be all the same or may be partially different.

For instance, the above-described distance in the linear spiral member at parts located at a central portion of the stent 1 may be shorter than the above-described distance in the linear spiral member at parts located at both end portions of the stent 1.

Further, in the stent 1 according to this embodiment, as a whole, the plurality of linear spiral members are substantially equally spaced from one another. In other words, in the stent 1 as a whole, all the linear spiral members are the same in spiral pitch. However, this configuration is non-limitative, and the spiral pitch may differ partially. For instance, the spiral pitch at parts located at a central portion of the stent 1 may be shorter than the spiral pitch at parts located at both end portions of the stent 1. This configuration helps ensure that, of the stent 1, the central portion is higher than both end portions in expanding (dilating) force.

In the case of this embodiment pertaining to the self-expandable stent, the material forming the metallic stent base body 2 is preferably a superelastic metal. As the superelastic metal, a superelastic alloy is preferably used. The superelastic alloy here means an alloy which is generally called shape memory alloy and which exhibits superelasticity at least at a living body temperature (around 37° C.). Particularly preferable examples of the superelastic metal include Ti—Ni alloys containing 49 to 53 at % of Ni, Cu—Zn alloys containing 38.5 to 41.5 wt % of Zn, Cu—Zn—X alloys (X=Be, Si, Sn, Al, or Ga) containing 1 to 10 wt % of X, and Ni—Al alloys containing 36 to 38 at % of Al. Among these, especially preferred are the Ti—Ni alloys. In addition, mechanical properties of the material can be varied, as required, by setting the superelastic metal to be a Ti—Ni—X alloy (X=Co, Fe, Mn, Cr, V, Al, Nb, W, B or the like) obtained by replacing a part of the Ti—Ni alloy with 0.01 to 10.0% of X, or by setting the superelastic metal to be a Ti—Ni—X alloy (X=Cu, Pb, or Zr) obtained by replacing a part of the Ti—Ni alloy with 0.01 to 30.0% of atoms, or by selecting the cold working rate or/and final heat treatment conditions. The buckling strength (yield stress when loaded) of the superelastic alloy to be used is 5 to 200 kg/mm$^2$ (at 22° C.), preferably 8 to 150 kg/mm$^2$, and the restoring stress (yield stress when unloaded) of the superelastic alloy is 3 to 180 kg/mm$^2$ (at 22° C.), preferably 5 to 130 kg/mm$^2$. The superelasticity here means that even when the material is deformed (bent, stretched, or compressed) into a region where ordinary metals are plastically deformed, at a use temperature, the deformed material will, after release of the deformation, substantially restore its shape before the compression without need for heating.

In addition, in the stent 1, the biodegradable material-made linear components 3 interconnect the plurality of metallic linear spiral members 21 and 22, and are zigzag in shape. The zigzag shape of the biodegradable material-made linear components 3 extends in a direction different from the spiral direction of the metallic linear spiral members. Specifically, the metallic linear spiral members 21 and 22 are interconnected by the biodegradable material-made linear components 3 which are set at substantially equal intervals, are relatively shorter, are zigzag in shape and extend in a direction different from the spiral direction of the metallic linear spiral members. In addition, the plurality of zigzag biodegradable material-made linear components 3 are disposed at positions which also are arrayed in a spiral extending in the axial direction. The number of vertices of the zigzag biodegradable material-made linear component 3 is preferably about 3 to 8.

The biodegradable material used for forming the biodegradable material-made linear components is preferably a biodegradable metal or a biodegradable polymer. The biodegradable material is preferably one that imparts adhesiveness to the stent-forming material.

Examples of the biodegradable metal used here include pure magnesium, magnesium alloys, calcium, zinc, and lithium. Among these biodegradable metals, preferred are pure magnesium and magnesium alloys. The magnesium alloys here are preferably those which contain magnesium as a main constituent and contain at least one element selected from a biocompatible element group consisting of Zr, Y, Ti, Ta, Nd, Nb, Zn, Ca, Al, Li, and Mn.

Examples of the magnesium alloy include those which contain 50 to 98% of magnesium, 0 to 40% of lithium (Li), 0 to 5% of iron, and 0 to 5% of other metal(s) or rare earth element(s) (cerium, lanthanum, neodymium, praseodymium, or the like). The examples of the magnesium alloy also include those which contain 79 to 97% of magnesium, 2 to 5% of aluminum, 0 to 12% of lithium (Li), and 1 to 4% of rare earth element(s) (cerium, lanthanum, neodymium, praseodymium, or the like). The examples of the magnesium alloy further include those which contain 85 to 91% of magnesium, 2% of aluminum, 6 to 12% of lithium (Li), and 1% of rare earth element(s) (cerium, lanthanum, neodymium, praseodymium, or the like). The examples of the magnesium alloy further include those which contain 86 to 97% of magnesium, 2 to 4% of aluminum, 0 to 8% of lithium (Li), and 1 to 2% of rare earth element(s) (cerium, lanthanum, neodymium, praseodymium, or the like). The examples of the magnesium alloy also include those which contain 8.5 to 9.5% of aluminum, 0.15 to 0.4% of manganese (Mn), and 0.45 to 0.9% of zinc, the balance being magnesium. The examples of the magnesium alloy further include those which contain 4.5 to 5.3% of aluminum, and 0.28 to 0.5% of manganese (Mn), the balance being magnesium. The examples of the magnesium alloy also include those which contain 55 to 65% of magnesium, 30 to 40% of lithium (Li), and 0 to 5% of other metal(s) and/or rare earth element(s) (cerium, lanthanum, neodymium, praseodymium, or the like).

In addition, the biodegradable polymer is not particularly limited, insofar as the polymer is enzymatically or non-enzymatically degraded (decomposed) in vivo and the degradation (decomposition) product does not show toxicity. Examples of the biodegradable polymer which can be used here include polylactic acid, polyglycolic acid, polylactic acid-polyglycolic acid copolymer, polycaprolactone, polylactic acid-polycaprolactone copolymer, polyorthoesters, polyphosphazene, polyphosphate esters, polyhydroxybutyric acid, polymalic acid, poly-α-amino acid, collagen, gelatin, laminin, heparin sulfate, fibronectin, vitronectin, condroitin sulfate, hyaluronic acid, polypeptides, chitin, and chitosan.

Besides, those portions of the non-biodegradable metallic linear spiral members which are joined to the biodegradable material-made linear components may be wholly or partly surface treated, for enhancing the adhesion to the material forming the biodegradable material-made linear components. The surface treatment is preferably carried out by a method in which the relevant surface is coated with a high-affinity material serving as a primer. As the primer material, various materials can be used, of which the most preferable are silane coupling agents having a hydrolyzable group and an organic functional group. Silanol group produced by the degradation of the hydrolyzable group (e.g., alkoxyl group) of the silane coupling agent is linked to the surface of the joint part (free end portion) of the easily deformable metallic portion by covalent bond or the like. The organic functional group (e.g., epoxyl group, amino group, mercapto group, vinyl group, or methacryloxyl group) can be linked to a polymer in a resin-made adhesive layer by chemical bond. Specific examples of the silane coupling agents include γ-aminopropylethoxysilane, and γ-glycidoxypropylmethyldimethoxysilane. Examples of other primer materials than the silane coupling agents include organic titanium coupling agents, aluminum coupling agents, chromium coupling agents, organic phosphoric acid coupling agents, organic evaporated films of polyparaxylene or the like, cyanoacrylate adhesives, and polyurethane paste resins.

In addition, a physiologically active substance may be contained in the material forming the biodegradable material-made linear components. Examples of the physiologically active substance include medicine for suppressing hypertrophy of inner membrane, carcinostatic agent, immunosuppressor, antibiotic, antirheumatic, antithrombotic agent, HMG-CoA reductase inhibitor, ACE inhibitor, calcium antagonist, antilipemia agent, anti-inflammatory agent, integrin inhibitor, antiallergic agent, antioxidant, GPIIbIIIa antagonist, retinoid, flavonoid and carotenoid, lipid improver, DNA synthesis inhibitor, tyrosine kinase inhibitor, antiplatelet agent, vascular smooth muscle growth suppressor, bio-derived material, interferon, and epitheliocytes produced by gene engineering. Mixtures of two or more of the above-mentioned medicines and the like may also be used. Preferable examples of the carcinostatic agent include vincristine, vinblastine, vindesine, irinotecan, pirarubicin, paclitaxel, docetaxel, methotrexate and the like. Preferable examples of the immunosuppressor include sirolimus, tacrolimus, azathioprine, siclosporin, cyclophosphamide, mycophenolate mofetil, gusperimus, mizoribin and the like. Preferable examples of the antibiotic include mitomycin, adriamycin, doxorubicin, actinomycin, daunorubicin, idarubicin, pirarubicin, aclarubicin, epirubicin, pepromycin, zinostatin stimalamer and the like. Preferable examples of the antirheumatic include methotrexate, sodium thiomaleate, penicillamine, lobenzarit and the like. Preferable examples of the antithrombic agent include heparin, aspirin, antithrombin preparation, ticlopidine, hirudin and the like. Preferable examples of the HMG-CoA reductase inhibitor include cerivastatin, cerivastatin sodium, atorvastatin, nisvastatin, itavastatin, fluvastatin, fluvastatin sodium, simvastatin, lovastatin, pravastatin and the like. Preferable examples of the ACE inhibitor include quinapril, perindopril erbumine, trandolapril, cilazapril, temocapril, delapril, enalapril maleate, lisinopril, captopril and the like. Preferable examples of the calcium antagonist include nifedipine, nilvadipine, diltiazem, benidipine, nisoldipine and the like. Preferable examples of the antilipemia agent include probucol. Preferable examples of the antiallergic agent include tranilast. Preferable examples of the retinoid include all-trans-retinoic acid. Preferable examples of the flavonoid and carotenoid include catechins, particularly, epigallocatechin gallate, anthocyanine, proantocyanidin, lycopene, β-carotene and the like. Preferable examples of the tyrosine kinase inhibitor include genistein, tyrphostin, erbstatin and the like. Preferable examples of the anti-inflammatory agent include steroids such as dexamethasone and prednisolone. Preferable examples of the bio-derived material include EGF (epidermal growth factor), VEGF (vascular endothelial growth factor), HGF (hepatocyte growth factor), PDGF (platelet derived growth factor), bFGF (basic fibroblast growth factor) and the like.

Figure 4:
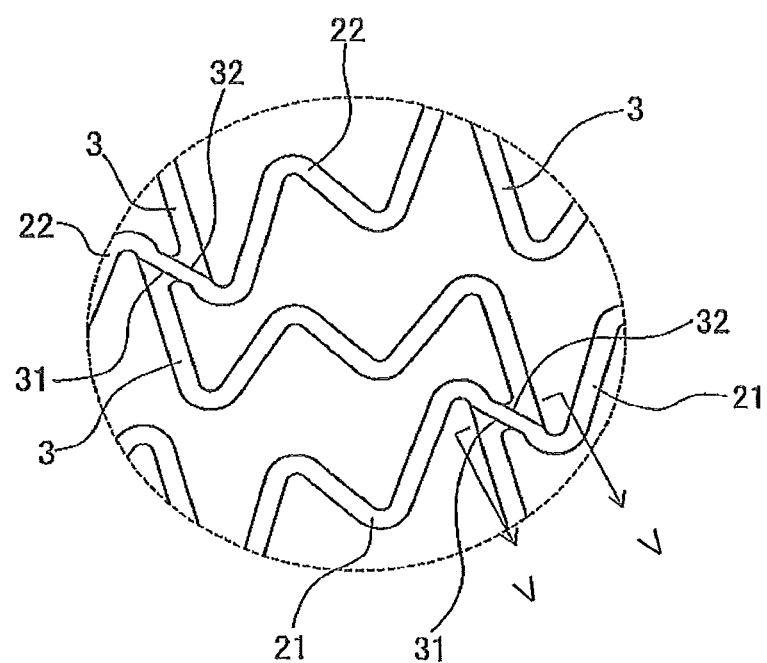
FIG. 4 is an enlarged view of the circled portion of the stent shown in FIG. 2.
Figure 5:
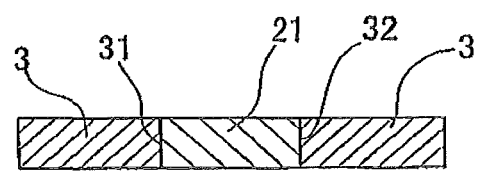
FIG. 5 is an enlarged cross-sectional view taken along the section line V-V in FIG. 4.

In the stent 1 in this embodiment, as shown in FIGS. 4 and 5, the biodegradable material-made linear components 3 are each joined to the metallic linear spiral members 21 and 22 at side portions of the metallic linear spiral members 21 and 22. Specifically, as shown in FIG. 4, a distal end portion, directed toward one end of the stent, of one biodegradable material-made linear component 3 is joined to a side portion 31 of a rectilinear line of one of the metallic linear spiral members 21 and 22. The biodegradable material-made linear component 3 extends in a zigzag fashion over a predetermined distance in the circumferential direction of the stent, to reach the other (axially adjacent) of the metallic linear spiral members 21 and 22. In addition, a proximal end portion, directed toward the other end of the stent, of another biodegradable material-made linear component 3 is joined to a side portion 32 of a rectilinear line of the other of the metallic linear spiral members 21 and 22. While a so-called end face joining is adopted in this stent, the joining form is not limited in this regard, and may be one as shown in FIGS. 6 and 7.

Figure 6:
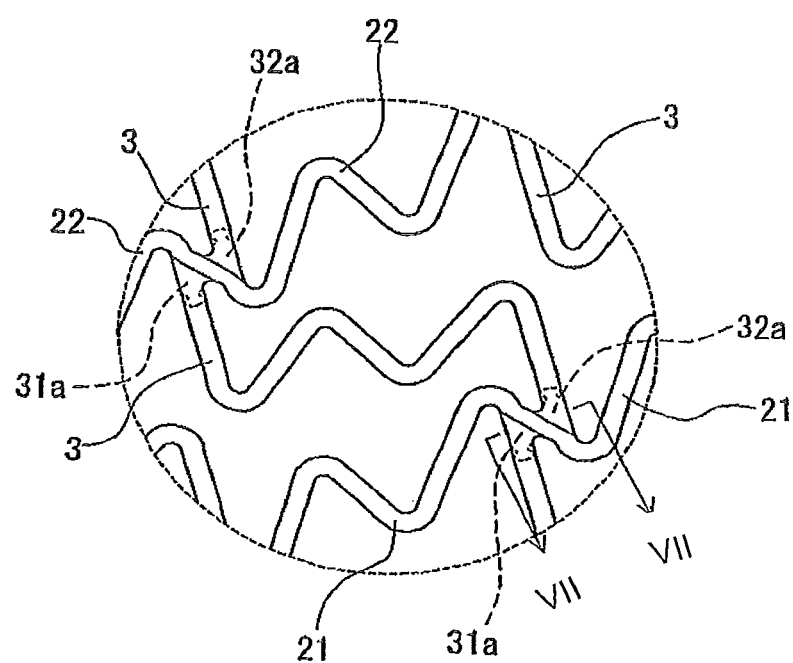
FIG. 6 is an enlarged view of a portion of a stent according to another embodiment.
Figure 7:
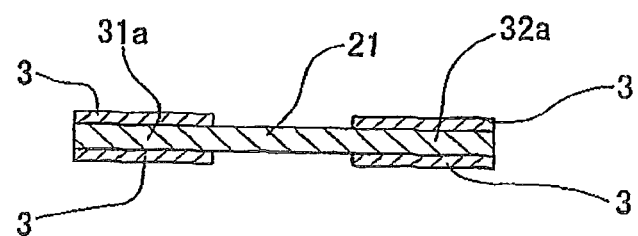
FIG. 7 is an enlarged cross-sectional view taken along the section line VII-VII in FIG. 6.

In the embodiment of the stent shown in FIGS. 6 and 7, the metallic linear spiral members 21 and 22 have joint parts 31a and 32a which partly protrude from the zigzag shape. In addition, one end of the biodegradable material-made linear component 3 is joined to the joint part 31a, and the other end of the biodegradable material-made linear component 3 is joined to the joint part 32a. Besides, in the stent in this embodiment, as shown in FIG. 6, the free ends of the joint parts 31a and 32a have corner portions rounded. In addition, in the stent in this embodiment, as shown in FIG. 6, end portions of the biodegradable material-made linear components 3 envelope only the free end portions of the joint parts 31a and 32a, and the zigzag portions of the metallic linear spiral members 21 and 22 have their surfaces exposed.

Figure 8:
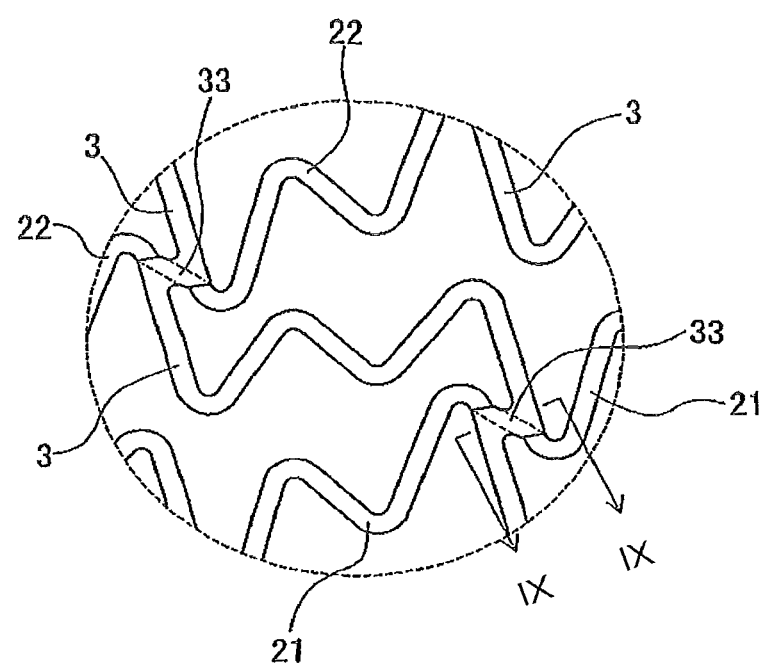
FIG. 8 is an enlarged view of a portion of a stent according to another embodiment.
Figure 9:
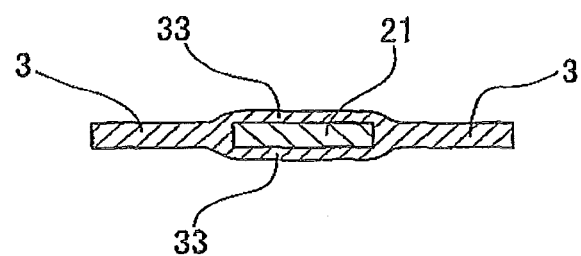
FIG. 9 is an enlarged cross-sectional view taken along the section line IX-IX in FIG. 8.

The form of the linking portion (i.e., the portion linking the biodegradable material-made linear components to the metallic linear spiral members 21 and 22) is not limited to the above-mentioned one, and may be one shown in FIGS. 8 and 9.

In the embodiment of the stent shown in FIGS. 8 and 9, the biodegradable material-made linear components 3 cover the outer and inner surfaces of the metallic linear spiral members 21 and 22 at joint parts 33. This helps ensure that the outer and inner surfaces of the stent are gently curved surfaces free of stepped portions. The biodegradable material-made linear component 3 need not cover both surfaces of the metallic linear spiral member, and may cover only one of the outer and inner surfaces of the metallic linear spiral member.

In all the above-described embodiments, those portions of the metallic linear spiral components which are joined to the biodegradable material-made linear components may be wholly or partly surface treated, for enhancing adhesion thereof to the material forming the biodegradable material-made linear components. The surface treatment is preferably carried out by a method wherein the relevant surface is coated with a high-affinity material serving as a primer. As the surface treatment method, the above-mentioned ones can be used suitably.

Figure 10:
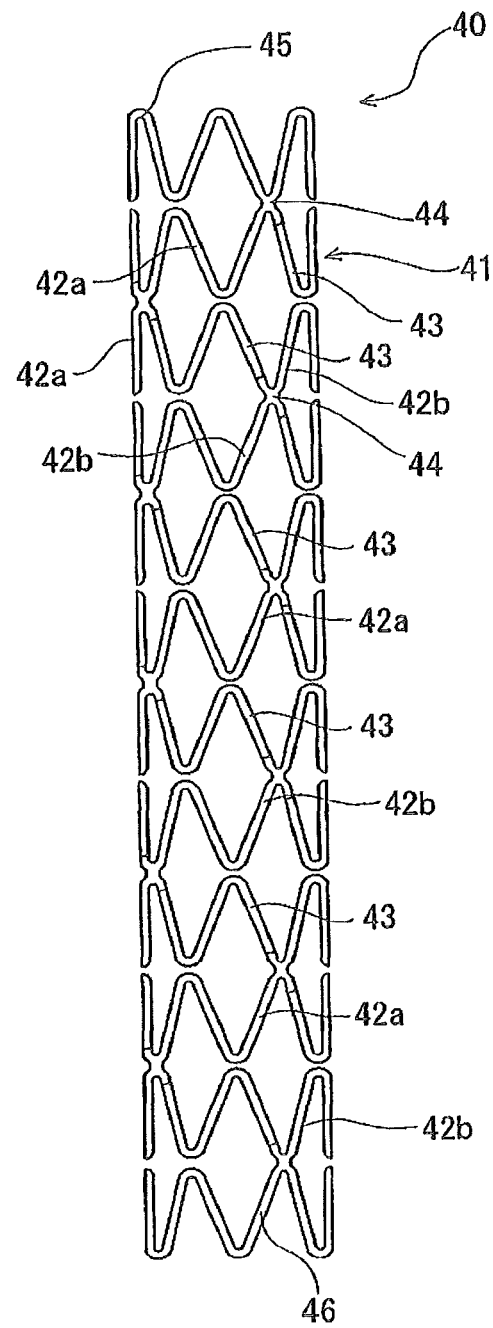
FIG. 10 is a front view of a stent according to yet another embodiment.
Figure 11:
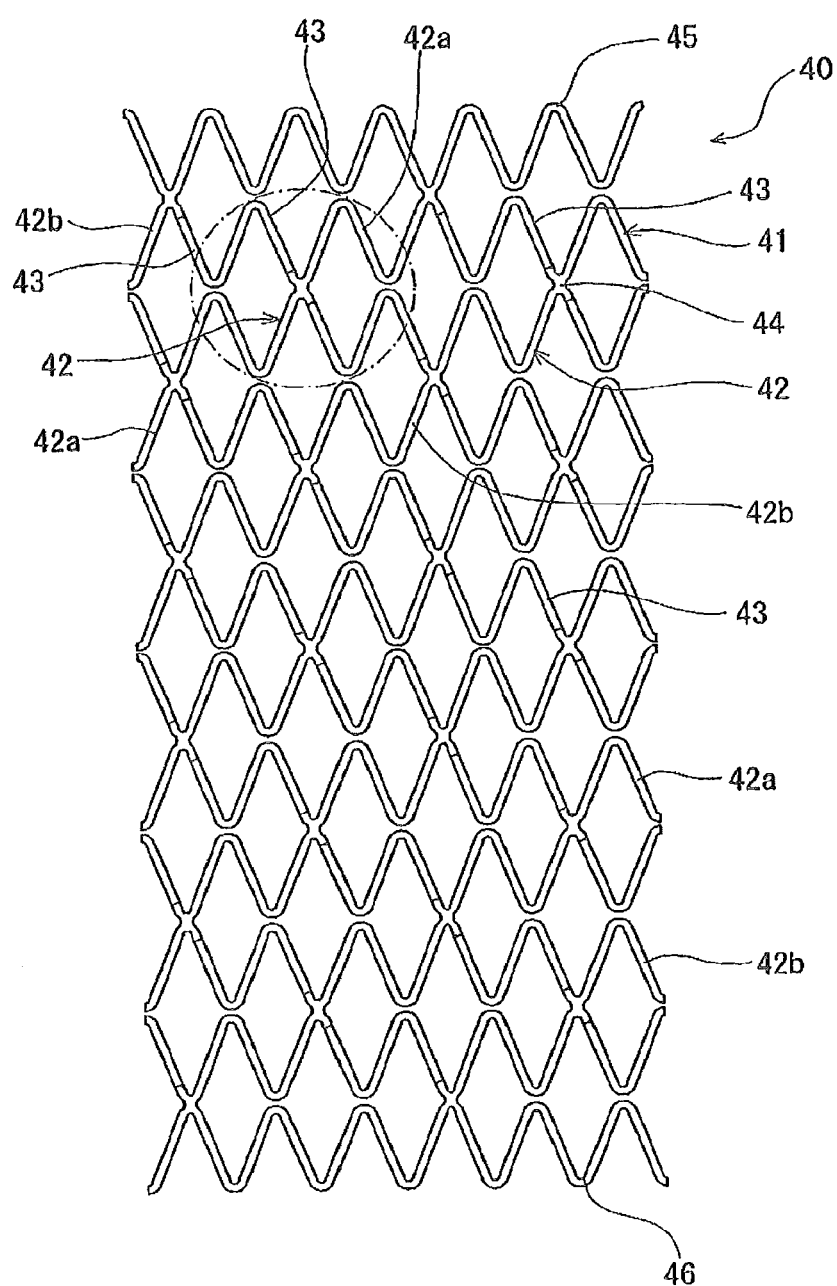
FIG. 11 is a developmental view of the stent shown in FIG. 10.
Figure 12:
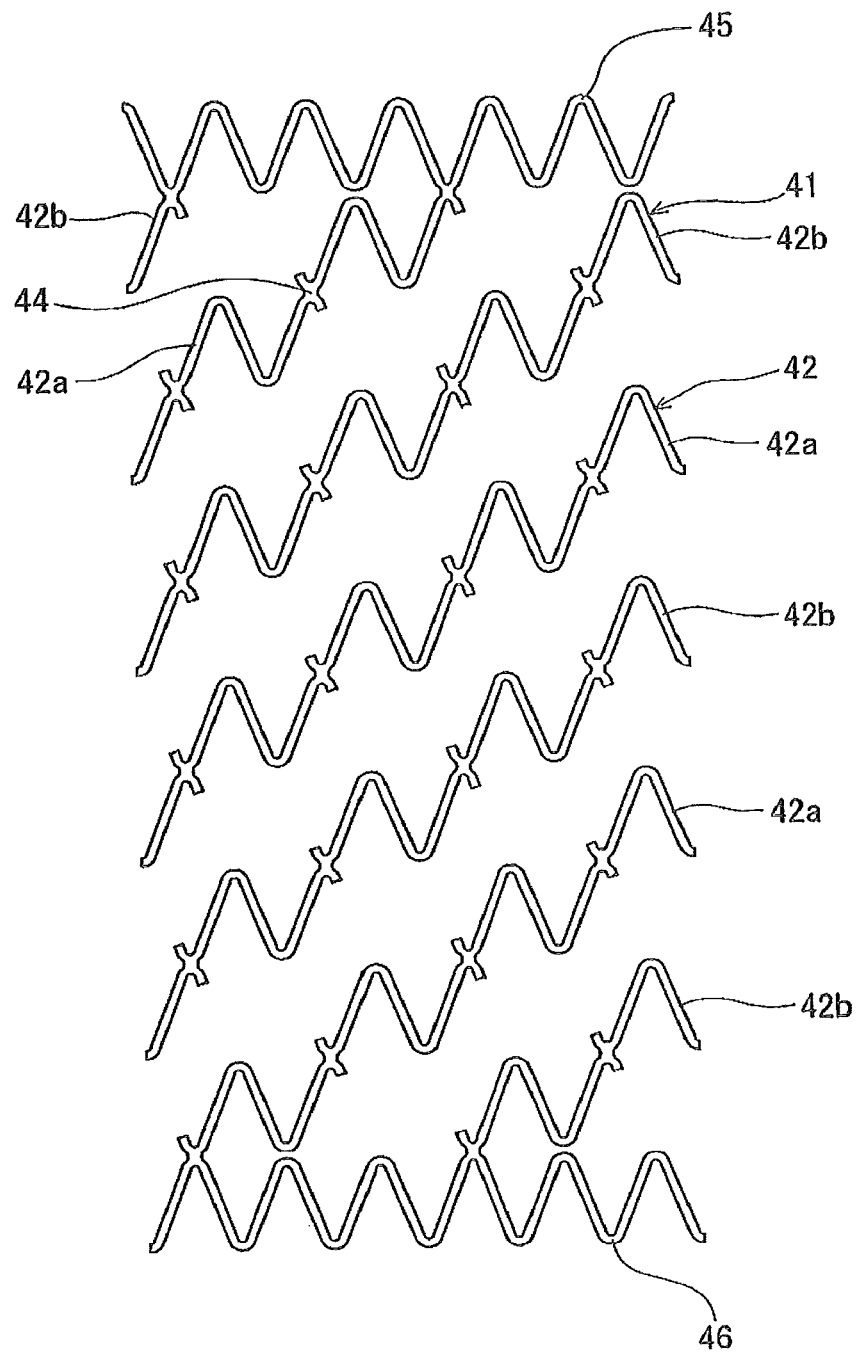
FIG. 12 is an explanatory drawing illustrating operation of the stent of FIG. 10.

FIGS. 10-13 illustrate an alternative embodiment of the stent. FIG. 12 shows a condition where biodegradable material-made linear components 43 have disappeared from the stent of FIG. 10, in other words a condition where only a metallic stent base body 41 is present. In this stent, therefore, a basic skeleton portion of the stent is composed of metallic linear components so that the stent shape is maintained even after the disappearance (biodegradation) of the biodegradable material-made linear components.

The stent 40 in this embodiment has a configuration in which a plurality of annular members formed in an annular shape from linear components are arrayed in the axial direction, the adjacent annular members being interconnected by link parts 44. The annular members 45 and 46 located respectively at both ends of the stent are metallic wavy-linear annular members, and the link parts 44 are composed of the metallic linear components.

In addition, in the stent 40 according to this embodiment, the annular members 45 and 46 located at both ends of the stent are metallic wavy-linear annular members, but the other annular members compose both the metallic linear components 42a and 42b and the biodegradable material-made linear components 43. As mentioned, FIG. 12 shows a condition where the biodegradable material-made linear components 43 have disappeared from the stent shown in FIG. 10, in other words, a condition where only the metallic stent base body 41 is present. As shown in FIG. 12, this stent 40 composes two metallic linear spiral members 42a and 42b, in the same manner as the above-described stent 1. The metallic linear spiral members 42a and 42b are interconnected by the biodegradable material-made linear components 43 which are arranged at substantially equal intervals, are relatively shorter, are in a zigzag shape and extend in the circumferential direction of the stent. The plurality of zigzag biodegradable material-made linear components 43 are disposed at positions which are arranged in a spiral pattern extending in the axial direction of the stent. In the stent according to this embodiment, the manner or form by which the metallic linear spiral members 42a and 42b are joined with the biodegradable material-made linear components 43 may be any of the above-mentioned joining forms. Also, a joining form as shown in FIGS. 13 and 14 may be used.

Figure 13:
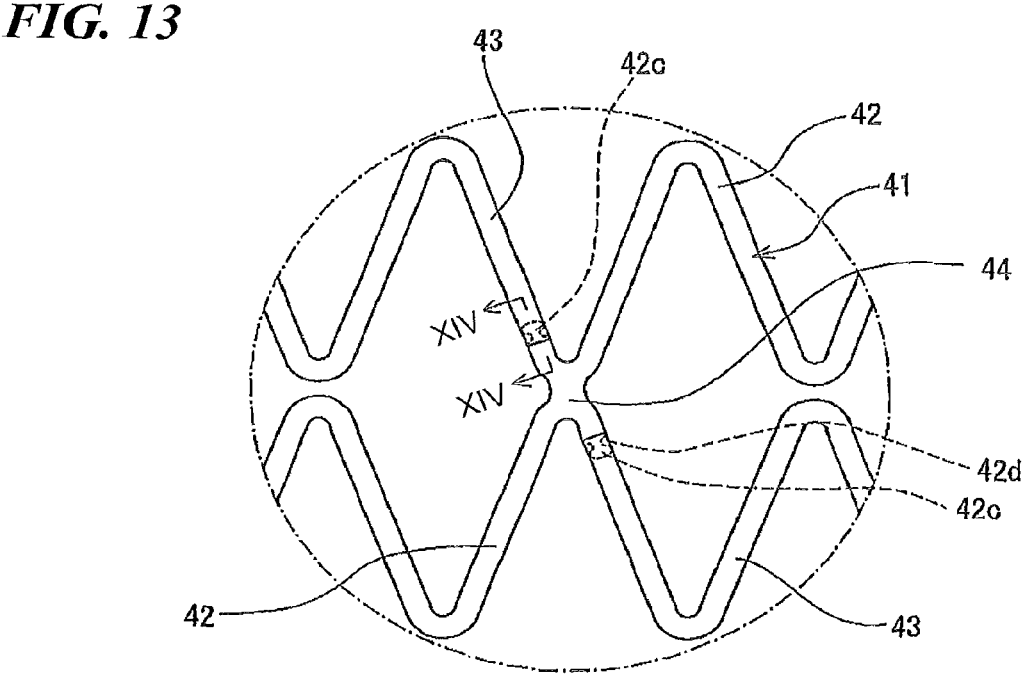
FIG. 13 is an enlarged view of the circled portion of the stent shown in FIG. 11.
Figure 14:
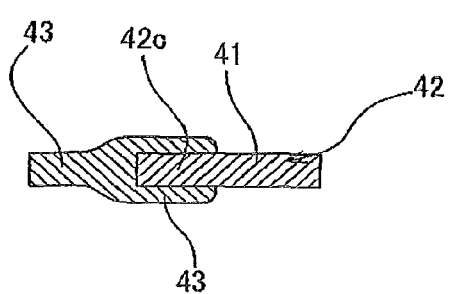
FIG. 14 is an enlarged cross-sectional view taken along the section line XIV-XIV in FIG. 13.
Figure 15:
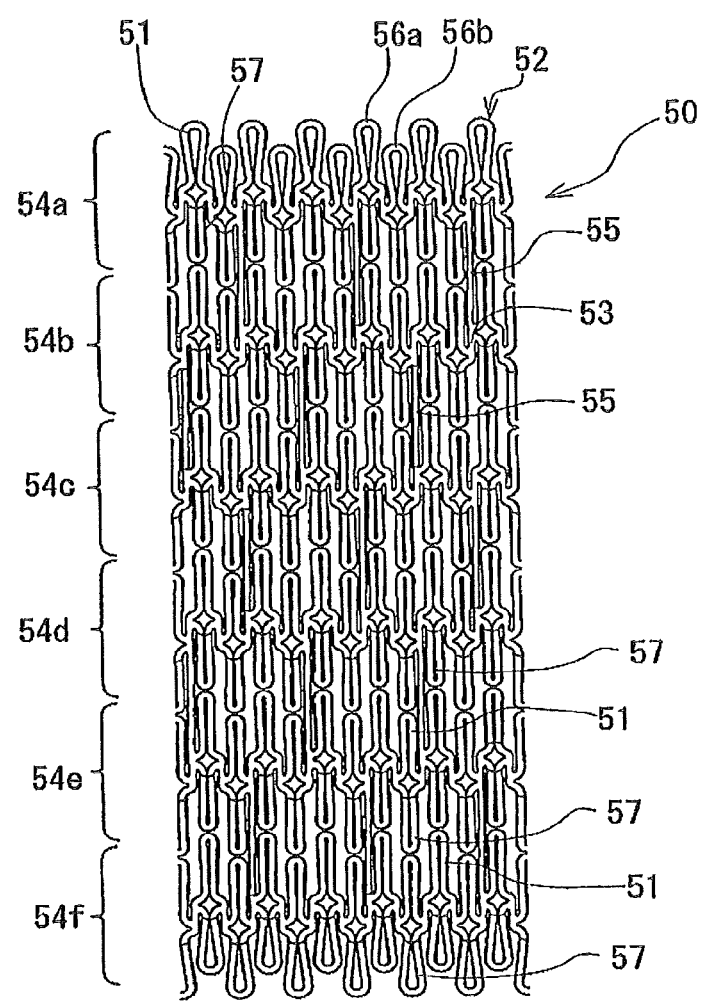
FIG. 15 is a front view of a stent according to a yet further embodiment.

In the embodiment of the stent shown in FIGS. 13 and 14, the metallic linear spiral member 42 has joint parts 42c which extend in the directions of the biodegradable material-made linear components 43 from a link part 44. An end portion of the biodegradable material-made linear component 43 is joined to the joint part 42c. In this stent, as shown in FIG. 13, free ends of the joint parts 42c have rounded corner portions. Further, the joint part 42c has means for restraining disconnection of the biodegradable material-made linear component 43 from the metallic stent base body 41. Specifically, as shown in FIG. 13, an end portion of the biodegradable material-made linear component 43 envelopes only a free end portion of the joint part 42c, and the link part 44 of the metallic linear spiral member 42 has its surface exposed. As shown in FIG. 13, the means for restraining disconnection comprises notches 42d which are formed in side portions of the free end portions of the joint parts 42c of the metallic linear spiral members 42, and a part of the biodegradable material-made linear components 43 penetrates into each of the notches 42d in the free end portions of the joint parts 42c. By virtue of the notches 42d in the free end portions of the joint parts 42c and those portions of the biodegradable material-made linear components 43 which penetrate the notches, the disconnection between both these members is restrained. The notches 42d in the free end portions of the joint parts 42c together with the portions of the biodegradable material-made linear components 43 which penetrate the notches are the means for restraining disconnection of the biodegradable material-made linear component 43 from the metallic stent base body 41.

In the stent 40 according to this embodiment, the number of wavy-linear annular members forming the stent 40 is twelve, in the example shown in FIGS. 10 and 11. The number of the wavy-linear annular members differs depending on the length of the stent, and is preferably 4 to 50, particularly 8 to 35.

In addition, the stent disclosed here may also be a so-called balloon-expandable stent, that is, a stent formed to be a substantially tubular body which has a diameter suitable for insertion into a lumen in vivo, and which can be expanded when a force dilating in the outer radial direction from the inside of the tubular body is exerted thereon.

Figure 16:
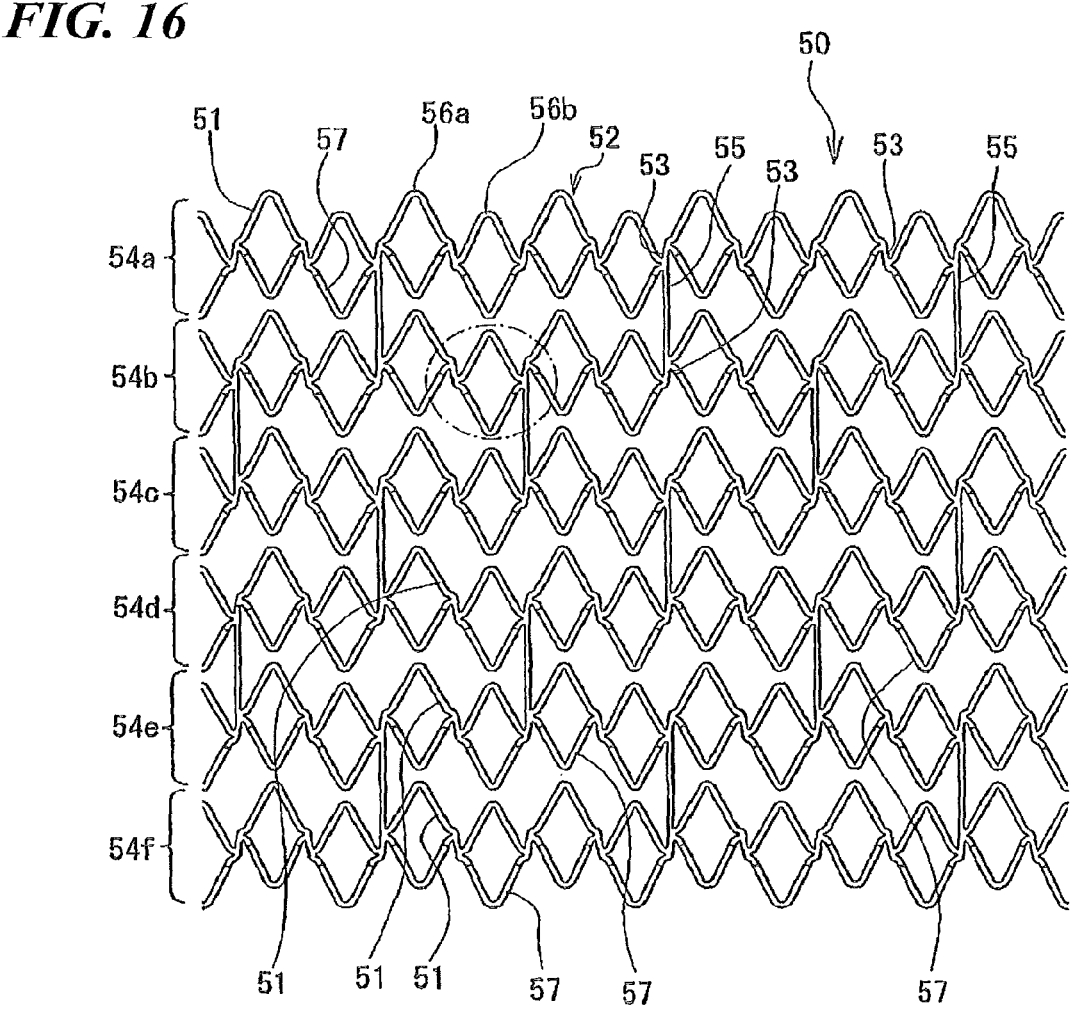
FIG. 16 is a developmental view of the stent shown in FIG. 15 when the stent is expanded.
Figure 17:
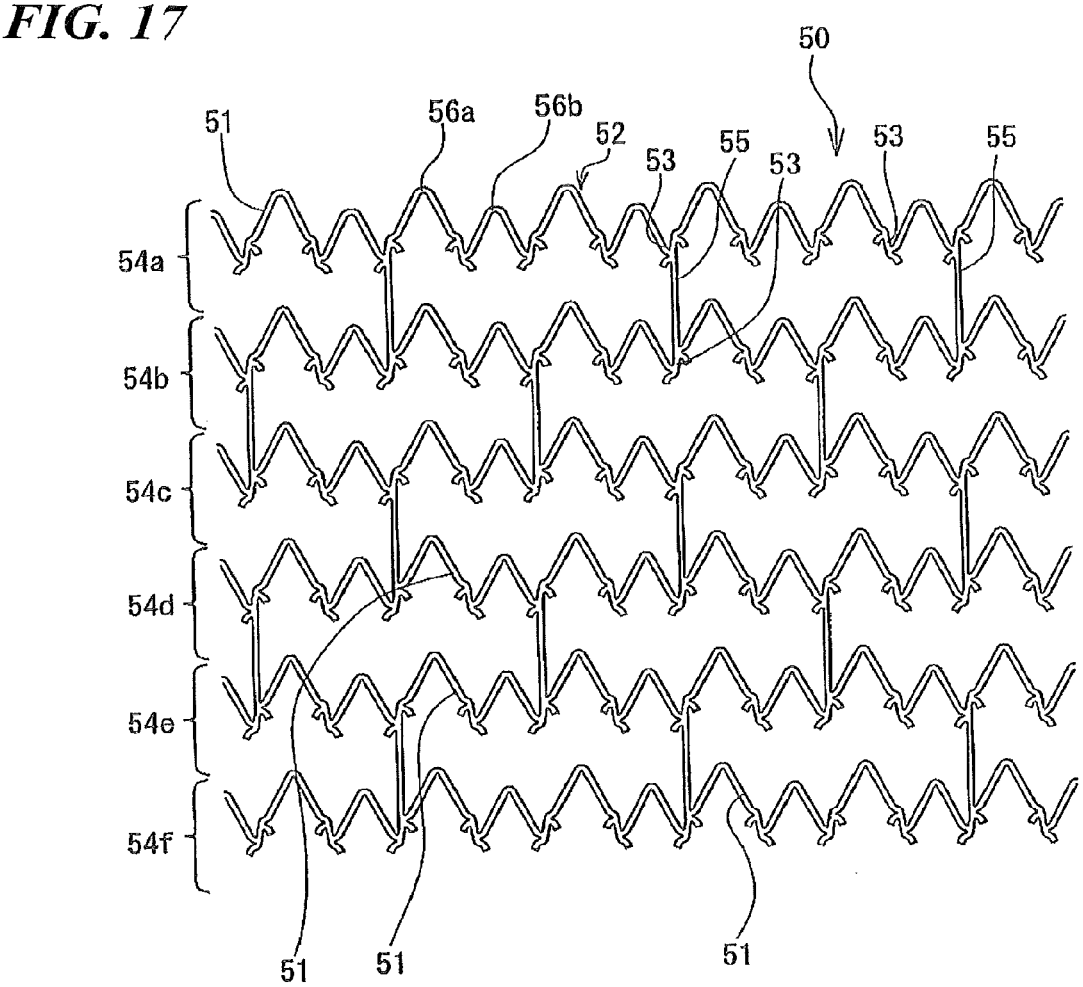
FIG. 17 is an explanatory drawing illustrating operation of the stent shown in FIG. 15.

FIGS. 15-18 illustrate a further embodiment of the stent. FIG. 17 shows a condition of the stent in which the biodegradable material-made linear components have disappeared from the stent, namely, a condition where only a metallic stent base body is present. In this stent, a basic skeleton portion of the stent is composed of the metallic linear components, so that the stent shape is maintained even after the disappearance of the biodegradable material-made linear components.

The stent 50 according to this embodiment is a so-called balloon-expandable stent, composed of annular members 54a-54f in each of which a plurality of annular components 52 each elongated in the axial direction of the stent, having an opening in a central portion thereof and being in a collapsed form are arranged so as to surround the center axis of the stent. The circumferentially adjacent annular components 52 are connected at a connection part 53. A plurality of the annular members 54 are arrayed in the axial direction of the stent. Further, the connection part or parts 53 of the annular member 54 and the connection part or parts 53 of the axially adjacent annular member 54 are interconnected at least at one position by a link part or parts 55.

In addition, the connection parts 53 and the link part or parts 55 are composed of the metallic linear components. The whole or some of the annular components 52 each have a structure in which a part of the portion not connected with the connection part 53 of the annular component 52 is composed of the biodegradable material-made linear component, while the other part is composed of the metallic linear component.

In the stent 50 according to this embodiment, the annular component 52 has a structure in which portions 51 on the side of one end of the stent 50 relative to the connection part 53 is composed of the metallic linear component, while portions 57 on the side of the other end of the stent 50 relative to the connection part 53 is wholly (inclusive of substantially wholly) composed of the biodegradable material-made linear component.

The stent in this embodiment is a balloon-expandable stent as above-mentioned, and the material forming the metallic linear components 51 is preferably a material which is relatively easily plastically deformable. The material forming the metallic linear components 51 is preferably a material having a certain degree of biocompatibility. Examples of such a material include stainless steels, tantalum and tantalum alloys, platinum and platinum alloys, gold and gold alloys, cobalt-based alloys, cobalt-chromium alloys, titanium alloys, niobium alloys and the like. In addition, after the material is formed into the stent shape, the formed body may be plated with a noble metal (gold, platinum). Among the stainless steels, preferred is SUS316L, which is the highest in corrosion resistance.

As the biodegradable material used for forming the biodegradable material-made linear component, a biodegradable metal or a biodegradable polymer is preferably used. In addition, the biodegradable material here is preferably one which has adhesiveness to the material forming the metallic linear components. As the biodegradable material and the biodegradable polymer, the respective ones mentioned above can be used suitably. Those portions of the metallic linear components which are joined to the biodegradable material-made linear components may be wholly or partly surface treated, for enhancing adhesion to the material forming the biodegradable material-made linear components. As the surface treatment, the above-mentioned treatments can be used suitably.

In addition, a physiologically active substance may be contained in the material for forming the biodegradable material-made linear components. As the physiologically active substance, the above-mentioned ones can be used suitably.

Figure 18:
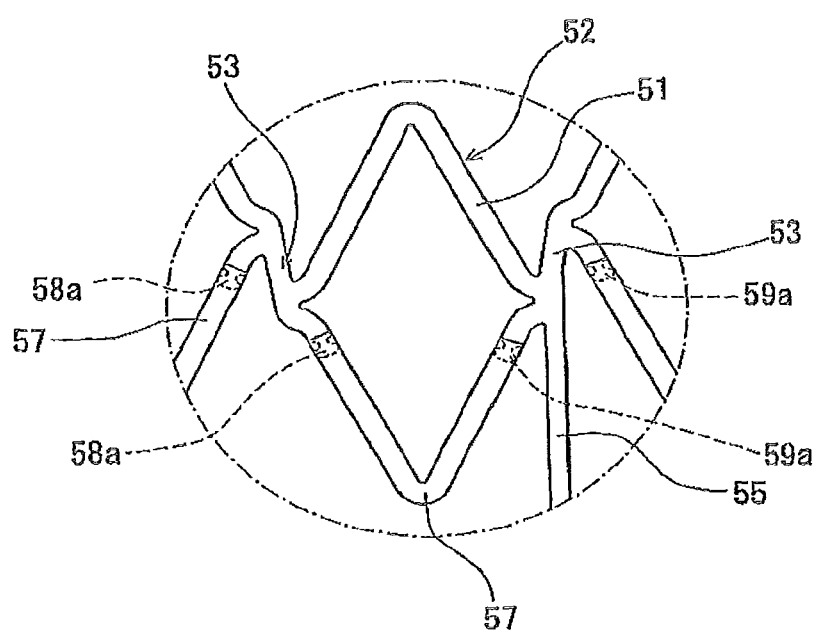
FIG. 18 is an enlarged view of a portion of the stent shown in FIG. 17.

As shown in FIG. 18, in the stent 50 according to this embodiment, the metallic linear component 51 has joint parts 58a and 59a for joining to the biodegradable material-made linear components 57. End portions of the biodegradable material-made linear components 57 are joined to the joint parts 58a and 59a. In this stent, as shown in FIG. 18, free ends of the joint parts 58a and 59a have corner portions rounded. Further, the joint parts 58a and 59a have means for restraining disconnection of the biodegradable material-made linear component 57 from the metallic stent base body. Specifically, as shown in FIG. 18, notches are formed in side portions of free end portions of the joint parts 58a and 59a of the metallic linear components 51, and a part of the biodegradable material-made linear components 57 penetrates each of the notches in the free end portions of the joint parts 58a and 59a. By virtue of the notches in the free end portions of the joint parts 58a and 59a and those portions of the biodegradable material-made linear components 57 which are penetrating the notches, the disconnection between both these members is restrained. The notches in the free end portions of the joint parts 58a and 59a, in combination with the portions of the biodegradable material-made linear components 57 which penetrate the notches, represent an example of the means for restraining disconnection of the biodegradable material-made linear component from the metallic stent base body.

The diameter of the stent when not expanded is preferably about 0.8 to 1.8 mm, more preferably 0.9 to 1.6 mm. In addition, the length of the stent when non-expanded is preferably about 8 to 40 mm. The length of one annular member 54 is preferably about 1.0 to 2.5 mm.

The stent 50 according to this embodiment is composed of the annular members 54 in each of which a plurality of the annular components 52, each elongated in the axial direction of the stent and having an opening in its central portion and being in a collapsed form, are arranged so as to surround the center axis of the stent 50. The circumferentially adjacent annular components 52 (56a, 56b) are connected at a connection part 53. A plurality of the annular members 54 (54a, 54b, 54c, 54d, 54e, and 54f) are arrayed in the axial direction of the stent. Further, the connection part or parts 53 of the annular member 54 and the connection part or parts 53 of the axially adjacent annular member 54 are interconnected at least at one position by a link part or parts 55.

Furthermore, of the annular components 52 in each of the annular members 54 (54a, 54b, 54c, 54d, 54e and 54f), one annular component 56b of the adjacent annular components is located on the proximal end side in the axial direction of the stent 50 relative to the other annular component 56a. That is, the one annular component 56b is set back proximally in the axial direction of the stent 50 relative to the other annular component 56a as illustrated in FIG. 16. End portions of each annular member 54 project in a zigzag fashion. The end portions projecting in the zigzag fashion, of each annular member 54, penetrate the adjacent annular member. For example, each of the annular components 56a in the annular member 54b is positioned between two of the annular components 56b in the annular member 54a so that the annular components 56a in the annular member 54b axially overlap the annular components 56b in the annular member 54a. The connection parts 53 of the annular members 54 are set substantially parallel (when the stent is not expanded) to the center axis of the stent 50.

In the stent 50 according to this embodiment, as shown in FIG. 17, the connection parts 53, the link parts 55 and portions 51, on one end side of the connection parts 53, of all the annular components 52 are composed of the metallic linear components. In this stent, therefore, a basic skeleton portion of the stent is composed of the metallic linear components, so that the stent shape is maintained even after the disappearance of the biodegradable material-made linear components. In addition, portions 57, on the other end side of the connection parts 53, of all the annular components 52 are wholly (inclusive of substantially wholly) composed of the biodegradable material-made linear components. In the stent 50 in this embodiment, through disappearance of the biodegradable material-made linear components, substantially half the annular components 52 will disappear. Consequently, as shown in FIG. 17, the distance between the linear components sustaining the stent shape is enlarged; in other words, the gaps in the side surface of the stent increases, resulting in a lowering of the force for maintaining the dilation and an enhancement of flexibility.

In the stent 50 according to this embodiment, the annular components in one annular member 54 are so configured that one annular component 56b of the adjacent annular components is located on the side of the proximal end in the axial direction of the stent 50 relative to the other annular component 56a. In other words, end portions of one annular member 54 project in a zigzag fashion. Specifically, one annular member 54a is composed of a plurality of the annular components 56a which have end portions projecting in the distal end side, and a plurality of the annular components 56b which have end portions set back in the proximal direction relative to the annular components 56a and which are each located between the annular components 56a projecting to the distal end side. In the stent 50 in this embodiment, each annular member 54a-54f has an even number of the annular components. Therefore, every pair of the adjacent annular components 56a and 56b are staggered in position from each other in the axial direction of the stent. For stabilization of such a zigzag form, it is preferable to provide an even number of the annular components.

Further, in each annular member 54, the adjacent annular components 52 (56a, 56b) are interconnected in the vicinity of the centers of side portions of the annular components by the short connection part 53. In other words, the connection parts 53 interconnect the annular components 52 (56a, 56b) in the circumferential direction of the stent, to form the annular member. The connection parts 53 are substantially not changed even when the stent 50 is expanded. Therefore, the force at the time of expansion is exerted primarily on the center of each of the annular components, so that the annular components can be expanded (deformed) evenly. In addition, the connection part is a portion where the deformation amount at the time of compression or expansion is small.

Furthermore, in this stent 50, the connection parts 53 are substantially parallel to the center axis of the stent 50. Therefore, when the stent 50 is compressed, there is little limitation on the diameter reduction at the joint parts, so that the stent 50 can be made to be smaller in diameter accordingly.

The number of the annular components 52 is not limited to 12, and is preferably not less than 4. A particularly preferable number of the annular components 52 is 6 to 20. In addition, as mentioned above, it is preferable that the number of the annular components 52 is an even number. The shape of the annular components is preferably such that the annular components become substantially elliptic or substantially rhombic when the stent is expanded. However, other polygonal shapes may also be adopted, for example, a rectangle elongated in the axial direction, a hexagon, an octagon, or the like.

The connection parts 53 of the annular member 54 and the connection parts 53 of the axially adjacent annular member 54 are interconnected by link parts 55 which are comparatively long (as compared with the connection parts). Specifically, the annular member 54a and the axially adjacent annular member 54b are interconnected by link parts 55 interconnecting the connection parts 53. The annular member 54b and the axially adjacent annular member 54c are interconnected by link parts 55 interconnecting the connection parts 53. The annular member 54c and the axially adjacent annular member 54d are interconnected by link parts 55 interconnecting the connection parts 53. The annular member 54d and the axially adjacent annular member 54e are interconnected by link parts 55 interconnecting the connection parts 53. The annular member 54e and the axially adjacent annular member 54f are interconnected by link part 55 interconnecting the connection parts 53. In addition, in the stent according to this embodiment, the link parts 55 are so provided as to interconnect the axially adjacent annular members 54 at a plurality of positions. A configuration may be adopted in which the adjacent annular members are interconnected by the link part at only one position. The number of the link parts 55 provided between the adjacent annular members is preferably in the range of 1 to 5, particularly 1 to 3.

In addition, in the stent 50 according to this embodiment, as viewed along the axial direction, the annular components 52 are so aligned that they are arrayed substantially rectilinearly in relation to the axial direction of the stent 50. Specifically, in the stent 50 in this embodiment, all the annular components adjacent to one another in the axial direction are so aligned that they are arrayed substantially rectilinearly in relation to the axial direction of the stent 50. Also, all the link parts 55 are also arranged substantially parallel to the axial direction of the stent 50. Therefore, torsion would not easily be generated at the link parts 55. When the stent 50 is not expanded, all the connection parts 53 are parallel to the axial direction of the stent 50. Therefore, also at the connection parts 55, torsion would not easily be generated.

In addition, the diameter of the stent when not expanded is preferably about 0.8 to 1.8 mm, more preferably 0.9 to 1.6 mm. The length of the stent when not expanded is preferably about 8 to 40 mm. Further, the length of one annular member in the axial direction is preferably about 1.0 to 2.5 mm.

A stent 301 according to another embodiment is illustrated in FIGS. 19-23. The stent 301 is composed of linear components and comes into close contact with tissue in vivo through deformation when set indwelling in vivo. The stent is configured so that the linear components are deformed to exhibit a force for maintaining dilation when the stent 301 is set indwelling in vivo. The linear components deformed when the stent 301 is set indwelling in vivo are composed of non-biodegradable metallic linear components 304 and a plurality of biodegradable material-made linear components 305 which are joined to the non-biodegradable metallic linear components 304. Further, when left indwelling in vivo, the stent 301 exhibits the force for maintaining the dilation by both the non-biodegradable metallic linear components 304 and the biodegradable material-made linear components 305, and, after a predetermined period of time, biodegradation of the biodegradable material-made linear components 305 proceeds, whereby the dilation-maintaining force is lowered.

Particularly, in the stent 301 according to this embodiment, the linear components deformed when the stent 301 is set indwelling in vivo are comprised of a multiplicity of bent or curved easily deformable parts 304 which are deformed when the stent 301 is set indwelling in vivo, and joint parts which interjoin the easily deformable parts 304 and are little deformed when the stent 301 is set indwelling in vivo. The easily deformable parts 304 are composed of the non-biodegradable metallic linear components which are easily deformable, while the joint parts 305 are composed of the biodegradable material-made linear components.

The stent 301 is a stent which is composed of the linear components, and comes into close contact with a tissue in vivo through deformation when set indwelling in vivo. The linear components compose a multiplicity of the bent or curved easily deformable parts 304 which are deformed when the stent 301 is set indwelling in vivo, and the joint parts 305 which interjoin the easily deformable parts 304 and are little deformed when the stent 301 is set indwelling in vivo. The easily deformable parts 304 are formed of an easily deformable metal, while the joint parts 305 are formed of a biodegradable material.

The stent 301 according to this embodiment is a so-called balloon-expandable stent, specifically, a stent which is formed to be a substantially tubular body, has a diameter suitable for insertion into a lumen in vivo, and is expandable when a force dilating in the radial outward direction from the inside of the tubular body is exerted thereon. The stent is not limited to the balloon-expandable stent, and may be a self-expandable stent.

In the stent 301 in this embodiment, a plurality of annular members 302 formed in an annular shape from linear components are arrayed in the axial direction of the stent 301, with the axially adjacent annular members 302 interconnected by a link part(s) 303.

Figure 20:
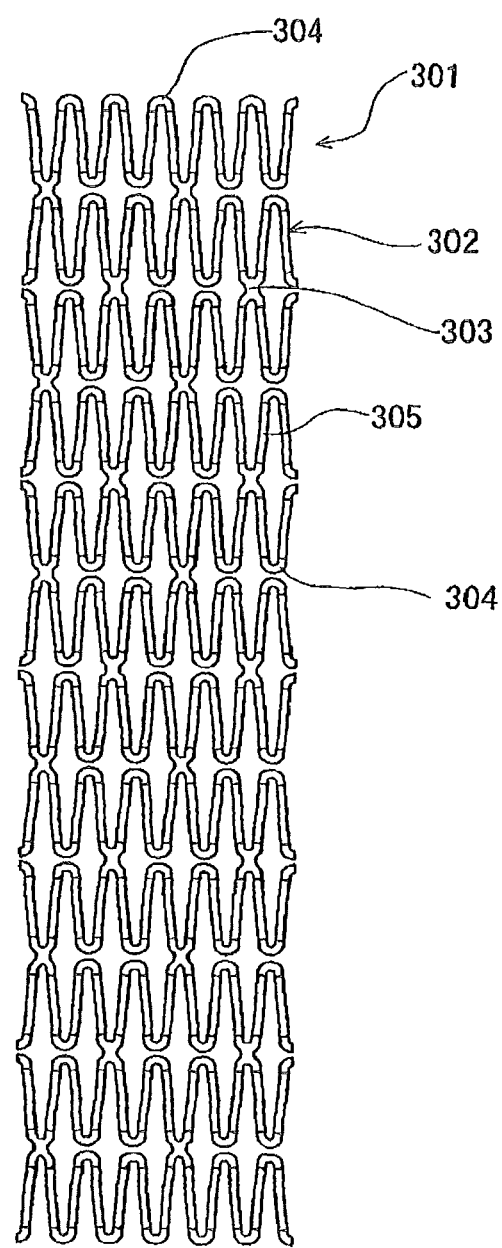
FIG. 20 is a developmental view of the stent of FIG. 19.
Figure 21:
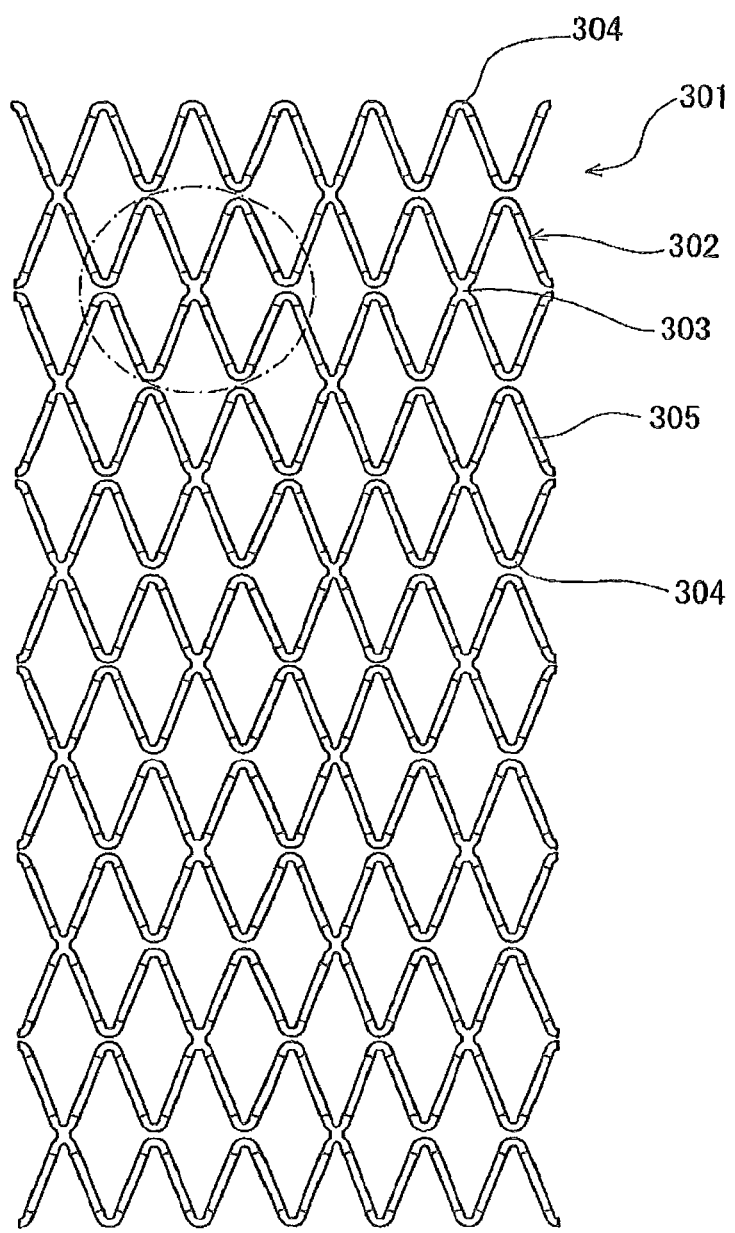
FIG. 21 is a developmental view of the stent of FIG. 19 when the stent is expanded.

Each of the annular members 302 is composed of a multiplicity of the easily deformable parts 304 which are bent or curved to have vertices in the axial direction of the stent, and the joint parts 305 each of which interjoins two free ends of the easily deformable parts 304. As shown in FIGS. 20 and 21, the easily deformable portion 304 is a portion which is deformed when the stent is set indwelling in vivo, that is, a portion showing a relatively large deformation amount at the time of expansion (dilation). On the other hand, the joint part 305 is a portion which is little deformed when the stent is set indwelling in vivo, that is, a portion which shows a small deformation amount at the time of expansion (dilation).

In the stent 301 according to this embodiment, all the bent or curved portions having vertices in the axial direction of the stent 301 are the easily deformable parts 304, and are formed of an easily deformable metal. All rectilinear portions interjoining the easily deformable parts 304 are the joint parts 305, and are formed of a biodegradable material.

Figure 19:
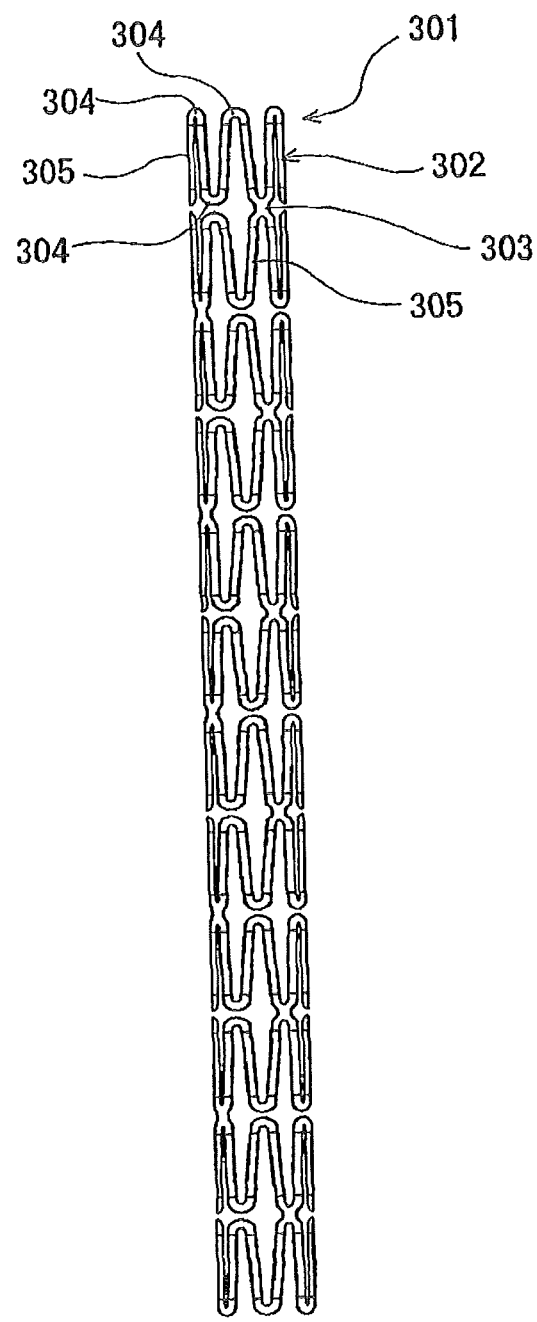
FIG. 19 is a front view of a stent according to still another embodiment.

As shown in FIGS. 19 to 21, the stent 301 in this embodiment has a configuration in which a plurality of wavy-linear annular members 302 are arrayed to be adjacent with each other in the axial direction of the stent 301 and are interconnected.

The number of the wavy-linear annular members 302 forming the stent 301 is twelve in the embodiment shown in FIGS. 19-21. The number of the wavy-linear annular members 302 differs depending on the length of the stent, and is preferably in the range of 4 to 50, particularly 8 to 35.

Each of the wavy-linear annular members 302 is composed of an endless linear component (specifically, a wavy-linear member). The endless linear component includes a plurality of one-end-side bent portions having vertices on one end side in the axial direction of the stent 301, and a plurality of other-end-side bent portions having vertices on the other end side in the axial direction of the stent 301, and is continuous in an annular fashion.

The stent in this embodiment is a balloon-expandable stent, as above-mentioned, and the material forming the easily deformable parts 304 is preferably a material having a relatively easily plastically deformable property. In addition, the material forming the easily deformable parts 304 preferably has a certain degree of biocompatibility. Examples of such a material include stainless steels, tantalum and tantalum alloys, platinum and platinum alloys, gold and gold alloys, cobalt-based alloys, cobalt-chromium alloys, titanium alloys, niobium alloys and the like. In addition, after the material is formed into a stent shape, the formed body may be plated with a noble metal (gold, platinum). Among the stainless steels, preferred is SUS316L, which is the highest in corrosion resistance.

As the biodegradable material used for forming the joint parts 305, a biodegradable metal or a biodegradable polymer is preferably used. Further, the biodegradable material here is preferably one which imparts adhesiveness to the material forming the stent.

As the biodegradable metal, the above-mentioned ones can be used. Similarly, as the biodegradable polymer, the above-mentioned ones can be used. In addition, those portions of the easily deformable parts which are interjoined by the joint parts may be wholly or partly surface treated, for enhancing adhesion to the material forming the joint parts. The surface treatment is preferably carried out by a method in which the relevant surface is coated with a high-affinity material serving as a primer. As the primer material, the above-mentioned ones can be used.

A physiologically active substance may be contained in the material forming the joint parts. As the physiologically active substance, the above-mentioned ones can be used.

Figure 22:
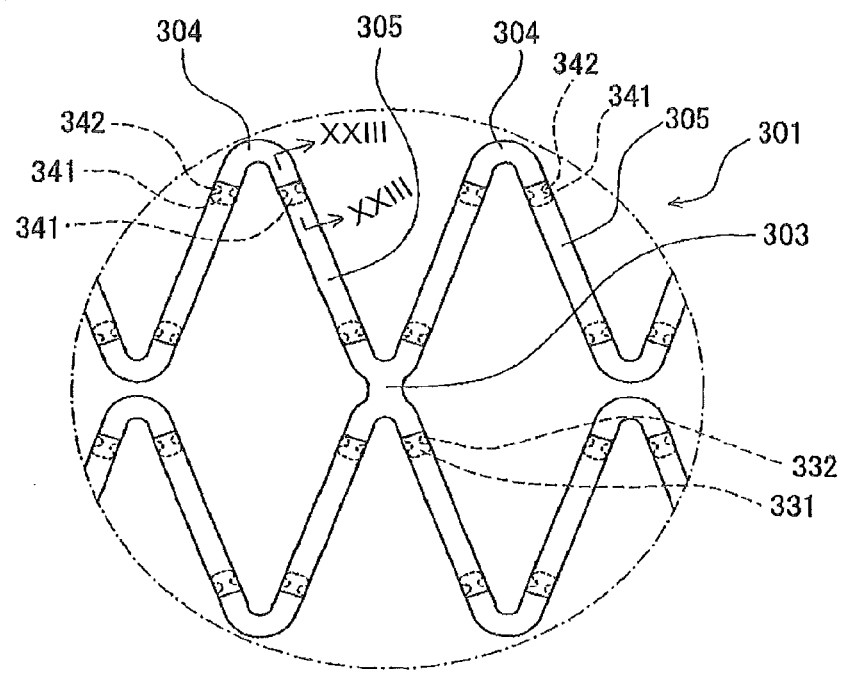
FIG. 22 is an enlarged view of the circled portion of the stent shown in FIG. 21.
Figure 23:
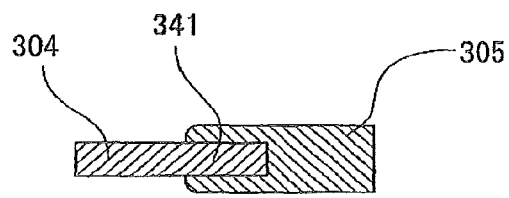
FIG. 23 is an enlarged cross-sectional view taken along the section line XXIII-XXIII of FIG. 22.

As shown in FIG. 22, free ends 341 of the easily deformable parts 304 joined to the joint parts 305, preferably, have their corner portions rounded. In addition, the joint part 305 and the easily deformable part 304 preferably have means for restraining disconnection of the easily deformable part 304 from the joint part 305. In the stent 301 in this embodiment, as shown in FIG. 23, the joint parts 305 envelope only the free end parts of the easily deformable parts, and the other parts of the easily deformable parts 304 have their surfaces exposed.

In the stent 301 according to this embodiment, as shown in FIGS. 21 and 22, notches 342 are formed in side portions of the free end portions 341 of the easily deformable parts 304, and a part of the joint part 305 penetrates each of the notches 342. By virtue of the notches 342 in the easily deformable parts 304 and those parts of the joint parts 305 which penetrate the notches 342, disconnection of the easily deformable part from the joint part is restrained, thus providing an example of the means for restraining disconnection of the easily deformable part 304 from the joint part 305. The joint part 305 is preferably rectilinear in shape as shown in the figures, but may also be curved in shape.

In addition, in the stent 301 according to this embodiment, as shown in FIGS. 19-21 (especially FIG. 21), link parts 303 interconnecting the axially adjacent wavy-linear annular members 302 are each formed integrally with the easily deformable part 304. Therefore, the link parts 303 are formed of the material that forms the easily deformable parts 304. Where the link parts 303 are thus formed integrally with the easily deformable parts 304 from the metallic material forming the easily deformable parts 304, the structure has a good dilation-maintaining force.

Figure 24:
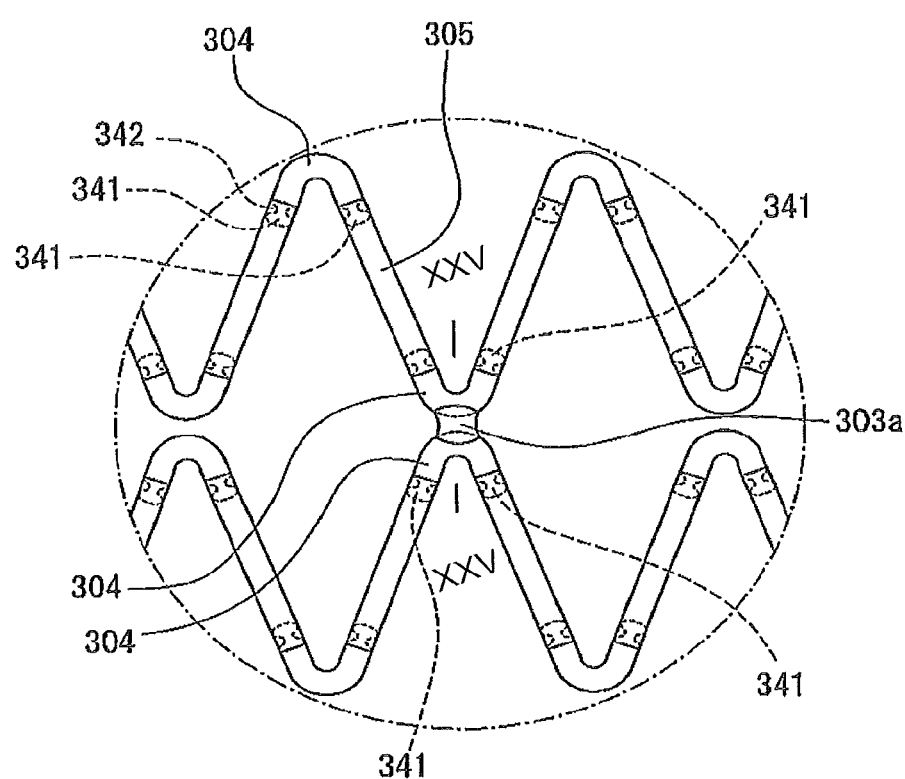
FIG. 24 is an enlarged view of a portion of a stent according to another embodiment disclosed here.
Figure 25:
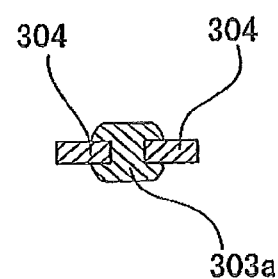
FIG. 25 is an enlarged cross-sectional view taken along the section line XXV-XXV in FIG. 24.

The form of the link part is not limited to the above-mentioned, and may be one as shown in FIGS. 24 and 25. In the stent in this embodiment, link parts 303a interconnecting adjacent wavy-linear annular members 302 are not integral with easily deformable parts 304, and are formed of a biodegradable material. Therefore, this structure has a good deformability in the axial direction of the stent. As the biodegradable material, the above-mentioned ones can be used suitably. In addition, those portions of the easily deformable parts 304 which are joined to the link parts 303a are preferably surface treated either wholly or partly, for enhancing adhesion to the material forming the joint parts. The surface treatment is preferably carried out by a method in which the relevant surface is coated with a high-affinity material serving as a primer. As the surface treatment method, the above-mentioned ones can be used suitably.

Figure 26:
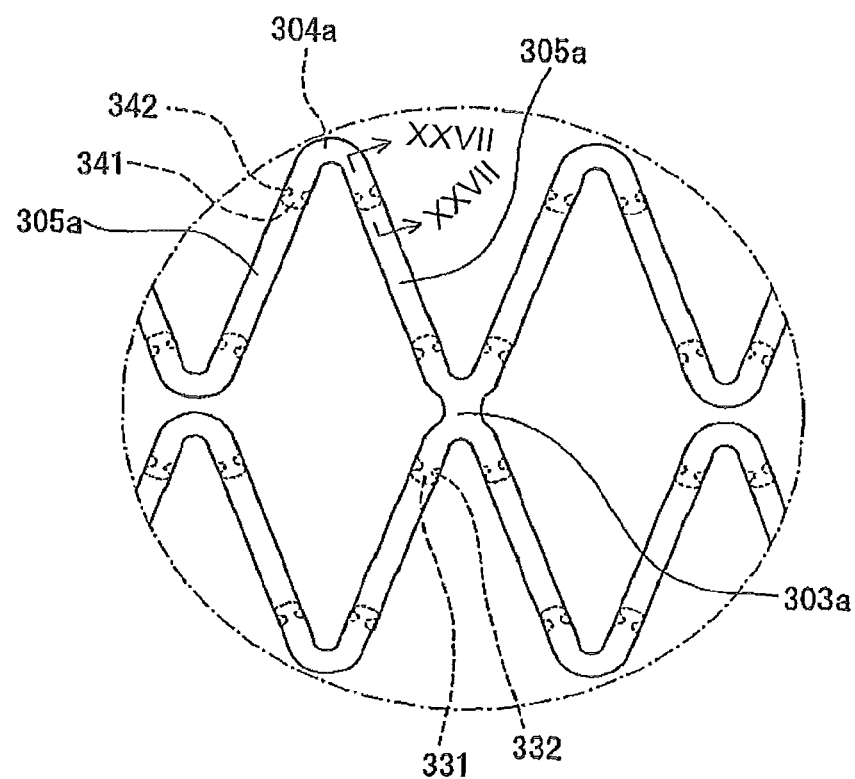
FIG. 26 is an enlarged view of a portion of a stent according to another embodiment disclosed here.
Figure 27:
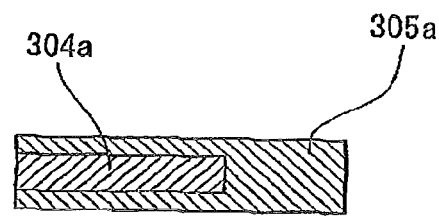
FIG. 27 is an enlarged cross-sectional view taken along the section line XXVII-XXVII in FIG. 26.

The form of joining of the easily deformable parts 304 by the joint parts 305 is not limited to the above-mentioned, and may be one as shown in FIGS. 26 and 27 (especially, FIG. 27).

In the stent according to this embodiment, joint parts 305a cover the outer and inner surfaces of easily deformable parts 304a. This helps ensure that the outer and inner surfaces of the stent are gently curved surfaces free of stepped portions. The joint part may cover only one of the outer surface and the inner surface of the easily deformable part.

Also in the stent in this embodiment, as shown in FIG. 26, notches 342 are formed in side portions of free end portions 341 of the easily deformable parts 304a, and a part of the material forming the joint parts 305a penetrates each of the notches 342 in the easily deformable parts 304a. By virtue of the notches 342 in the easily deformable parts 304a and those parts of the joint parts 305a which penetrate into the notches 342, disconnection of the easily deformable part from the joint part is restrained, thus providing an example of means for restraining disconnection of the easily deformable part from the joint part. Those surface parts of the easily deformable parts 304a which are covered with the joint parts 305a are preferably surface treated, for enhancing adhesion thereof to the material forming the joint parts. The surface treatment is preferably carried out by a method in which the relevant surface is coated with a high-affinity material serving as a primer. As the surface treatment method, the above-mentioned ones can be used suitably. The free ends 341 of each easily deformable part 304a which are joined to the joint parts 305a preferably have their corner portions rounded.

Figure 28:
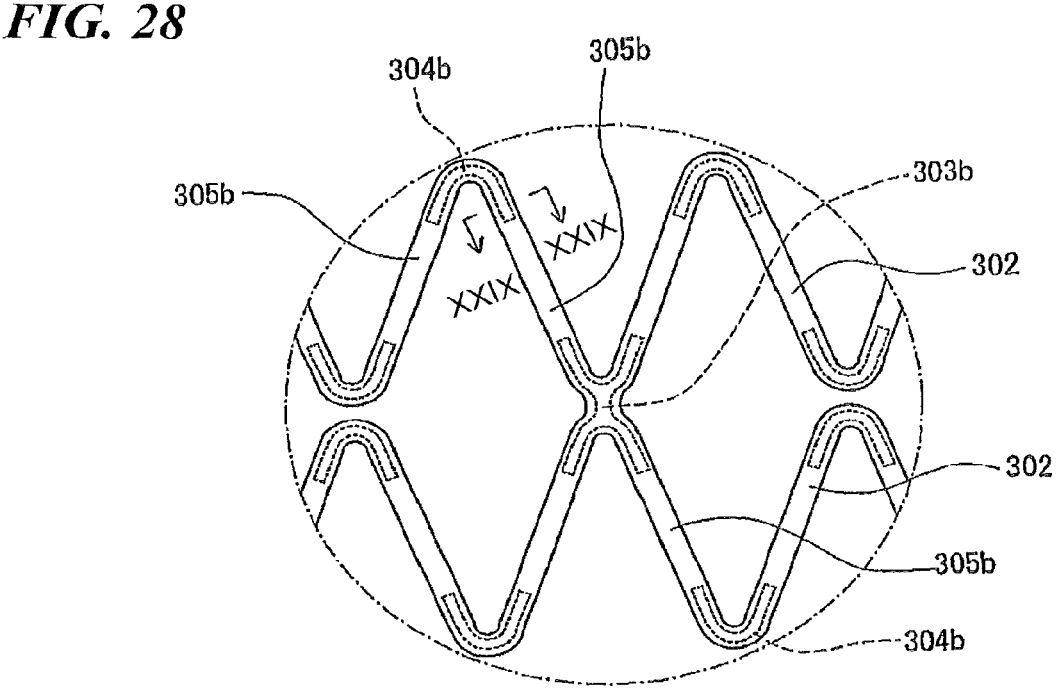
FIG. 28 is an enlarged view of a portion of a stent according to another embodiment disclosed here.
Figure 29:
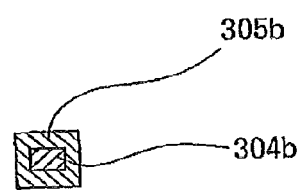
FIG. 29 is an enlarged cross-sectional view taken along the section line XXIX-XXIX in FIG. 28.

The form of joining of the easily deformable parts 304 by the joint parts 305 is not limited to the above-mentioned, and may be one as shown in FIGS. 28 and 29. In the stent according to this embodiment, easily deformable parts 304b are embedded in joint parts 305b. This helps ensure that the outer and inner surfaces of the stent are gently curved surfaces free of stepped portions. Also, disconnection of the easily deformable part from the joint part is restrained. The whole surface of the easily deformable part 304b covered with the joint part 305b is preferably surface treated, for enhancing adhesion thereof to the material forming the joint part. The surface treatment is preferably conducted by a method in which the surface is covered with a high-affinity material serving as a primer. As the surface treatment method, the above-mentioned ones can be used suitably. In addition, free ends of each easily deformable part which are joined to the joint parts preferably have their corner portions rounded.

In the stent in this embodiment, as shown in FIG. 28, link parts 303b interconnecting adjacent wavy-linear annular members 302 are formed integrally with the easily deformable parts 304b. Therefore, the link parts 303b are formed of the material that forms the easily deformable parts 304b. Where the link parts 303b are thus formed integrally with the easily deformable parts 304b from the metallic material forming the easily deformable parts 304b, the resulting structure has a good dilation-maintaining force.

Figure 30:
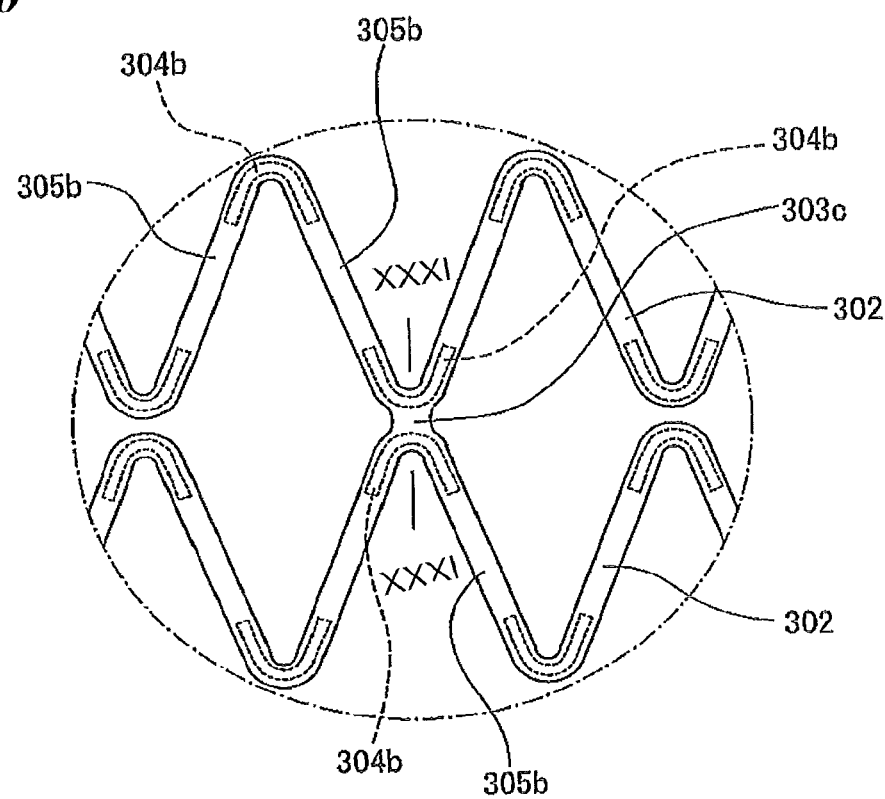
FIG. 30 is an enlarged view of a portion of a stent according to another embodiment disclosed here.
Figure 31:
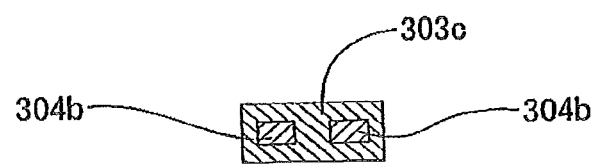
FIG. 31 is an enlarged cross-sectional view taken along the section line XXXI-XXXI in FIG. 30.

An alternative form of the link part is shown in FIGS. 30 and 31. In the stent according to this embodiment, link parts 303c interconnecting adjacent wavy-linear annular members 302 are not integral with easily deformable parts 304b, and are formed of a biodegradable material. Therefore, the structure has good deformability in the axial direction of the stent. As the biodegradable material, the above-mentioned ones can be used suitably. In addition, those parts of the easily deformable parts 304b which are interjoined by the link parts 303c are preferably surface treated either wholly or partly, for enhancing adhesion thereof to the material forming the joint parts. The surface treatment is preferably carried out by a method in which the relevant surface is coated with a high-affinity material serving as a primer. As the surface treatment method, the above-mentioned ones can be used suitably.

The diameter of the stent when the stent is not expanded is preferably about 0.8 to 1.8 mm, more preferably 0.9 to 1.6 mm. The length of the stent when the stent is not expanded is preferably about 8 to 40 mm. The length of one wavy-linear annular member 302 is preferably about 1.0 to 2.5 mm.

Figure 32:
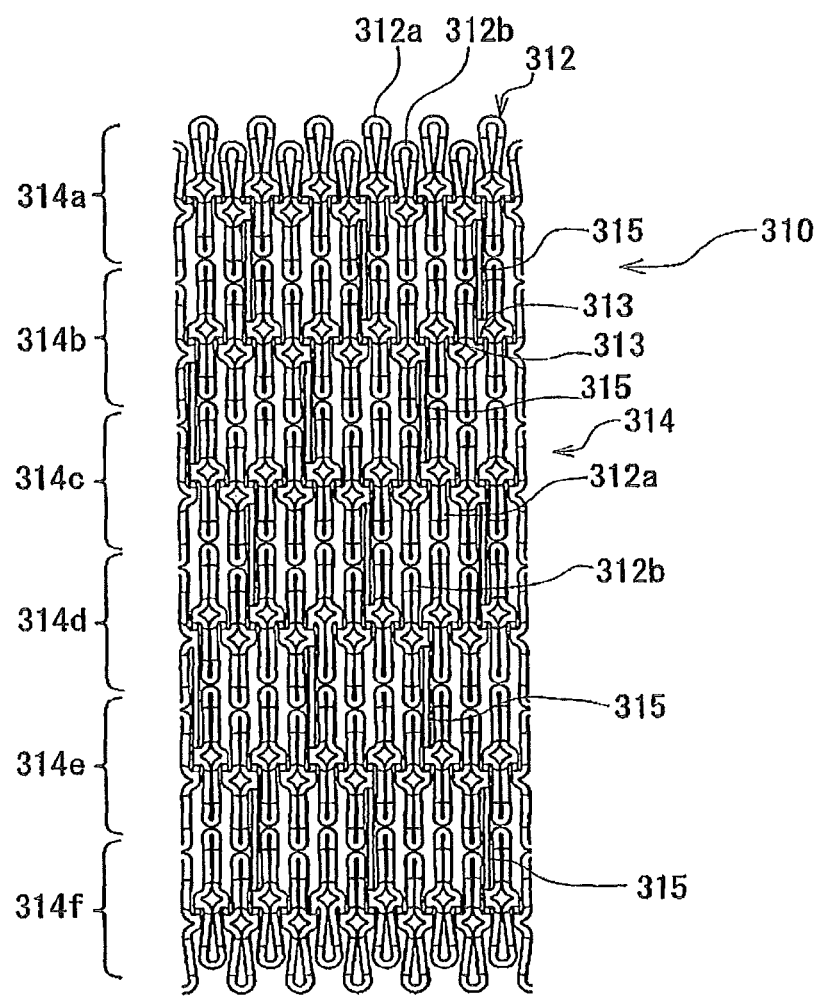
FIG. 32 is a developmental view of a stent according to a yet further embodiment disclosed here.
Figure 33:
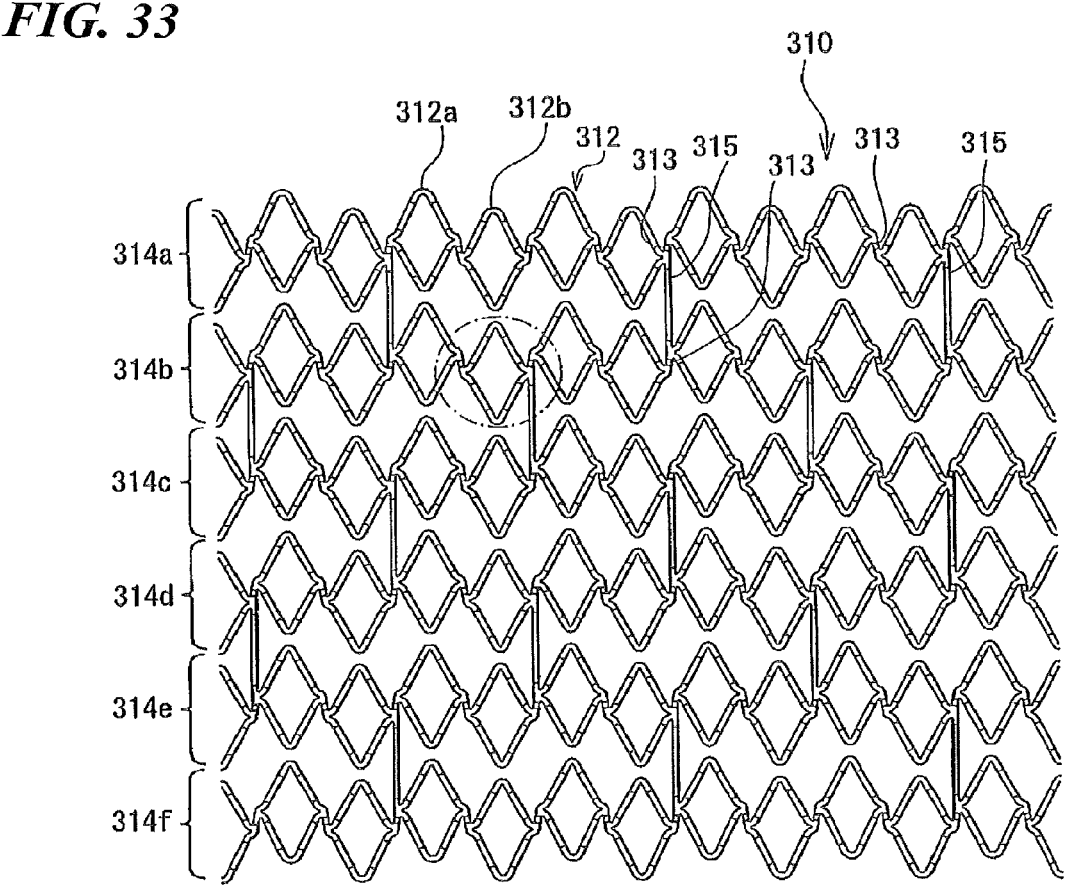
FIG. 33 is a developmental view of the stent of FIG. 32 when the stent is expanded.

The stent is not limited to the above-mentioned one in which the stent is composed of wavy-linear annular members. FIGS. 32-35 illustrate a stent according to further embodiments. As shown in FIGS. 32 and 33, the stent 310 according to this embodiment is a stent which, like the above-mentioned stent 301, is formed to be a substantially tubular body, has a diameter suitable for insertion in vivo, and can be expanded when a force dilating radially outwards from the inside of the tubular body is exerted thereon.

The stent 310 is composed of annular members 314a-314f in each of which a plurality of annular components 312 each elongated in the axial direction of the stent, having an opening in a central portion thereof and being in a collapsed form are arranged so as to surround the center axis of the stent 310. The circumferentially adjacent annular components 312 (312a, 312b) are connected at connection parts 313. A plurality of the annular members 314 (314a, 314b, 314c, 314d, 314e, and 314f) are arrayed in the axial direction of the stent. In addition, the connection part(s) 313 of the annular member 314 and the connection part(s) 313 of the adjacent annular member 314 are interconnected at least at one position by a link part(s) 315. Further, the annular components 312 in each of the annular members 314 (314a, 314b, 314c, 314d, 314e, and 314f) are so configured that one annular component 312b of the circumferentially adjacent annular components is located on the side of a proximal end (i.e., is set back proximally) in the axial direction of the stent 310 relative to the other annular component 312a, the end portions of each annular member 314 project in a zigzag fashion, and the end portions of each annular member 314 which project in a zigzag fashion penetrate the adjacent annular member. In addition, the joint parts 313 of the annular members 314 are parallel (inclusive of substantially parallel), when the stent 310 is not expanded, to the center axis of the stent 310.

Figure 34:
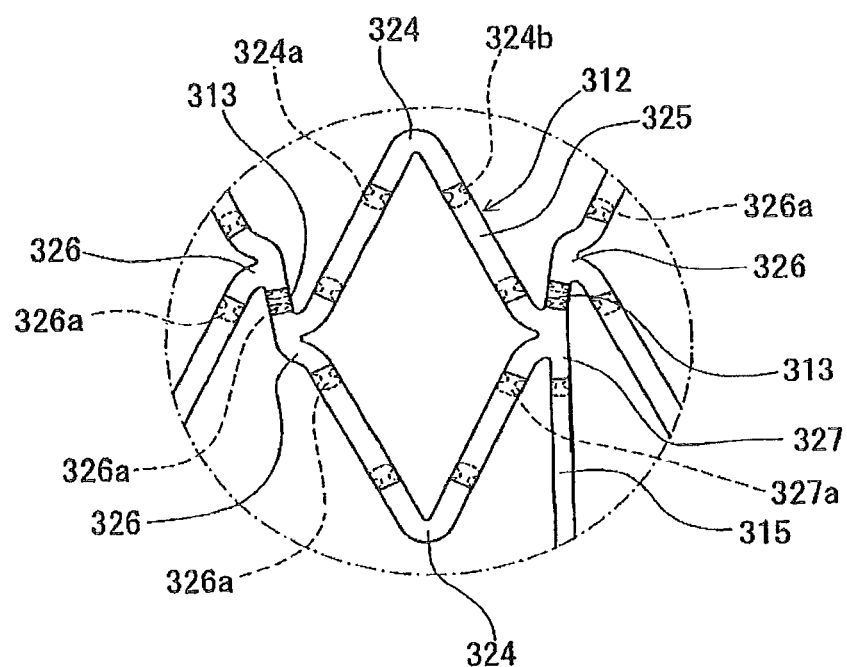
FIG. 34 is an enlarged view of the circled portion of the stent shown in FIG. 33.

As shown in FIG. 34, in the stent 310 according to this embodiment, each annular component 312 composes easily deformable parts 324 which are each bent or curved to have a vertex in the axial direction of the stent, and easily deformable parts 326 which are each bent or curved to have a vertex in the circumferential direction of the stent. In addition, the easily deformable part 324 and the easily deformable part 326 adjacent to each other are interjoined or joined together by a joint part 325. Accordingly, one annular component 312 has four easily deformable parts and four joint parts. As shown in FIG. 34, at least one linear component 312 in the annular member 314 has an easily deformable part 327 which is an easily deformable part bent or curved to have a vertex in the circumferential direction of the stent and which has a portion to be linked to a link part 315.

The easily deformable parts 324, 326, and 327 are formed of an easily deformable metal, whereas the joint parts 325 are formed of a biodegradable material. As the easily deformable metal forming the easily deformable parts and the biodegradable material forming the joint parts, the above-mentioned respective one are preferably used.

In the stent 310 in this embodiment, the circumferentially adjacent annular components 312 are interconnected by the connection parts 313, to form the annular member 314. In the stent 310 in this embodiment, the connection parts 313 are not integral with the easily deformable parts, and are formed of a biodegradable material. Therefore, the structure has good deformability in the axial direction. As the biodegradable material, the above-mentioned ones can be used suitably.

In the stent according to this embodiment, as shown in FIG. 34, notches (for example, notches 324b) are formed in side portions of respective free end portions 324a, 326a, and 327a of the easily deformable parts 324, 326, and 327, and a part of the material forming the joint parts 325 or the connection parts 313 penetrate the respective notches (for example, the notches 324b) of the easily deformable parts 324, 326, and 327. By virtue of the notches in the easily deformable parts 324 or the connection parts 313 and those parts of the joint parts 325 penetrating the notches, disconnection of the joint part from the easily deformable part or connection part is restrained, thus providing an example of a means for restraining disconnection.

In addition, respective free end portions of the easily deformable parts 324, 326, and 327 which are joined to the joint parts 325 or the connection parts 313, preferably, have their corner portions rounded.

The surface portions of the easily deformable part which are covered by the joint part 325 and the connection part 313 are preferably surface treated, for enhancing adhesion thereof to the material forming the joint parts. The surface treatment is preferably carried out by a method in which the relevant surface is coated with a high-affinity material serving as a primer. As the surface treatment method, the above-mentioned ones can be used suitably.

Figure 35:
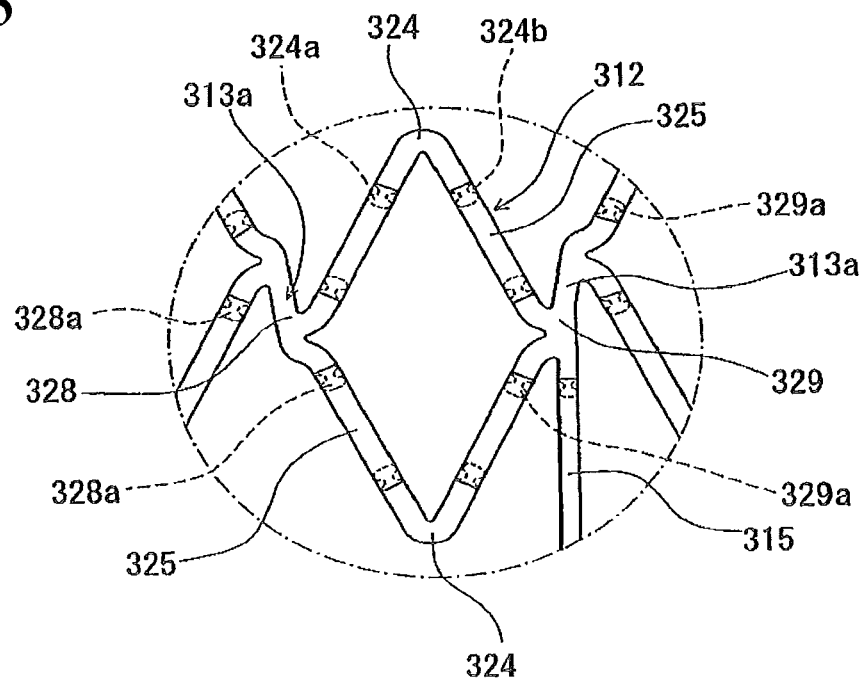
FIG. 35 is an enlarged view of a portion of a stent according to another embodiment disclosed here.

In the stent according to the embodiment shown in FIG. 35, the adjacent annular components 312 are interconnected by the connection parts 313a, to form the annular member 314. In the stent in this embodiment, the connection parts 313a are formed integrally with the easily deformable parts. In this case, the easily deformable parts 328 and 329 which are adjacent to each other and have a vertex in the circumferential direction of the stent, are united with each other, so that the stent exhibits a good dilation-maintaining force.

In the stent in this embodiment, as shown in FIG. 35, notches (for example, notches 324b) are formed in side portions of respective free end portions 324a, 328a, and 329a of easily deformable parts 324, 328, and 329, and a part of the material forming joint parts 325 or link parts 315 penetrates each of the respective notches (for example, the notches 324b) in the easily deformable parts 324, 328, and 329. By virtue of the notches in the easily deformable part 324 or the link part 315 and those parts of the joint part 325 which are penetrating the notches, disconnection of the joint part from the easily deformable part or the connection part is restrained, thus constituting an example of a means for restraining disconnection.

The respective free ends of the easily deformable parts 324, 328, and 329 joined to the joint parts 325 or the link parts 315, preferably, have their corner portions rounded.

The surface parts of the easily deformable part which are covered with the joint part 325 and the link part 315 are preferably surface treated, for enhancing adhesion thereof to the material forming the joint parts. The surface treatment is preferably carried out by a method in which the relevant surface is coated with a high-affinity material serving as a primer. As the surface treatment method, the above-mentioned ones can be used suitably.

In the stent 310 in this embodiment, as shown in FIG. 34, the adjacent annular members 314 are interconnected by the link part(s) 315. Specifically, the easily deformable parts 327 having parts to be linked to the link part 315 are interconnected by the link part 315. The link parts 315 are formed of a biodegradable material. This helps ensure that the stent has good deformability in the axial direction.

In the stent 310 according to this embodiment, the annular components in one annular member 314 are so configured that one annular component 312b of the adjacent annular components is located on the side of a proximal end (is set back proximally) in the axial direction of the stent 310 relative to the other annular component 312a. In other words, end portions of one annular member 314 project in a zigzag fashion. Specifically, one annular member 314 composes a plurality of annular components 312a which have end portions projecting to the distal end side of the stent, and a plurality of annular components 312b which have end portions projecting to the proximal end side of the stent and which are each located between the annular components projecting to the distal end side. In the stent 310 in this embodiment, each annular member 314 has an even number of the annular components; therefore, every pair of the adjacent components 312a and 312b are staggered in position from each other in the axial direction of the stent 310. For stabilizing such a zigzag form, it is preferable to provide an even number of the annular components.

Further, in each annular member 314, the adjacent annular components 312 (312a and 312b) are interconnected by a short connection part 313 in the vicinity of the centers of side portions of the annular components. In other words, the connection parts 313 interconnect the annular components 312

(312a and 312b) in the circumferential direction of the stent, to form the annular member. The connection parts 313 are substantially not changed even when the stent 310 is expanded. Therefore, the force at the time of expansion is liable to be exerted principally on the center of each annular component, so that the annular components can be expanded (deformed) relatively evenly. In addition, the connection parts are portions which show a small deformation amount when the stent is compressed or expanded.

Furthermore, in this stent 310, the connection parts 313 are substantially parallel to the center axis of the stent 310. Therefore, there is little limitation on the diameter reduction of the connection parts when the stent 310 is compressed, so that the stent 310 can be made smaller in diameter accordingly.

The number of the annular components 312 is not limited to 12, and is preferably not less than 4. Particularly, the number of the annular components 312 is preferably 6 to 20. Moreover, the number of the annular components 312 is preferably an even number as mentioned above. The shape of the annular components is preferably such that the annular components become substantially elliptic or substantially rhombic when the stent is expanded. However, other polygonal shapes may also be adopted, for example, a rectangle elongated in the axial direction, a hexagon, an octagon, or the like.

The connection part 313 of the annular member 314 and the connection part 313 of the adjacent annular member 314 are interconnected by link parts 315 which is comparatively long (as compared with the connection part). Specifically, the annular member 314a and the axially adjacent annular member 314b are interconnected by the link parts 315 interconnecting the connection parts 313. The annular member 314b and the axially adjacent annular member 314c are interconnected by the link parts 315 interconnecting the connection parts 313. The annular member 314c and the axially adjacent annular member 314d are interconnected by the link parts 315 interconnecting the connection parts 313. The annular member 314d and the axially adjacent annular member 314e are interconnected by the link parts 315 interconnecting the connection parts 313. The annular member 314e and the axially adjacent annular member 314f are interconnected by the link parts 315 interconnecting the connection parts 313. In the stent in this embodiment, the link parts 315 are so provided as to interconnect the axially adjacent annular members 314 at a plurality of positions. The link part may be so provided as to interconnect the adjacent annular members at only one position. The number of the link parts provided between the adjacent annular members is preferably 1 to 5, particularly 1 to 3.

In addition, in the stent 310 according to this embodiment, when viewed along the axial direction, the annular components 312 are so aligned that they are arrayed substantially rectilinearly in relation to the axial direction of the stent 310. Specifically, in the stent 310 in this embodiment, all the annular components adjacent in the axial direction are so aligned that they are arrayed substantially rectilinearly in relation to the axial direction of the stent 310. In addition, all the link parts 315 are also substantially parallel to the axial direction of the stent 310. Therefore, torsion would not easily be generated at the link parts 315. Further, all the connection parts 313 are parallel to the axial direction of the stent 310 when the stent 310 is not expanded. Accordingly, torsion would not easily be generated at the connection parts 315, either.

The diameter of the stent when not expanded is preferably about 0.8 to 1.8 mm, more preferably 0.9 to 1.6 mm. The length of the stent when not expanded is preferably about 8 to 40 mm. The length of one annular member 314 in the axial direction is preferably about 1.0 to 2.5 mm. The stent according is not limited to the balloon-expandable stent as above-described, and may be a self-expandable stent. In the case where the stent disclosed here is applied to a self-expandable stent, the above-described stent forms can be used.

In the case of the self-expandable stent, the material constituting the easily deformable parts is preferably a superelastic metal. As the superelastic metal, the above-mentioned ones can be used.

A stent according to other embodiments is illustrated in FIGS. 36-42. The stent 401 here is a stent in which a plurality of annular members 402 composed of a linear component in an annular form are arrayed in the axial direction of the stent 401, with the adjacent annular members 402 being interconnected by a link part or parts 403. Each of the annular members 402 is composed of discontinuous parts 402a provided in the annular component, and joint parts 423 joining the discontinuous parts 402a. The joint parts 423 are formed of a biodegradable material, and degradation (decomposition) of the joint parts 423 results in disconnecting the annular members 402 at the discontinuous parts 402a.

The stent 401 in this embodiment is a so-called balloon-expandable stent, that is, a stent which is formed to be a substantially tubular body, which has a diameter suitable for insertion into a lumen in vivo, and which can be expanded when a force dilating in the radial direction from the inside of the tubular body is exerted thereon. Incidentally, the stent in this embodiment is not limited to the balloon-expandable stent.

Figure 36:
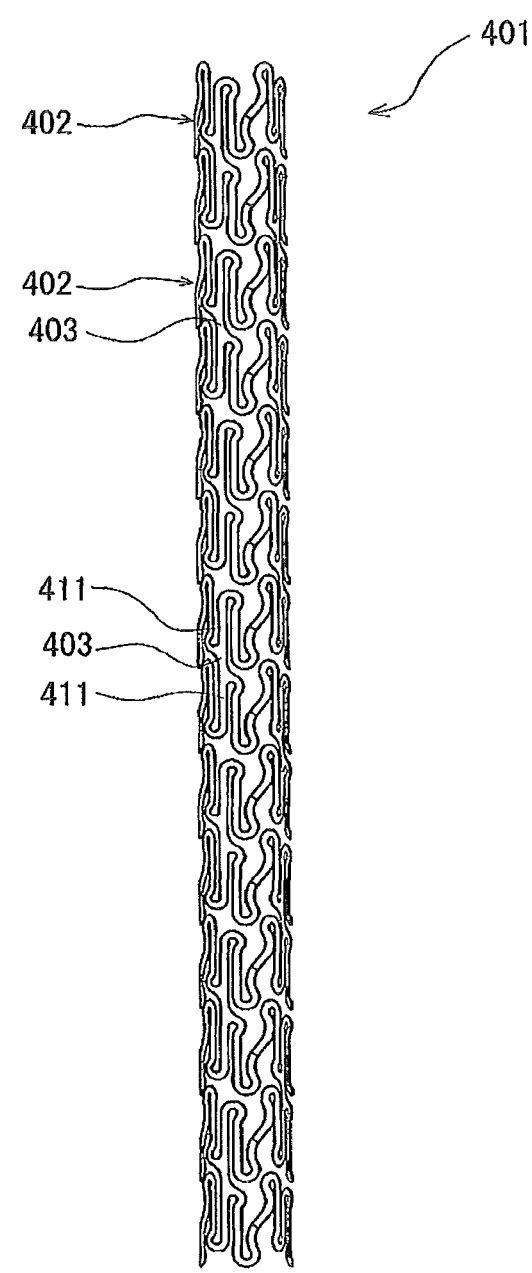
FIG. 36 is a front view of a stent according to a still further embodiment disclosed here.
Figure 37:
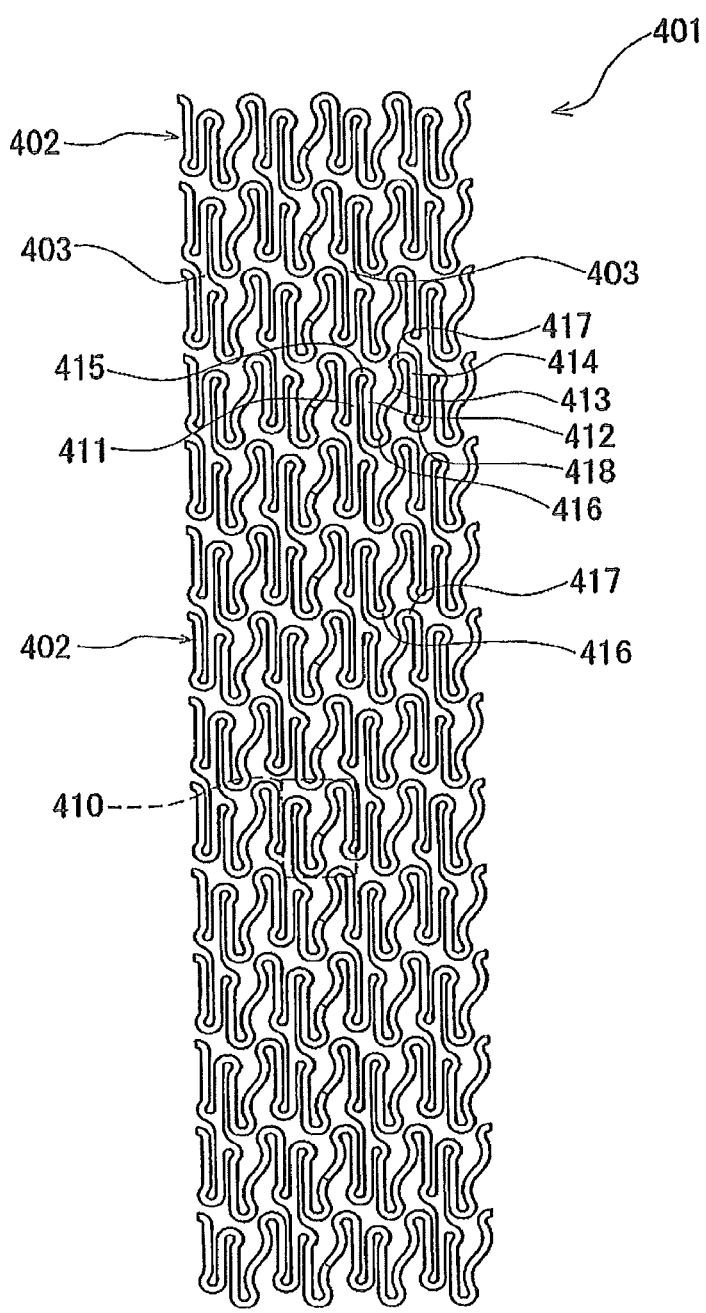
FIG. 37 is a developmental view of the stent shown in FIG. 36.
Figure 38:
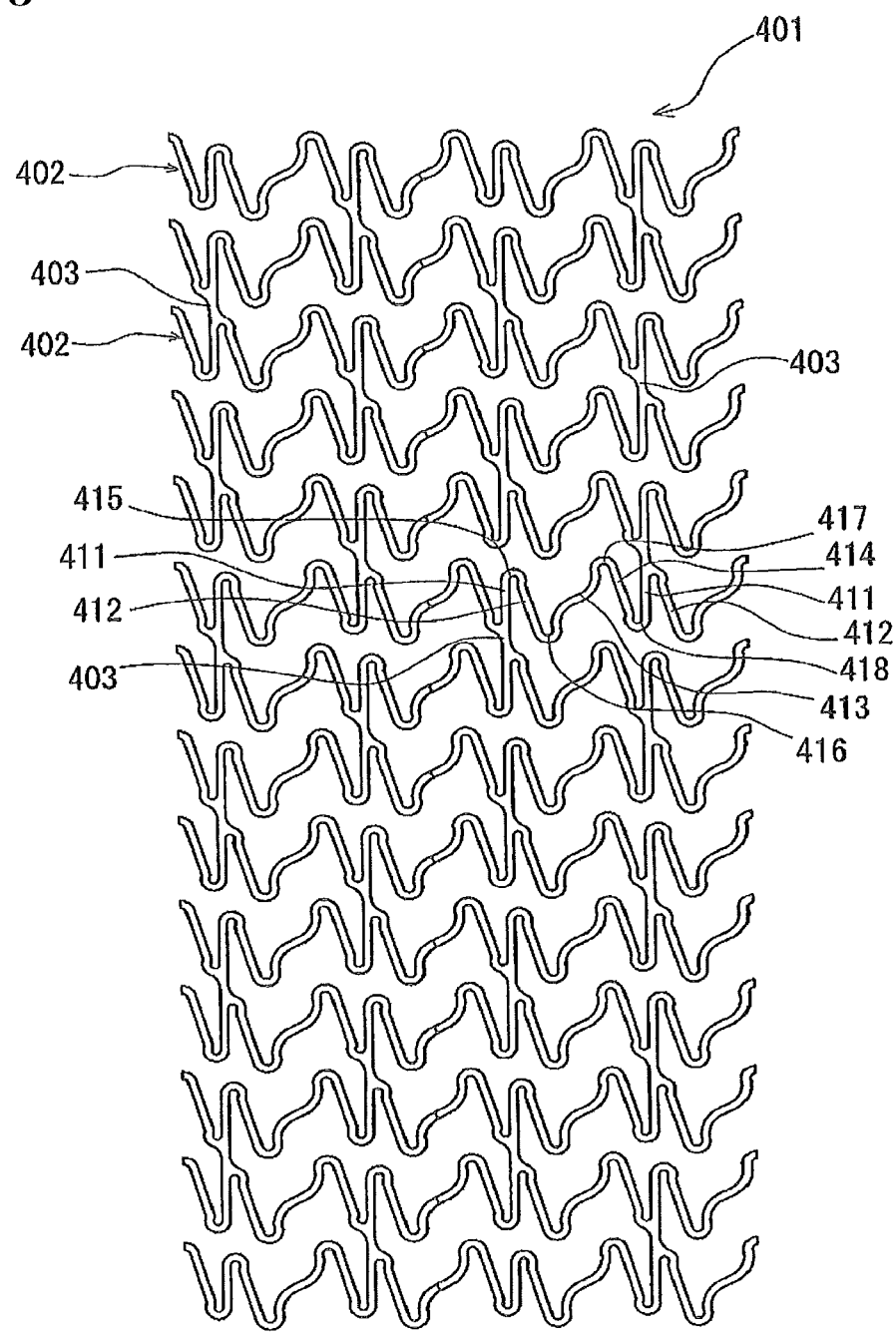
FIG. 38 is a developmental view of the stent illustrated in FIG. 36 when the stent is expanded.

As shown in FIGS. 36 to 38, the stent 401 according to this embodiment has a configuration in which a plurality of wavy-linear annular members 402 are so arrayed as to be adjacent to one another in the axial direction of the stent 401 and are interconnected.

The number of the wavy-linear annular members 402 constituting the stent 401 is 14 in the embodiment shown in FIGS. 36, 37 and 38. The number of the wavy-linear annular members 402 differs depending on the length of the stent, and is preferably 4 to 50, particularly 10 to 35.

Each of the wavy-linear annular members 402 is composed of an endless linear component (specifically, wavy-linear member) which has a plurality of one-end-side bent portions 415 and 417 having vertices on one end side in the axial direction of the stent 401, and a plurality of the other-end-side bent portions 416 and 418 having vertices on the other end side in the axial direction of the stent 401, and which is continuous in an annular form.

The material forming the stent is preferably a material which has a certain degree of biocompatibility. Examples of such a material include stainless steels, tantalum and tantalum alloys, platinum and platinum alloys, gold and gold alloys, cobalt-based alloys, cobalt-chromium alloys, titanium alloys, niobium alloys and the like. After the material is formed into a stent shape, the formed body may be plated with a noble metal (gold, or platinum). Among the stainless steels, preferred is SUS316L, which is the highest in corrosion resistance.

Each of the annular members 402 has discontinuous parts 402a provided in the linear component, and joint parts 423 which join the discontinuous parts 402a. The joint parts 423 are formed of a biodegradable material, and degradation (decomposition) of the joint parts 423 results in disconnecting the annular members 402 at the discontinuous parts 402a.

In addition, in the stent according to this embodiment, the discontinuous parts 402a are provided at linear component parts where the deformation amount at the time of compression or expansion of the stent is relatively small. In the stent in this embodiment, the joint parts 423 joining the discontinuous parts 402a are formed at parts where the stress exerted at the time of compression or expansion of the stent 401 is low. As the parts where the deformation amount is small and the parts where the stress exerted is low, there may be considered those parts which are not bent, rectilinear parts, those portions of the rectilinear parts which are enlarged in line width, of the linear component.

Figure 41:
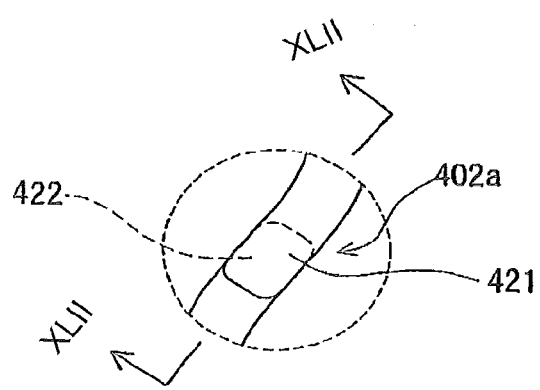
FIG. 41 is an enlarged view of the circled portion (vicinity of a joint) of the stent shown in FIG. 40.
Figure 42:
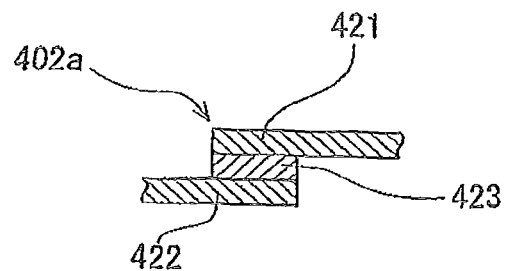
FIG. 42 is an enlarged cross-sectional view taken along the section line XLII-XLII in FIG. 41.

As shown in FIGS. 41 and 42, at the parts of the discontinuous parts 402a, the linear component is discontinuous, and a first free end portion 421 and a second free end portion 422 of the linear component are overlapping with each other. In the stent 401 in this embodiment, the discontinuous part 402a is joined by the joint part 423. The joint part 423 is formed at inner surface parts where the two free end portions of the linear component overlap with each other, specifically, between the first free end portion 421 and the second free end portion 422. In addition, corners of the two free end portions 421 and 422 in the linear component have their edges chamfered.

Further, the joint parts are composed of a biodegradable material, and degradation (decomposition) of the joint parts 423 results in disconnecting the annular members 402 at the discontinuous parts 402a.

As the biodegradable material, a biodegradable metal or a biodegradable polymer is preferably used. In addition, the biodegradable material preferably has a property for adhesion to the material constituting the stent.

As the biodegradable metal, the above-mentioned ones can be used. As the biodegradable polymer, the above-mentioned ones can be used. In addition, those surface portions of the discontinuous parts which are joined by the joint part may be wholly or partly pretreated, for enhancing adhesion thereof to the material constituting the joint part. The pretreatment is preferably carried out by a method in which the relevant surface is coated with a high-affinity material serving as a primer. As the primer material, the above-mentioned ones can be used.

Besides, a physiologically active substance may be contained, in a releasable manner, in the material forming the joint parts. As the physiologically active substance, the above-mentioned ones can be used.

In addition, the forms of the discontinuous part and the joint part in the stent are not limited to the above-mentioned.

Figure 43:
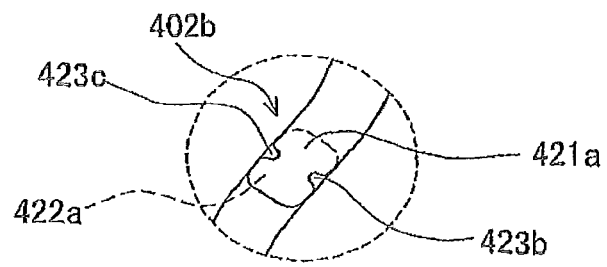
FIG. 43 is an enlarged view of the vicinity of a joint in a stent according to another embodiment.
Figure 44:
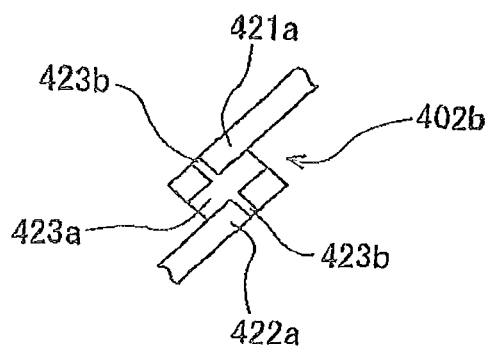
FIG. 44 is a side view of the vicinity of the joint shown in FIG. 43.

For example, the forms may be ones as shown in FIGS. 43 and 44. A discontinuous part 402b in this embodiment has a configuration in which, like in the above-mentioned discontinuous part, the linear component is discontinuous at the part of the discontinuous part 402b, and a first free end portion 421a and a second free end portion 422a in the linear component overlap with each other. In the stent 401 in this embodiment, the discontinuous part 402a is joined by a joint part 423a. The joint part 423a is formed at inner surface portions where the two free end portions of the linear component overlap with each other, specifically, between the first free end portion 421a and the second free end portion 422a. Further, the two free end portions 421a and 422a of the linear component are provided with notches in side portions thereof, and the joint part 423a has projected portions 423b and 423c which penetrate the notches. The projected portions 423b and 423c formed on the joint part 423a and the notches formed in the free end portions 421a and 422a constitute means for restraining disconnection of the free end portions of the linear component from the joint part. Furthermore, they exhibit a function of holding the dilation-maintaining force in the joint portions.

In the stent in this embodiment, also, corners of the two free end portions 421a and 422a in the linear component have their edges chamfered. Further, also at the notches provided in side portions of the two free end portions 421a and 422a of the linear component, corners have their edges chamfered.

Figure 45:
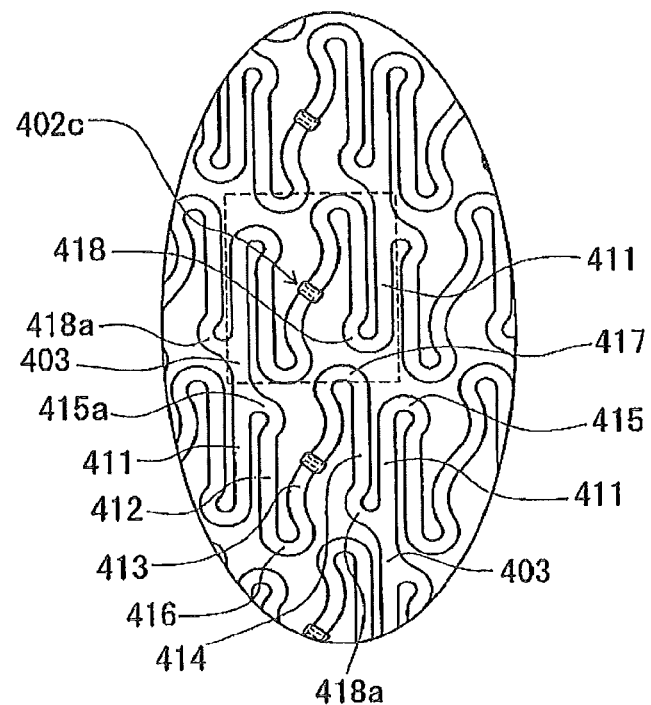
FIG. 45 is an enlarged view of a portion of the stent according to a further embodiment disclosed here.
Figure 46:
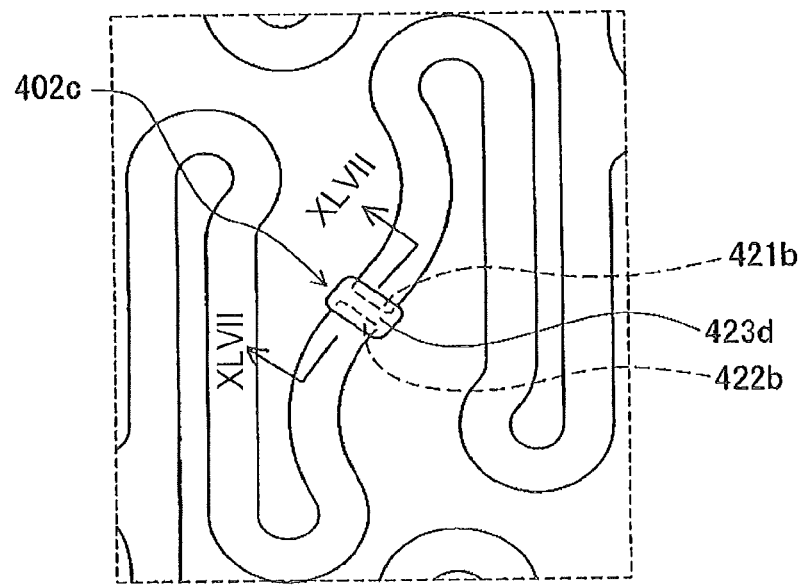
FIG. 46 is an enlarged view of the dotted-outline portion (vicinity of a joint) of the stent shown in FIG. 45.
Figure 47:
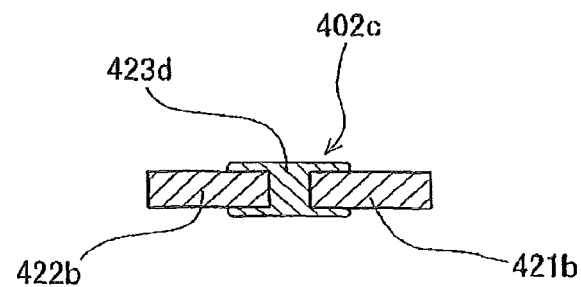
FIG. 47 is an enlarged cross-sectional view taken along the section line XLVII-XLVII in FIG. 46.

In addition, the forms of the discontinuous part and the joint part may be different such as the ones shown in FIGS. 45-47. A discontinuous part 402c in this embodiment has a configuration in which the linear component is discontinuous at the part of the discontinuous part 402c, and a first free end portion 421b and a second free end portion 422b in the linear component are slightly spaced from each other, leaving a gap therebetween.

In the stent in this embodiment, the discontinuous part 402c is joined by a joint part 423d. The joint part 423d is so formed as to interjoint (connect) the spaced parts of the two free end portions in the linear component. In the stent according to this embodiment, corners of the two free ends 421b and 422b of the linear component have their edges chamfered.

Figure 48:
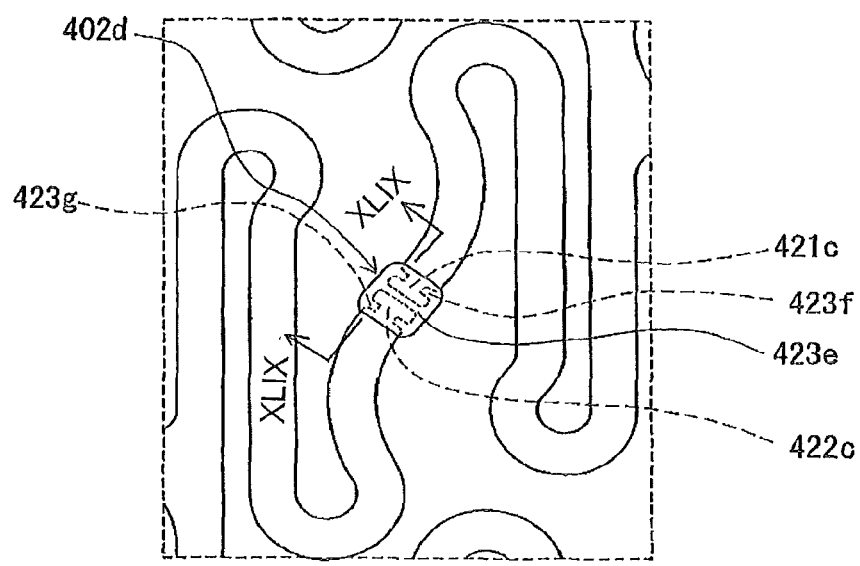
FIG. 48 is an enlarged view of the vicinity of a joint in a stent according to yet another embodiment.
Figure 49:
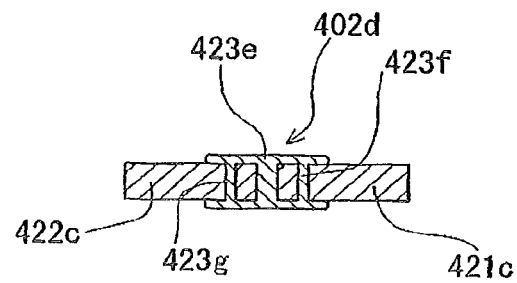
FIG. 49 is an enlarged sectional view taken along the section line XLIX-XLIX in FIG. 48.

In addition, other forms for the discontinuous part and the joint part in the stent may be as shown in FIGS. 48 and 49. A discontinuous part 402d in this embodiment has a configuration wherein the linear component is discontinuous at the part of each discontinuous part 402d, and a first free end portion 421c and a second free end portion 422c of the linear component are slightly spaced from each other, leaving a gap therebetween.

In the stent according to this embodiment, the discontinuous part 402d is joined by a joint part 423e. The joint part 423e is so formed as to join the spaced parts of the two free end portions in the linear component. In the stent in this embodiment, also, corners of the two free ends 421c and 422c in the linear component have their edges chamfered.

In addition, notches are provided in side portions of the two free end portions 421c and 422c in the linear component, and the joint part 423e has projected portions 423f and 423g which penetrate the notches. The projected portions 423f and 423g formed on the joint part 423e and the notches formed in the free end portions 421c and 422c constitute means for restraining disconnection of the free end portions of the linear component from the joint part. Further, they exhibit a function of holding a dilation-maintaining force at the joint portion.

In the stent 401 in the embodiment as above-described, the positions where the discontinuous parts and the joint parts are formed in the annular members 402 are aligned substantially rectilinearly in the axial direction of the stent 401, as shown in FIGS. 36-38.

Figure 50:
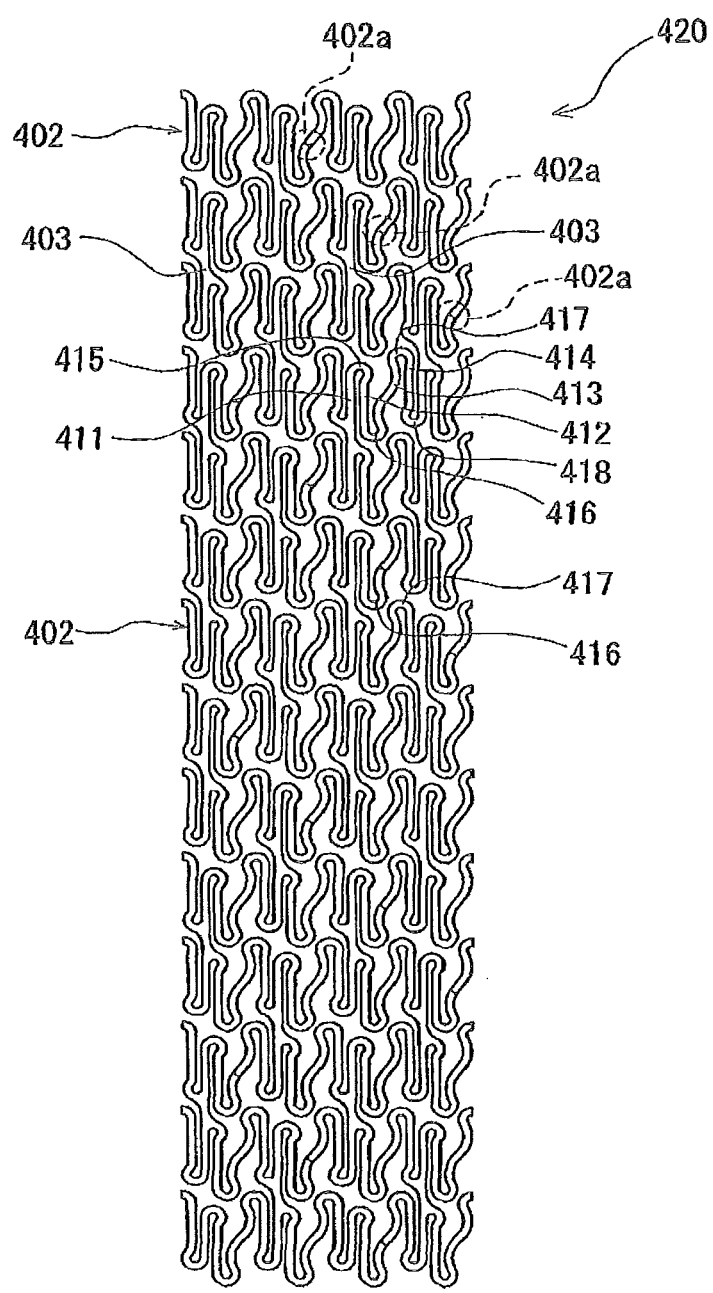
FIG. 50 is a developmental view of a stent according to a yet further disclosed embodiment.

However, the positions where the discontinuous part and the joint part are formed in the annular components 402 are not limited to the just-mentioned. The positions may be so set as to be arranged spirally in relation to the axial direction of the stent, as in the case of a stent 420 in an embodiment shown in FIG. 50. Further, the positions may be so set that they do not have any regularity in relation to the axial direction of the stent.

In addition, the discontinuous parts in the stent are preferably provided in the smallest number that enables the annular member to be disconnected. Therefore, it is preferable that only one discontinuous part is provided in each annular member, as in the stent 401 in the above-described embodiment. This helps ensure that a sufficient shape preservation property to the stent form is secured even after degradation of the joint parts.

In the stent 401 in this embodiment, one-end-side bent portions 415 and 417 and the other-end-side bent portions 416 and 418 in the annular member 402 are formed alternately, and the respective numbers of the two kinds of bent portions are the same.

The total number of one-end-side bent portions 415 and one-end-side bent portions 417 in one wavy-linear annular member 402 is 8 in the embodiments shown in FIGS. 36-49. Similarly, the total number of the other-end-side bent portion 416 and the other-end-side bent portions 418 in one wavy-linear annular member 402 is also 8. The number of one-end-side bent portions and the other-end-side bent portions in the wavy-linear annular member 402 is preferably 4 to 12, particularly 6 to 10. The length of the wavy-linear annular member 402 in the axial direction is preferably 0.5 to 2.0 mm, particularly 0.9 to 1.5 mm.

Figure 39:
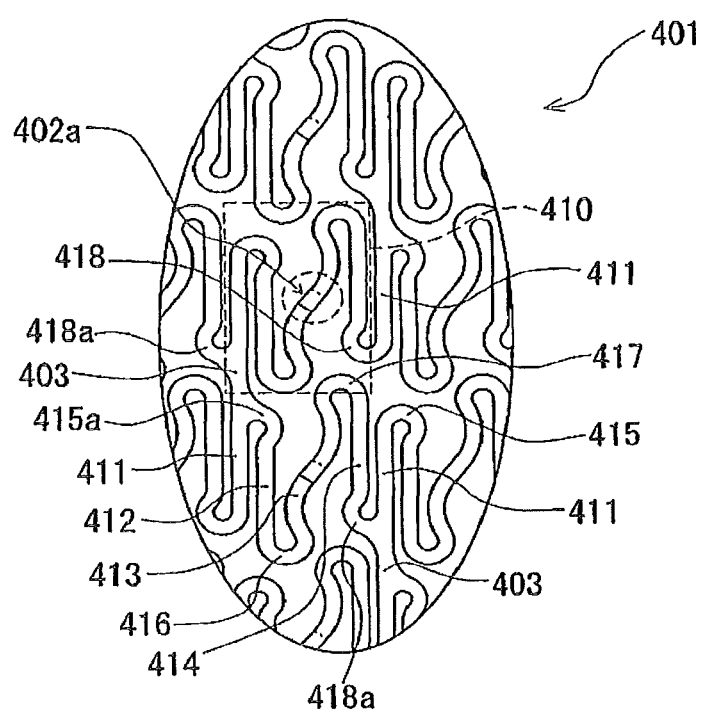
FIG. 39 is an enlarged view of a portion of the stent shown in FIG. 37.
Figure 40:
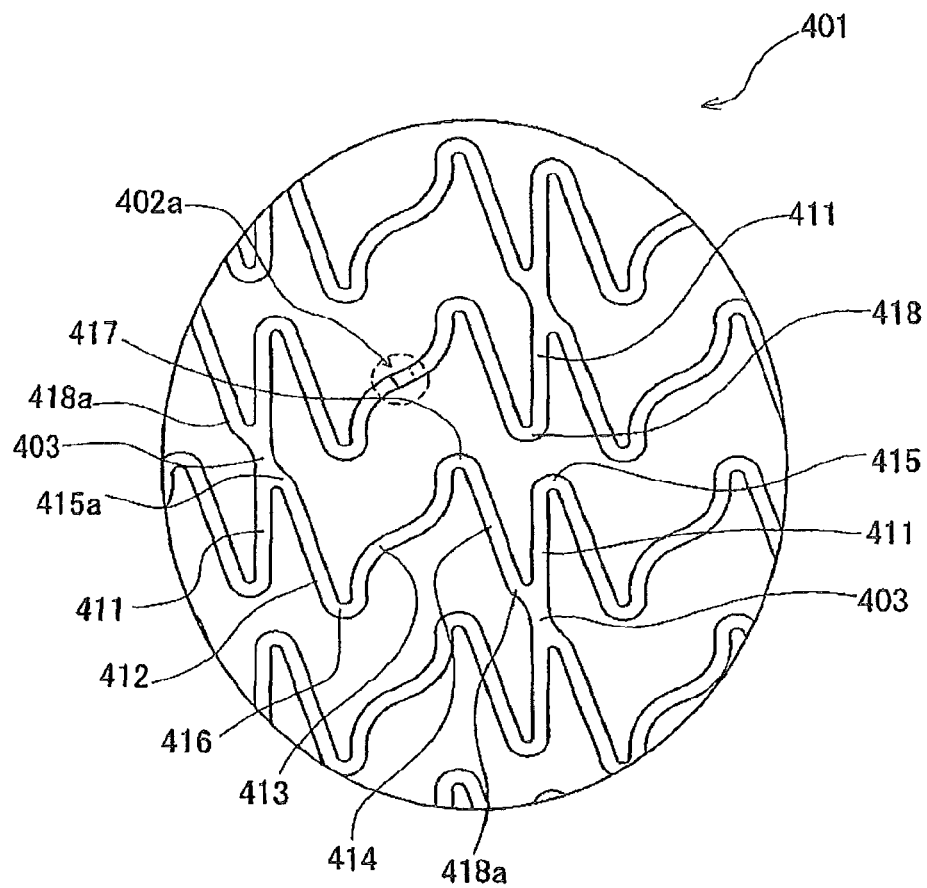
FIG. 40 is an enlarged view of a portion of the stent shown in FIG. 38.

As shown in FIGS. 36-40, the wavy-linear annular member 402 has a plurality of deformed-M-shaped linear portions 410 arranged to be continuous with one another. Each of the deformed-M-shaped linear portions 410 composes four linear portions, namely a first inclined rectilinear portion 412 which is connected to one end of a parallel rectilinear portion 411 through the bent portion 415 (415*a*) and which is inclined at a predetermined angle against the center axis of the stent 401 at least when the stent 401 is expanded (FIG. 40), an inclined linear portion (in this embodiment, an inclined curved-line portion) 413 which is connected to one end of the first inclined rectilinear portion 412 through the bent portion 416 and which extends at an inclination of a predetermined angle relative to the center axis of the stent, and a second inclined rectilinear portion 414 which is connected to one end of the inclined curved-line portion 413 through the bent portion 417 and which is inclined at a predetermined angle against the center axis of the stent 401 at least when the stent 401 is expanded (FIG. 40). The adjacent deformed-M-shaped linear portions 410 are interconnected by the bent portion 418 (418*a*) which interconnects one end of the second inclined rectilinear portion 414 and the other end of the parallel rectilinear portion 411, to form the wavy-linear annular member 402 which is endless (looped). This helps ensure that shortening of the axial length of the wavy-linear annular members 402 at the time of expansion of the stent is restrained, and a sufficient dilation-holding force is imparted to the wavy-linear annular member 402.

Particularly, in the stent 401 according to this embodiment, as shown in FIG. 37 (before expansion of the stent, upon compression of the stent) and FIG. 38 (upon production of the stent, and also upon expansion of the stent), the wavy-linear annular member 402 composes a plurality of the deformed-M-shaped linear portions arranged to be continuous with one another. Each of the deformed-M-shaped linear portions is composed of the four linear portions, that is, the first inclined rectilinear portion 412 which is connected to one end of the parallel rectilinear portion 411 through the bent portion 415 (415*a*) and is parallel (inclusive of substantially parallel) to the center axis of the stent 401 (before expansion of the stent) and which becomes inclined at a predetermined angle upon expansion of the stent, the inclined curved-line portion 413 which is connected to one end of the first inclined rectilinear portion 412 through the bent portion 416 and which extends slantly at a predetermined angle against the center axis of the stent, and the second inclined rectilinear portion 414 which is connected to one end of the inclined curved-line portion 413 through the bent portion 417 and is substantially parallel to the center axis of the stent 401 (before expansion of the stent) and which becomes inclined at a predetermined angle upon expansion of the stent 401. In short, the first inclined rectilinear portion 412 and the second inclined rectilinear portion 414 are substantially parallel to the center axis of the stent 401 before expansion of the stent, that is, when the stent is in a compressed state. Therefore, the outside diameter of the stent when compressed can be made smaller accordingly.

Specifically, as shown in FIG. 39, the first inclined rectilinear portion 412 and the second inclined rectilinear portion 414 are parallel (inclusive of substantially parallel) to the center axis of the stent before expansion of the stent; when the stent is expanded, as shown in FIG. 40, they extend in an inclined manner in the same direction in relation to the center axis of the stent. Particularly, in the stent 401 according to this embodiment, upon expansion of the stent, the first inclined rectilinear portion 412 and the second inclined rectilinear portion 414 extend at an incline relative to the center axis of the stent and parallel (inclusive of substantially parallel) to each other. On the other hand, the inclined curved-line portion 413 extends at an incline relative to the center axis of the stent even before expansion of the stent, and, upon expansion of the stent, the inclined curved-line portion 413 extends at an incline relative to the center axis of the stent in a direction different from the direction in which the first inclined rectilinear portion 412 and the second inclined rectilinear portion 414 extend.

The numbers of one-end-side bent portions and the other-end-side bent portions in the deformed-M-shaped linear portion 410 are both 2, in the embodiment as shown in FIGS. 36-40. The spacing between the other-end-side bent portion 416 and one-end-side bent portion 417 in the direction orthogonal to the center axis of the stent 401 (in other words, the width of the deformed-M-shaped linear portion 410 at the inclined curved-line portion) is wider than the spacing between one-end-side bent portion 415 and the other-end-side bent portion 416 in the direction orthogonal to the center axis of the stent 401 (in other words, the width of the deformed-M-shaped linear portion 410 at the first inclined rectilinear portion), and the spacing between one-end-side bent portion 417 and the other-end-side bent portion 418 in the direction orthogonal to the center axis of the stent 401 (in other words, the width of the deformed-M-shaped linear portion 410 at the second inclined rectilinear portion). With the inclined curved-line portion 413 located in a large-width portion, a sufficient dilation-holding force is imparted to the wavy-linear annular member 402.

As shown in FIG. 38, in the wavy-linear annular member 402, the bent portion 417 located on one end side of the inclined curved-line portion 413 is projecting to one end side relative to the other one-end-side bent portion 415 (i.e., the bent portion 417 projects further than the bent portion 415). Similarly, in the wavy-linear annular member 402, the bent portion 416 located on the other end side of the inclined curved-line portion 413 is protruding to the other end side relative to the other other-end-side bent portion 418 (i.e., the bent portion 416 protrudes beyond the bent portion 418).

In the stent 401 in this embodiment, one wavy-linear annular member 402 is composed of four deformed-M-shaped linear portions 410. One wavy-linear annular member 402 is preferably composed of 3 to 5 deformed-M-shaped linear portions 410.

In the stent in a compressed state (FIGS. 36, 38 and 39), each wavy-linear annular member 402 is composed of a plurality of one-end-side bent portions 415 and 417 having vertices on one end side in the axial direction of the stent 401 and a plurality of the other-end-side bent portions 416 and 418 having vertices on the other end side in the axial direction of the stent 401. In addition, at least one vertex of one-end-side bent portion 417 of the wavy-linear annular member 402 slightly penetrates the space formed between the other-end-side bent portions of the axially adjacent wavy-linear annular member 402 on one side (i.e., at least one vertex of one-end-side bent portion 417 of the wavy-linear annular member 402 axially overlaps a part of the other-end-side bent portions of the axially adjacent wavy-linear annular member 402 on one side). Similarly, at least the vertex of the other-end-side bent portion 416 of the wavy-linear annular member 402 slightly penetrates the space formed between one-end-side bent portions of the adjacent wavy-linear annular member on the other side (i.e., at least the vertex of the other-end-side bent portion 416 of the wavy-linear annular member 402 axially overlaps a part of the one-end-side bent portions of the adjacent wavy-linear annular member on the other side). Therefore, the wavy-linear annular member 402 has a sufficient dilation-holding force when expanded.

In addition, the parallel rectilinear portion 411 is preferably shorter in line length than the first inclined rectilinear portion 412, the inclined curved-line portion 413 and the second inclined rectilinear portion 414. Setting the parallel rectilinear portion to be short makes it possible to enhance the dilation-holding force.

The bent portion 415 (415a) interconnecting one end of the parallel rectilinear portion 411 and the first inclined rectilinear portion 412 in the wavy-linear annular member 402 is preferably a swelled (enlarged) bent portion. This makes it possible to disperse the distortion upon expansion and thereby to secure a higher safety factor. Further, it is preferable that both the bent portion 415 (415a) interconnecting one end of the parallel rectilinear portion 411 and the first inclined rectilinear portion 412 and the bent portion 418 (418a) interconnecting the other end of the parallel rectilinear portion 411 and the second inclined rectilinear portion 414, in the wavy-linear annular member 402, are swelled (enlarged) bent portions. Such a configuration makes it possible to disperse the distortion upon expansion and thereby to secure a further higher safety factor. Furthermore, it is preferable that the other bent portions 416 and 417 are also swelled (enlarged) bent portions.

While it is preferable that the bent portions are swelled bent portions as above-mentioned, such a configuration is not absolutely necessary, and the bent portions need not be swelled. Where the bent portions are not swelled in shape, the outside diameter of the stent when compressed can be made relatively smaller, which is advantageous in inserting the stent into a small-diameter organ in vivo (e.g., a blood vessel).

The adjacent wavy-linear annular members 402 are interconnected by a connection part or parts 403. Particularly, in the stent 401 according to this embodiment, end portions of the parallel rectilinear portions 411 of the adjacent wavy-linear annular members 402 are close to each other and are interconnected by the short connection part 403. Therefore, the distance between the adjacent wavy-linear annular members 402 is short, whereby formation of low dilating force portions arising from the spacing between the adjacent wavy-linear annular members 402 is suppressed extremely.

In the stent 401 in this embodiment, as shown in FIGS. 36-40, the two parallel rectilinear portions 411 interconnected by the connection part 403 are substantially rectilinear in shape. This makes it possible to inhibit or prevent shortening of the stent between the adjacent wavy-linear annular members upon expansion of the stent. In this stent 401, a plurality of the connection parts 403 are provided for interconnecting the adjacent wavy-linear annular members 402. Therefore, the adjacent wavy-linear annular members would not be mutually spaced apart needlessly, and the stent as a whole exhibits a sufficient dilating force. Specifically, as shown in FIGS. 38 and 40, the adjacent wavy-linear annular members 402 are in a condition where both the bent portion 418a interconnecting the other end of the parallel rectilinear portion 411 and the second inclined rectilinear portion 414 and the bent portion 415a interconnecting one end of the parallel rectilinear portion 411 and the first inclined rectilinear portion 412 are interconnected by the short connection part 403. The two parallel rectilinear portions 411 thus interconnected by the connection part 403 are continuous and rectilinear in shape.

In addition, in this embodiment, there is no area in which more than two (namely, at least three) parallel rectilinear portions 411 in series along the axial direction are interconnected and united by the connection part(s). That is, only two parallel rectilinear portions 411 are interconnected by the connection part 403, and there is no area where three parallel rectilinear portions 411 are united. Therefore, it is possible to suppress the generation of a phenomenon in which a load exerted when one wavy-linear annular member is changed so as to follow up to a deformation of a blood vessel is transmitted directly (or rectilinearly) to non-adjacent wavy-linear annular members. Therefore, independent dilating (expanding) functions of the individual wavy-linear annular members can be exhibited.

The connection parts 411 adjacent to each other in the axial direction of the stent 401 are staggered in position from each other in the direction orthogonal to the center axis of the stent. Therefore, a situation in which more than two (at least three) parallel rectilinear portions 411 are interconnected by the connection part(s) is obviated. Accordingly, it is possible to suppress the generation of a phenomenon in which a load exerted when one wavy-linear annular member is changed so as to follow up to a deformation of a blood vessel is transmitted directly (or rectilinearly) to non-adjacent wavy-linear annular members. Thus, independent dilating (expanding) functions of the individual wavy-linear annular members can be exhibited.

In addition, the stent 401 is composed of a plurality of the connection parts 403 for interconnecting the adjacent wavy-linear annular members 402. Therefore, the adjacent wavy-linear annular members would not be mutually spaced apart needlessly, and the stent as a whole exhibits a sufficient dilating force. Incidentally, a configuration in which only one connection part 403 is provided between the adjacent wavy-linear annular members may also be adopted. The length of the connection part 403 in the axial direction of the stent 401 is preferably about 1.0 mm or below, particularly in the range of 0.1 to 0.4 mm.

In this stent 401, two connection parts 403 are provided for interconnecting the adjacent wavy-linear annular members 402, and the two connection parts are arranged at diametrically opposite positions. In addition, the connection parts 403 are so arranged as not to be continuous along the axial direction of the stent 401. Specifically, in the stent 401 in this embodiment, as shown in FIGS. 36-40, the two connection parts 403 are arranged at diametrically opposite positions, while the two connection parts 403 adjacent to the above-mentioned connection parts 403 in the axial direction are arranged diametrically opposite to each other and are circumferentially deviated or shifted from the above-mentioned connection parts by about 90° around the center axis of the stent 401.

The stent 401 is formed in the state corresponding to the developmental view in FIG. 38, being larger in outside diameter than in the state shown in FIGS. 36 and 37, and thereafter mounted, through compression, onto a dilatable balloon of a device having the balloon. Later, the stent 401 is enlarged in diameter to a state of being further greater in outside diameter than in the state of FIG. 38.

The diameter of the stent when not expanded is preferably about 0.8 to 1.8 mm, and more preferably 0.9 to 1.6 mm. The length of the stent when not expanded is preferably about 8 to 40 mm. The length of one wavy-linear annular member 402 is preferably about 1.0 to 2.5 mm.

The form of the stent is not limited to the one that is composed of the wavy-linear annular members as above-described. For example, a stent 430 as shown in FIGS. 51-54 may also be adopted. The stent 430 according to this embodiment is a stent which is formed to be a substantially tubular body, which has a diameter suitable for insertion in vivo, and which can be expanded when a force dilating radially outward from the inside of the tubular body is exerted thereon. The stent 430 is composed of annular members 434a-434f in each of which a plurality of annular components 432 each elongated in the axial direction of the stent, having an opening in a central portion thereof and being in a collapsed form are arranged so as to surround the center axis of the stent 430, with the adjacent annular components 432 (432a, 432b) being interconnected at a connection part 403 (433a, 433b). The plurality of the annular members 434 (434a, 434b, 434c, 434d, 434e, and 434f) are arrayed in the axial direction of the stent. Further, the connection part(s) 433 (433b) of each of the annular members 434 and the connection part(s) 433 (433b) of the axially adjacent annular member 434 are interconnected by a link part or parts 435 at least at one position. Furthermore, the annular components 432 in the annular members 434 (434a, 434b, 434c, 434d, 434e, and 434f) are so configured that one annular component 432b of the adjacent annular components is located on the side of a proximal end (set back proximally) in the axial direction of the stent 430 relative to the other annular component 432a. End portions of each annular member 434 are projecting in a zigzag fashion, and the end portions projecting in the zigzag fashion in each annular member 434 penetrate the adjacent annular member. In addition, the connection parts 433 in each annular member 434 are substantially parallel to the center axis of the stent 430.

Figure 53:
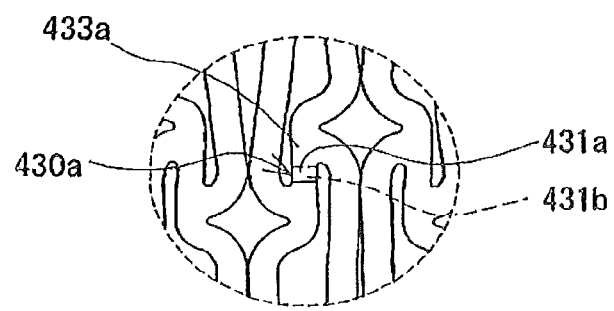
FIG. 53 is an enlarged view of a portion of (the vicinity of a joint) the stent shown in FIG. 52.
Figure 54:
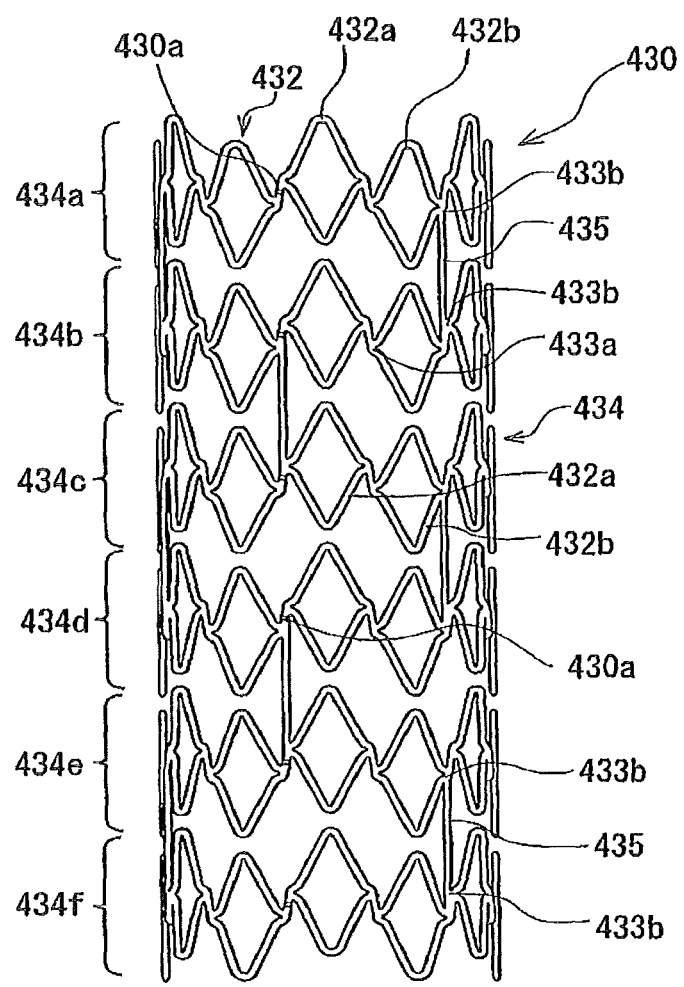
FIG. 54 is a front view of the stent of FIG. 52 when the stent is expanded.

One connection part 433, which is a linear component in each annular member 434, is provided with a discontinuous part 430a and a joint part for joining the discontinuous part 430a. The joint parts are formed of a biodegradable material, and degradation (decomposition) of the joint parts results in disconnecting each annular member 434 at the discontinuous part 430a. In the stent 430 in this embodiment, the configurations of the discontinuous part 430a and the joint part joining the discontinuous part 430a are the same as those of the discontinuous part 402a and the joint part 423 in the above-described stent 401. Specifically, as shown in FIG. 53, the linear component is discontinuous at the discontinuous part 430a, and a first free end portion 431a and a second free end portion 431b of the linear components are overlapping with each other. The discontinuous part 430a is joined by the joint part. The joint part is formed at inner surface portions where the two free end portions of the linear components overlap with each other, specifically, between the first free end portion 431a and the second free end portion 431b. In addition, corners of the two free end portions 431a and 431b of the linear component have their edges chamfered.

The configuration of the discontinuous part 430a and the joint part joining the discontinuous part 430a can be any of the types of configurations above-described. Particularly, it is preferable to provide means for restraining disconnection of the free end portions of the linear components from the joint part.

Figure 55:
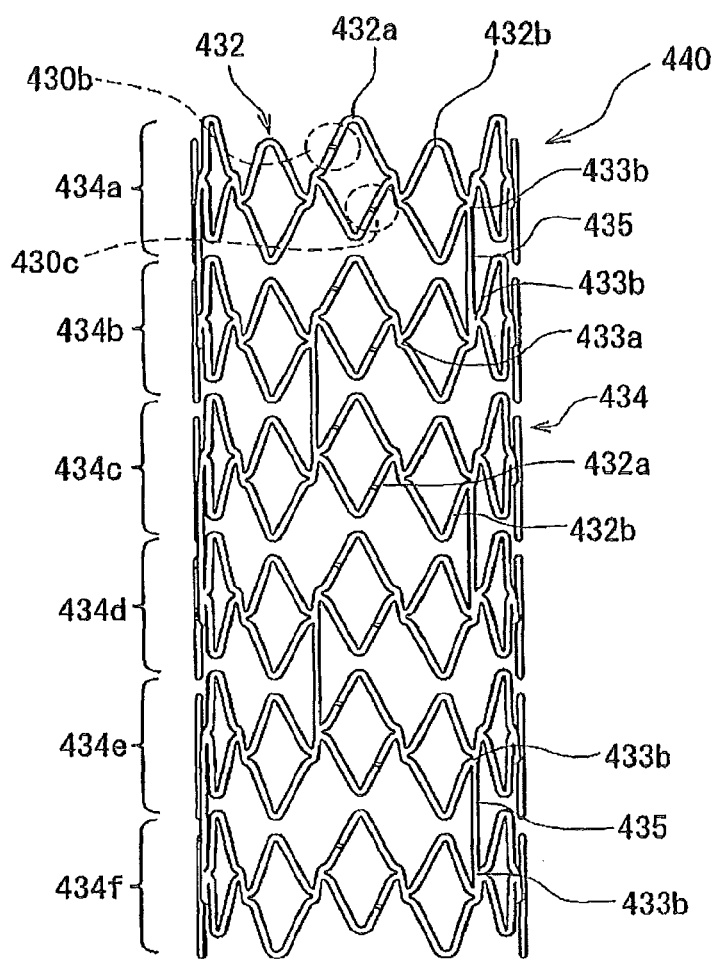
FIG. 55 is a front view of a stent according to a still further disclosed embodiment.

In addition, the portion where the discontinuous part and the joint part are formed is not limited to the connection part 433 in the annular member 434, and may be set at an annular component 432 as in a stent 440 in an embodiment shown in FIG. 55. In this case, in order to disconnect the annular members 434 by degradation (decomposition) of the joint parts, both of the linear component forming a peak portion and the linear component forming a valley portion have to be provided respectively with discontinuous parts 430b and 430c and the joint parts. In the stent 440 according to this embodiment, the annular member 434 has two discontinuous parts and two joint parts for disconnecting the annular member 434.

Figure 56:
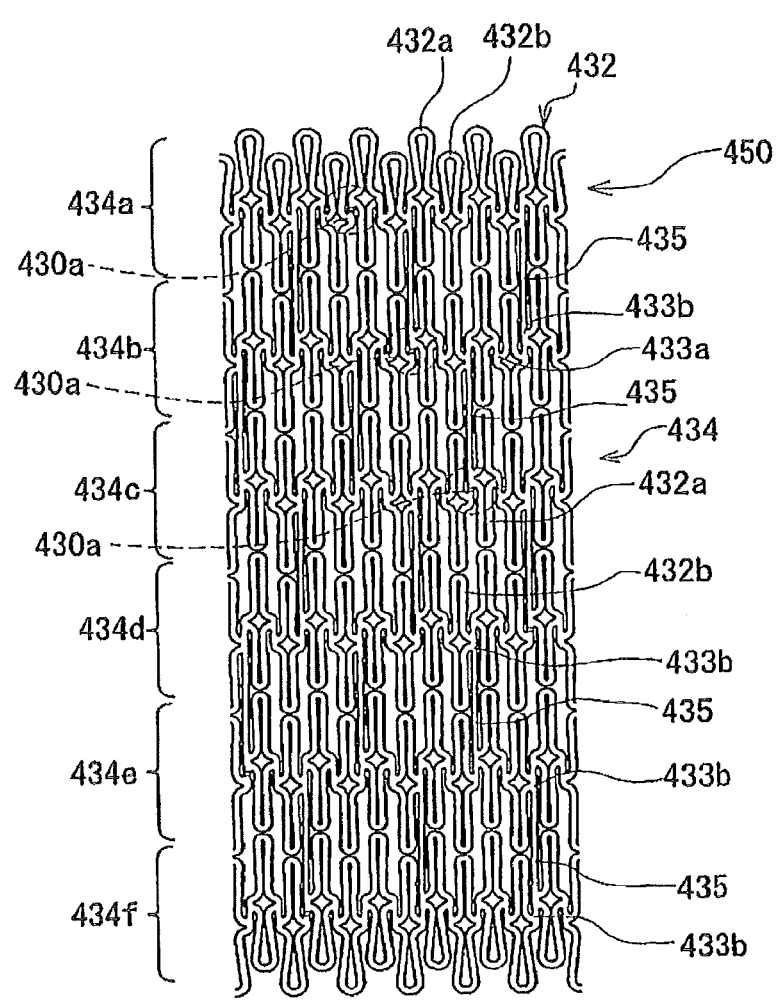
FIG. 56 is a developmental view of a stent according to another disclosed embodiment.

In the above-mentioned embodiment of the stent 430, the positions where the discontinuous parts and the joint parts in the annular members 434 are formed are aligned substantially rectilinearly along the axial direction of the stent 430, as shown in FIGS. 51-54. The positions where the discontinuous parts and the joint parts in the annular members 434 are formed are not limited to those in such a configuration as above. The positions may be arranged in a spiral pattern in relation to the axial direction of the stent, as in a stent 450 in an embodiment shown in FIG. 56. Further, the positions may be so arranged as not to have any regularity in relation to the axial direction of the stent.

The stent 430 in this embodiment is a tubular body configured by interconnecting a multiplicity of the annular members 434 by link parts 435.

Figure 51:
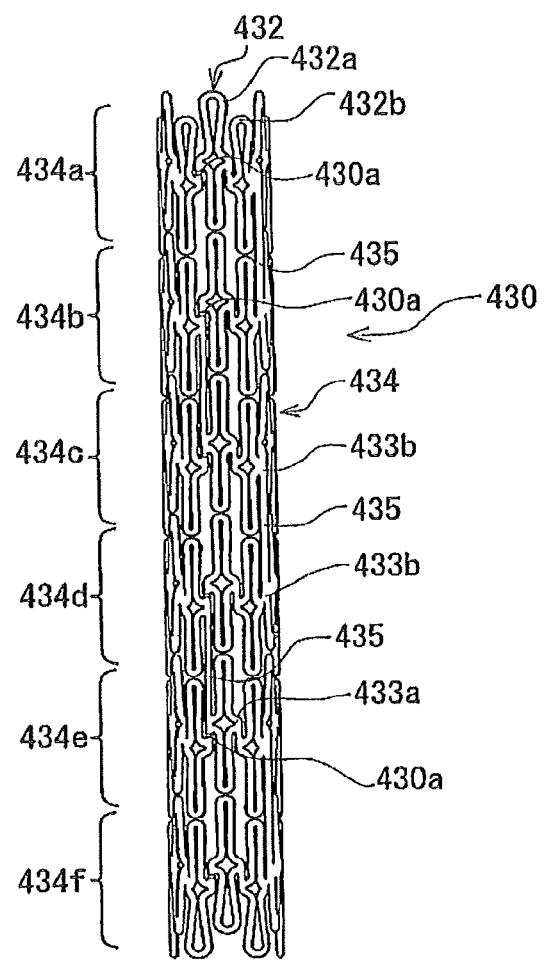
FIG. 51 is a front view of a stent according to still another disclosed embodiment.
Figure 52:
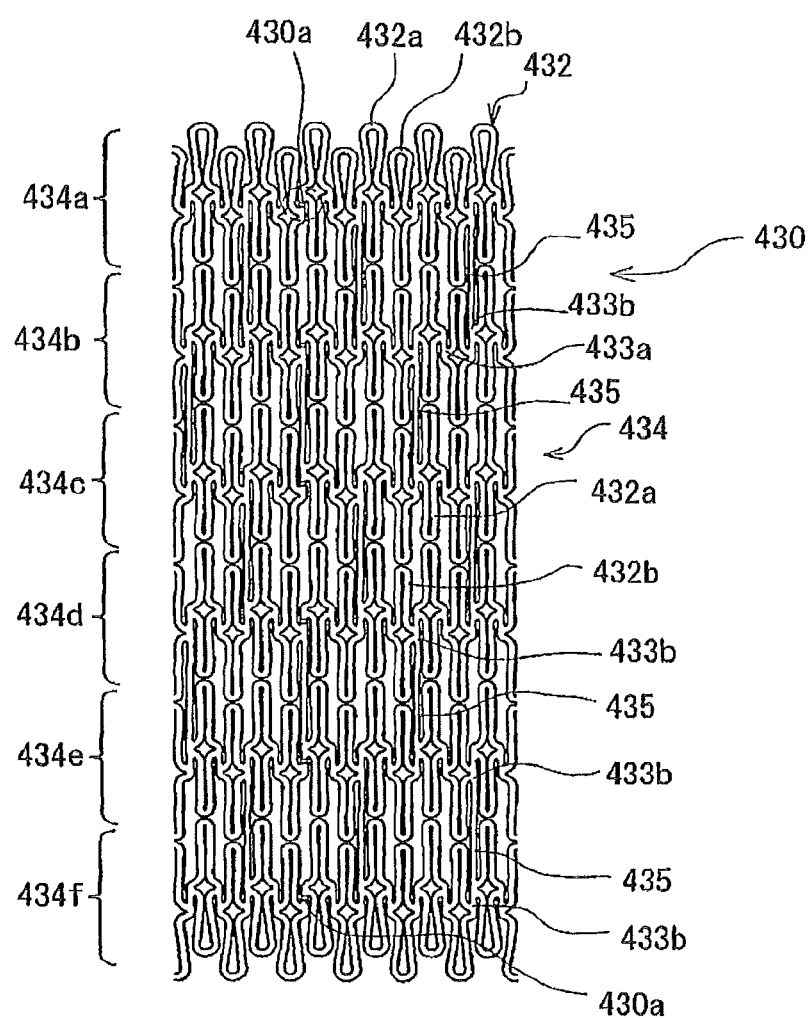
FIG. 52 is a developmental view of the stent of FIG. 51.

As shown in FIG. 51, which is a front view of the stent when the stent is compressed (in other words, when the stent is mounted onto a balloon), and FIG. 52, which is a developmental view of the stent of FIG. 51, the annular member 434 in this embodiment has twelve annular components 432 arranged at substantially equal angular intervals. The annular component 432 is elongated in the axial direction of the stent 430, has an opening inside, and is in a collapsed state in which the opening is narrowed. Each annular component 432 is so shaped as to constitute an individually independent closed system. In other words, the annular component 432 is a ring-shaped element opening in a side surface of the stent 430. With the annular components 432 thus provided with such a shape, a relatively strong dilation-maintaining force is secured. Each annular component 432 is curved along the circumferential direction of the stent 430 (annular member 434) so that the annular component as a whole is substantially equidistant from the center axis of the stent 430 (annular member 434).

The annular components in one annular member 434 are so configured that one annular component 432b of the adjacent annular components is located on the side of a proximal end (is proximally set back) in the axial direction of the stent 430 relative to the other annular component 432a. In other words, end portions of one annular member 434 are projecting in a zigzag fashion. Specifically, one annular member 434 composes a plurality of annular components 432a which have end portions projecting to the distal end side, and a plurality of annular components 432b which have end portions projecting to the proximal end side and which are each located between the annular components projecting to the distal end side (i.e., the annular components 432a project distally beyond the annular components 432b). In the stent 430 in this embodiment, each annular member 434 has an even number of the annular components. Therefore, every two adjacent components 432a and 432b are staggered in position from each other in the axial direction of the stent. For stabilizing such a zigzag shape, it is preferable to provide an even number of the annular components.

Further, in each annular member 434, the adjacent annular components 432 (432a, 432b) are interconnected by the short connection part 433 (433a, 433b) in the vicinity of the centers of side portions of the annular components. In other words, the connection parts 433 (433a, 433b) interconnect the annular components 432 (432a, 432b) in the circumferential direction of the stent, to form an annular body. The connection parts 433 substantially do not change even when the stent 430 is expanded. Therefore, the force at the time of expansion is liable to be exerted principally on the center of each of the annular components, so that the annular components can be expanded (deformed) relatively evenly. In addition, the connection parts are parts where the deformation amount at the time of compression or expansion of the stent is relatively small. As above-mentioned, the discontinuous parts 430a are provided in the connection parts.

Furthermore, in this stent 430, the connection parts 433 are substantially parallel to the center axis of the stent 430. Therefore, the length of the connection part exerts little limitation on the diameter reduction when the stent 430 is compressed, and the stent 430 can be made smaller in diameter accordingly.

The number of the annular components 432 is not limited to 12, and is preferably not less than 4. Particularly, the number of the annular components 432 is preferably 6 to 20. Moreover, the number of the annular components 432 is preferably an even number. The shape of the annular components is preferably such that the annular components become substantially elliptic or substantially rhombic when the stent is expanded. However, other polygonal shapes may also be adopted, for example, a rectangle elongated in the axial direction, a hexagon, an octagon, or the like.

The connection part 433 in the annular member 434 and the connection part 433 in the adjacent annular member 434 are interconnected by a link part 435 which is comparatively long (as compared with the connection part). Specifically, the annular member 434a and the axially adjacent annular member 434b are interconnected by the link parts 435 interconnecting the connection parts 433b, 433b. The annular member 434b and the axially adjacent annular member 434c are interconnected by the link parts 435 interconnecting the connection parts 433b, 433b. The annular member 434c and the axially adjacent annular member 434d are interconnected by the link parts 435 interconnecting the connection parts 433b, 433b. The annular member 434d and the axially adjacent annular member 434e are interconnected by the link parts 435 interconnecting the connection parts 433b, 433b. The annular member 434e and the axially adjacent annular member 434f are interconnected by the link parts 435 interconnecting the connection parts 433b, 433b. In addition, in the stent according to this embodiment, the link parts 435 are so provided as to interconnect the axially adjacent annular members 434 at a plurality of positions. The link parts may be so provided as to interconnect the adjacent annular members at only one position. The number of the link parts provided between the adjacent annular members is preferably 1 to 5, particularly 1 to 3.

In the stent 430 in this embodiment, when viewed along the axial direction thereof, the annular components 432 are so aligned that they are arrayed substantially rectilinearly in relation to the axial direction of the stent 430. Specifically, in the stent 430 in this embodiment, all the annular components adjacent to one another in the axial direction are aligned so that they are arrayed substantially rectilinearly in relation to the axial direction. In addition, all the link parts 435 are also substantially parallel to the axial direction of the stent 430. Therefore, torsion would not easily be generated at the link parts 435. Further, all the connection parts 433 are parallel to the axis of the stent 430. Therefore, torsion would not easily be generated at the connection parts 435, either.

The annular components 432a in the annular member 434 which are located on the distal end side in the axial direction of the stent 430 have end portions penetrating (axially overlapping with) the annular member adjacent to the distal end side of the annular member 434, and the annular components 432b in the annular member 434 which are located on the proximal end side in the axial direction of the stent 430 have end portions penetrating (axially overlapping with) the annular member adjacent to the proximal end side of the annular member 434. In other words, in the annular members other than those at both ends of the stent 430, projected portions (specifically, end portions of the annular components 432a) of the zigzag shape project into recessed portions (specifically, in recesses formed at the annular components 432b) of the zigzag shape of the axially adjacent annular member.

The diameter of the stent when the stent is not expanded is preferably about 0.8 to 1.8 mm, more preferably 0.9 to 1.6 mm. The length of the stent when not expanded is preferably about 8 to 40 mm. The length of one wavy-linear annular member 434 is preferably about 1.0 to 2.5 mm.

The stent disclosed here is not limited to the balloon-expandable stent as above-described, and may be a self-expandable stent.

Figure 57:
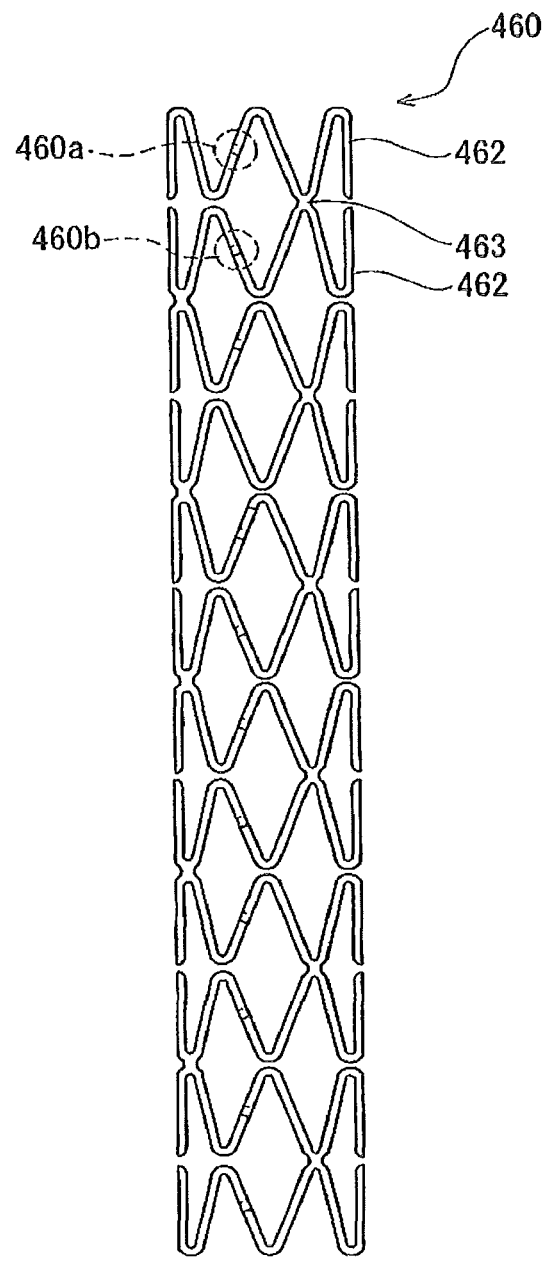
FIG. 57 is a front view of a stent according to a further disclosed embodiment.
Figure 58:
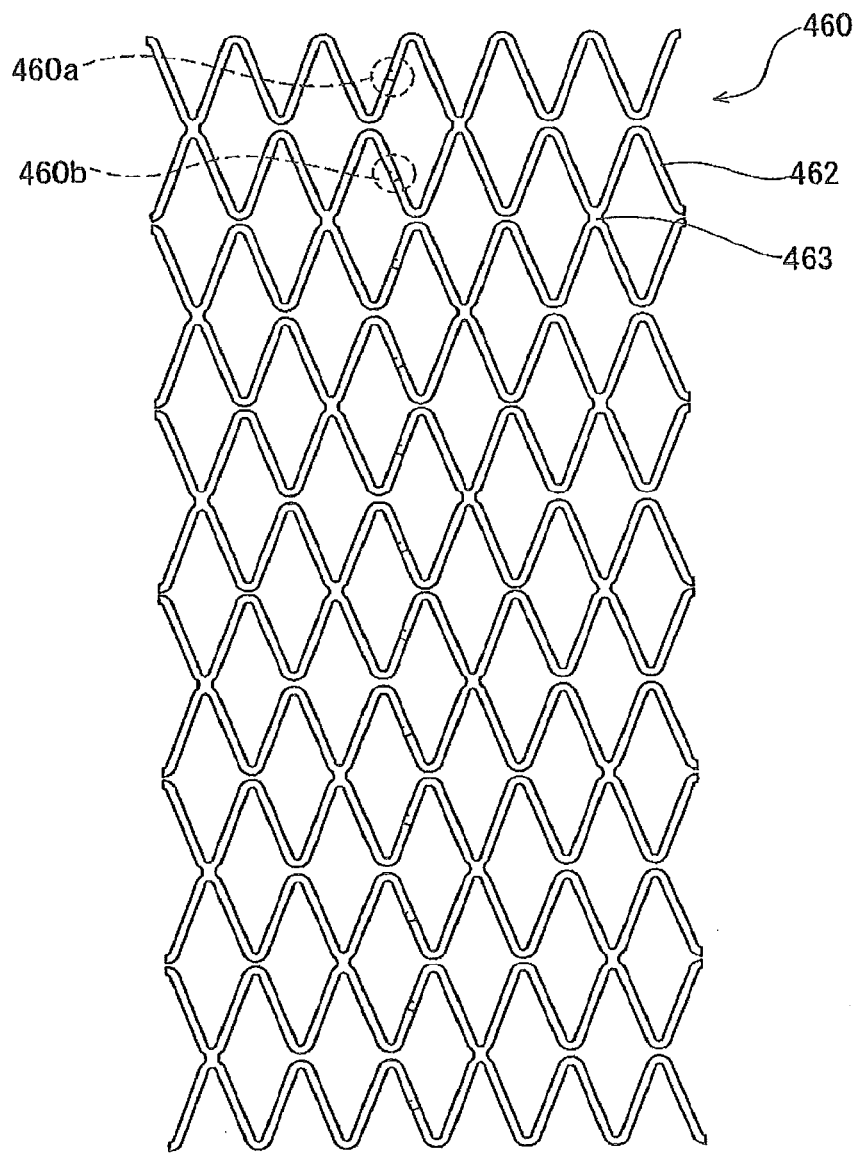
FIG. 58 is a developmental view of the stent of FIG. 57.

FIGS. 57 and 58 illustrate another embodiment of a stent disclosed here. The stent 460 in this embodiment is a stent which is formed to be a substantially tubular body, which has a diameter suitable for insertion in vivo, and which can be expanded when a force dilating radially outwards from the inside of the tubular body is exerted thereon.

The stent 460 has a configuration in which a plurality of wavy-linear annular members 462 are arrayed to be adjacent to one another along the axial direction of the stent 460 and are interconnected by connection parts 463. The number of the wavy-linear annular members 462 forming the stent 460 is 12 in the embodiment shown in FIGS. 57 and 58. The number of the wavy-linear annular members 462 differs depending on the length of the stent, and is preferably in the range of 4 to 50, particularly 10 to 35.

Each wavy-linear annular member 462 is composed of an endless linear component (specifically, a wavy-linear member) which has a plurality of one-end-side bent portions having vertices on one end side in the axial direction of the stent 460, and a plurality of the other-end-side bent portions having vertices on the other end side in the axial direction of the stent 460, and which is continuous in an annular form.

The linear component constituting each wavy-linear annular member 462 is provided with discontinuous parts 460a, 460b and a joint part joining the discontinuous part. The joint part is formed of a biodegradable material, and degradation (decomposition) of the joint part results in disconnecting the annular member 462 at the discontinuous parts 460a, 460b. As the configuration of the discontinuous parts and the joint part joining the discontinuous parts, all the above-mentioned types of configurations can be used. Particularly, it is preferable to provide means for restraining disconnection of free end portions of the linear components from the joint part.

The material constituting the self-expandable stent is preferably a superelastic metal. As the superelastic metal, the above-mentioned ones can be used.

In addition, in the stent 460 according to the above-described embodiment, the positions where the discontinuous parts and the joint parts in the annular members 462 are formed are aligned substantially rectilinearly along the axial direction of the stent 460, as shown in FIGS. 57 and 58. The positions where the discontinuous parts and the joint parts in the annular members 462 are formed are not limited to those in such a configuration as this. The positions may be set in a spiral pattern in relation to the axial direction of the stent. Further, the positions may be so set as not to have any regularity in relation to the axial direction of the stent.

Now, a blood vessel dilator according to the disclosure here will be described below with reference to an embodiment shown in FIGS. 59-61. The blood vessel dilator 100 is comprised of a tubular shaft body part 102, a foldable and dilatable balloon 103 provided at a distal portion of the shaft body part 102, and a stent 101 which is so mounted as to envelope the balloon 103 in a folded state and which is expanded by dilation of the balloon 103.

The stent 101 can take the form of any of the balloon-expandable stents according to the embodiments described above. The stent to be used here is a so-called balloon-expandable stent which has a diameter suitable for insertion into a lumen in vivo and which can be expanded when a force dilating in the radial outward direction from the inside of the tubular body is exerted thereon. The stent is preferably so configured that the area of the linear element portions of the stent in the state of being mounted on the balloon 103 accounts for 60% to 80% of the area of the outer peripheral surface, inclusive of voids, of the stent. Further, in the blood vessel dilator 100 disclosed here by way of the illustrated example, the shaft body part 102 has a balloon-dilating lumen which communicates with the inside of the balloon 103 at an end thereof. The living organ dilator 100 has a radiopaque member fixed to the outer surface of the shaft body part at a position corresponding to a central portion of the stent, or two radiopaque members fixed to the outer surface of the shaft body part at positions corresponding to both ends of a predetermined length of central portion of the stent.

Figure 60:
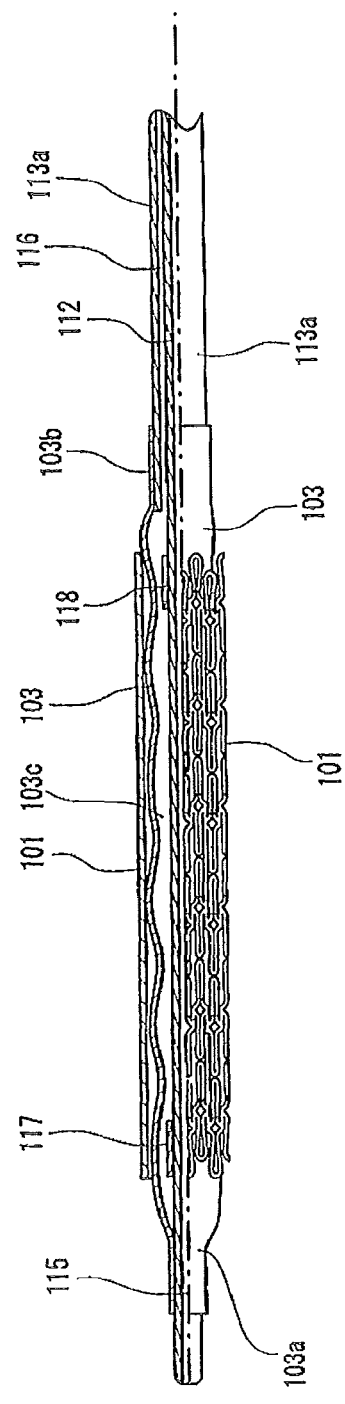
FIG. 60 is an enlarged cross-sectional view of a distal portion of the living organ dilator shown in FIG. 59.
Figure 61:
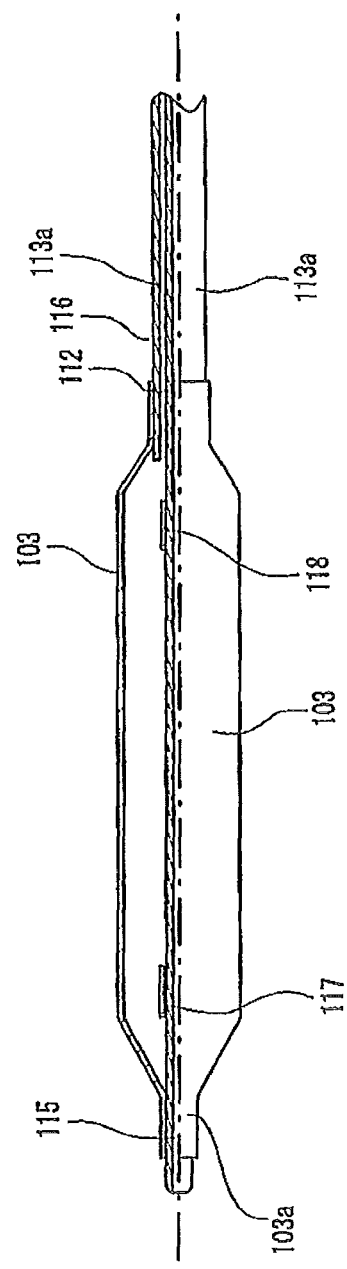
FIG. 61 is an explanatory drawing illustrating operation of the living organ dilator according to the disclosed embodiment.

In the living organ dilator 100 in this embodiment, as shown in FIG. 60, the shaft body part 102 has a guide wire lumen 115 which has one end opening at the distal end of the shaft body part 102 and has the other end opening at a proximal end portion of the shaft body part 102.

The living organ dilator 100 composes the shaft body part 102, the stent-expanding balloon 103 fixed to a distal portion of the shaft body part 102, and the stent 101 mounted onto the balloon 103. The shaft body part 102 includes an inner tube 112, an outer tube 113, and a branch hub 110.

As shown in FIG. 60, the inner tube 112 is a tube body which has the guide wire lumen 115 permitting a guide wire to be inserted therein. The inner tube 112 has a length of 100 to 2500 mm, preferably 250 to 2000 mm, an outside diameter of 0.1 to 1.0 mm, preferably 0.3 to 0.7 mm, and a material thickness of 10 to 250 µm, preferably 20 to 100 µm. The inner tube 112 is inserted or positioned in the outer tube 113, with its distal portion protruding from the outer tube 113. The outer surface of the inner tube 112 and the inner surface of the outer tube 113 define a balloon-dilating lumen 116, which has a sufficient inside volume. The outer tube 113 is a tube body which permits the inner tube 112 to be inserted or positioned therein and the distal end of which is located slightly on the proximal side relative to the distal end of the inner tube 112.

The outer tube 113 has a length of 100 to 2500 mm, preferably 250 to 2000 mm, an outside diameter of 0.5 to 1.5 mm, preferably 0.7 to 1.1 mm, and a material thickness of 25 to 200 µm, preferably 50 to 100 µm.

In the living organ dilator 100 according to this embodiment, the outer tube 113 is composed of a distal-side outer tube 113a and a body-side outer tube 113b, which are joined to each other. The distal-side outer tube 113a is reduced in diameter in a tapered manner at a portion on the distal side relative to its portion joined to the body-side outer tube 113b, and has a small diameter on the distal side relative to the tapered portion.

The outside diameter of the distal-side outer tube 113a at the small-diameter portion is 0.50 to 1.5 mm, preferably 0.60 to 1.1 mm. In addition, the outside diameter of a proximal portion of the distal-side outer tube 113a and of the body-side outer tube 113b is 0.75 to 1.5 mm, preferably 0.9 to 1.1 mm.

The balloon 103 has a distal-side joint part 103a and a proximal end side joint part 103b. The distal-side joint part 103a is fixed to the inner tube 112 at a position slightly on the proximal side relative to the distal end of the inner tube 112, while the proximal end side joint part 103b is fixed to the distal end of the outer tube. In addition, the balloon 103 communicates with the balloon-dilating lumen 116 near its proximal end.

The material(s) forming the inner tube 112 and the outer tube 113 preferably has a certain degree of flexibility. Examples of such a material include thermoplastic resins such as polyolefins (e.g., polyethylene, polypropylene, ethylene-propylene copolymer, ethylene-vinyl acetate copolymer, etc.), polyvinyl chloride, polyamide elastomer, polyurethane, etc., silicone rubber, latex rubber and the like. Among these materials, preferred are the above-mentioned thermoplastic resins, more preferably the polyolefins.

The balloon 103, as shown in FIG. 60, is foldable, and can be put into the state of being folded onto the outer periphery of the inner tube 112 when not dilated. As shown in FIG. 61, the balloon 103 has a dilatable part which is a tubular portion (preferably, a cylindrical portion) having a substantially uniform diameter so that it can expand the stent 101 mounted thereon. The substantially cylindrical portion may not necessarily be a perfect cylinder, and may be in the shape of a prism. As above-mentioned, the balloon 103 has its distal-side joint part 103a firmly attached to the inner tube 112, and its proximal end side joint part 103b firmly attached to the distal end of the outer tube 113, in a liquid-tight manner by use of an adhesive or by heat fusing or the like. Besides, in the balloon 103, the portion between the dilatable part and each joint part is formed in a tapered fashion.

The balloon 103 forms a dilation space 103c between the inner surface of the balloon 103 and the outer surface of the inner tube 112. The dilation space 103c communicates at its proximal end portion with the dilating lumen 116 over the whole circumference thereof. Since the proximal end of the balloon 103 thus communicates with the dilating lumen having a comparatively large inside volume, a dilating fluid is securely injected through the dilating lumen 116.

The material forming the balloon 103 is preferably a material having a certain degree of flexibility. Examples of the material which can be used here include thermoplastic resins such as polyolefins (e.g., polyethylene, polypropylene, ethylene-propylene copolymer, ethylene-vinyl acetate copolymer, crosslinked ethylene-vinyl acetate copolymer, etc.), polyvinyl chloride, polyamide elastomers, polyurethane, polyesters (e.g., polyethylene terephthalate), polyarylene sulfides (e.g., polyphenylene sulfide), etc., silicone rubber, latex rubber and the like. Particularly, it is preferable that the material can be oriented, and the balloon 103 is preferably a biaxially oriented one which has high strength and dilating (expanding) force.

The balloon 103 is so sized that the cylindrical portion (dilatable portion) in a dilated state has an outside diameter of 2 to 4 mm, preferably 2.5 to 3.5 mm, and a length 10 to 50 mm, preferably 20 to 40 mm. In addition, the distal-side joint part 103a has an outside diameter of 0.9 to 1.5 mm, preferably 1 to 1.3 mm, and a length of 1 to 5 mm, preferably 1 to 1.3 mm.

Besides, the proximal end side joint part 103*b* has an outside diameter of 1 to 1.6 mm, preferably 1.1 to 1.5 mm, and a length of 1 to 5 mm, preferably 2 to 4 mm.

The blood vessel dilator 100 composes two radiopaque members 117 and 118 which are fixed to the outer surface of the shaft body part at positions corresponding to both ends of the cylindrical portion (dilatable portion) in the dilated state. The two radiopaque members may be fixed to the outer surface of the shaft body part 102 (in this embodiment, the inner tube 112) at positions corresponding to both ends of a predetermined length of central portion of the stent 101. Further, a configuration may be adopted in which a single radiopaque member is fixed to the outer surface of the shaft body part at a position corresponding to a central portion of the stent.

The radiopaque members 117 and 118 are each preferably a ring-shaped member having a predetermined length or a member obtained by winding a linear material into a coil form. Examples of the material forming the radiopaque members 117, 118 include gold, platinum, tantalum, their alloys, silver-palladium alloys and the like.

The stent 101 is mounted so as to envelope the balloon 103. The stent is produced by processing a metallic pipe which has a diameter smaller than the diameter of the stent in the expanded state and has an inside diameter greater than the outside diameter of the balloon in the folded state. The balloon is inserted into the thus produced stent, and an inwardly directed uniform force is exerted on the outer surface of the stent to reduce the diameter of the stent, whereby a stent in a product state is formed. In other words, the above-mentioned stent 101 is completed upon its mounting onto the balloon by compression.

A linear rigidity-imparting element (not shown) may be inserted between the inner tube 112 and the outer tube 113 (in the balloon-dilating lumen 116). The rigidity-imparting element prevents the body part 102 of the living organ dilator 100 from kinking at its bent portion and facilitates pushing-in of the distal portion of the living organ dilator 100, without considerably lowering the flexibility of the living organ dilator 100. A distal portion of the rigidity-imparting element is preferably made smaller in diameter than the other portions, by polishing or the like method. In addition, the distal end of the small-diameter portion of the rigidity-imparting element preferably extends to the vicinity of the distal portion of the outer tube 113 of the body part. The rigidity-imparting element is preferably a metallic wire, which has a diameter of 0.05 to 1.50 mm, preferably 0.10 to 1.00 mm, and is made of an elastic metal, such as stainless steel, or a superelastic alloy or the like. Particularly preferred are a high tensile steel wire for spring and a superelastic alloy wire.

Figure 59:
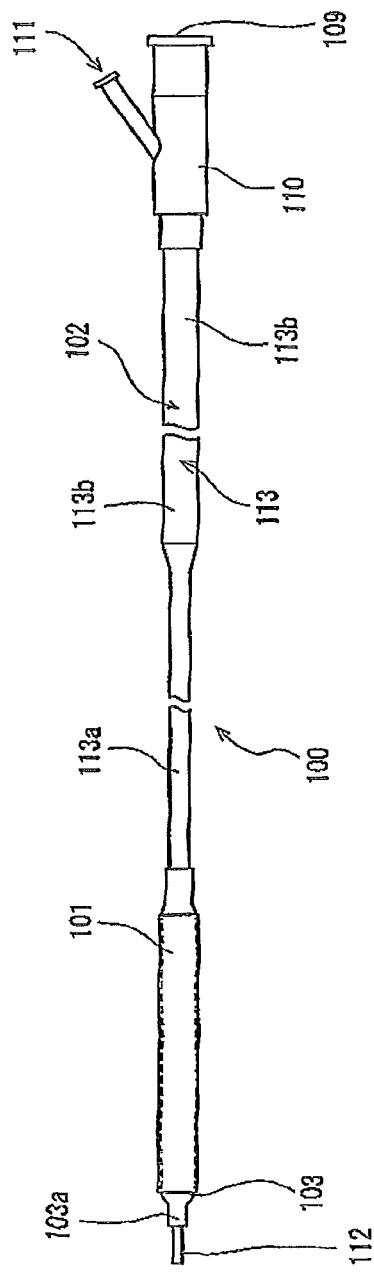
FIG. 59 is a front view of a living organ dilator according to one disclosed embodiment.

In the living organ dilator 100 in this embodiment, the branch hub 110 is fixed to the proximal end, as shown in FIG. 59. The branch hub 110 is composed of an inner tube hub which has a guide wire inlet 109 communicating with the guide wire lumen 115 and forming a guide wire port and which is secured to the inner tube 112, and an outer tube hub which has an injection port 111 communicating with the balloon-dilating lumen 116 and which is secured to the outer tube 113. In addition, the outer tube hub and the inner tube hub are secured to each other. As the material for forming the branch hub 110, thermoplastic resins such as polycarbonate, polyamides, polysulfones, polyarylates, methacrylate-butylene-styrene copolymer, etc. can be used suitably.

The structure of the living organ dilator is not limited to the above-mentioned. A structure may be adopted in which the living organ dilator is provided at its intermediate portion with a guide wire insertion port communicating with the guide wire lumen.

A blood vessel dilator according to another embodiment will be described below with reference to FIGS. 62 and 63. The living organ dilator 200 according to this embodiment is composed of a sheath 202, a stent 203 accommodated in a distal portion of the sheath 202, and an inner tube 204 which is slidably inserted in the sheath 202 and which is for pushing the stent 203 out of the distal end of the sheath 202.

As the stent 203, all the self-expandable stents according to the embodiments described above can be used. A self-expandable stent is formed in a hollow cylindrical shape, is compressed in the direction of its center axis when inserted in vivo, and, when left indwelling in vivo, can be expanded outward to restore its shape before compression.

Figure 62:
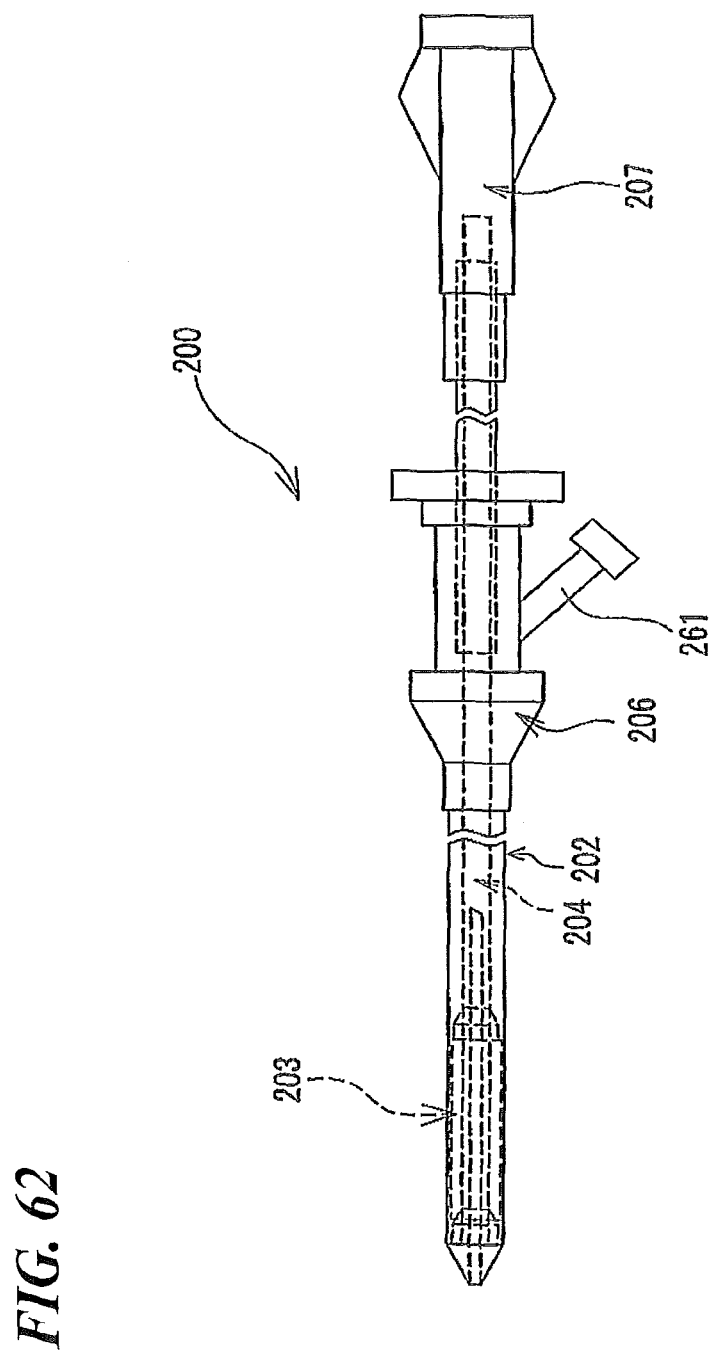
FIG. 62 is a partially omitted front view of a living organ dilator according to another disclosed embodiment.

As shown in FIG. 62, the living organ dilator 200 in this embodiment includes the sheath 202, the self-expandable stent 203, and the inner tube 204.

Figure 63:
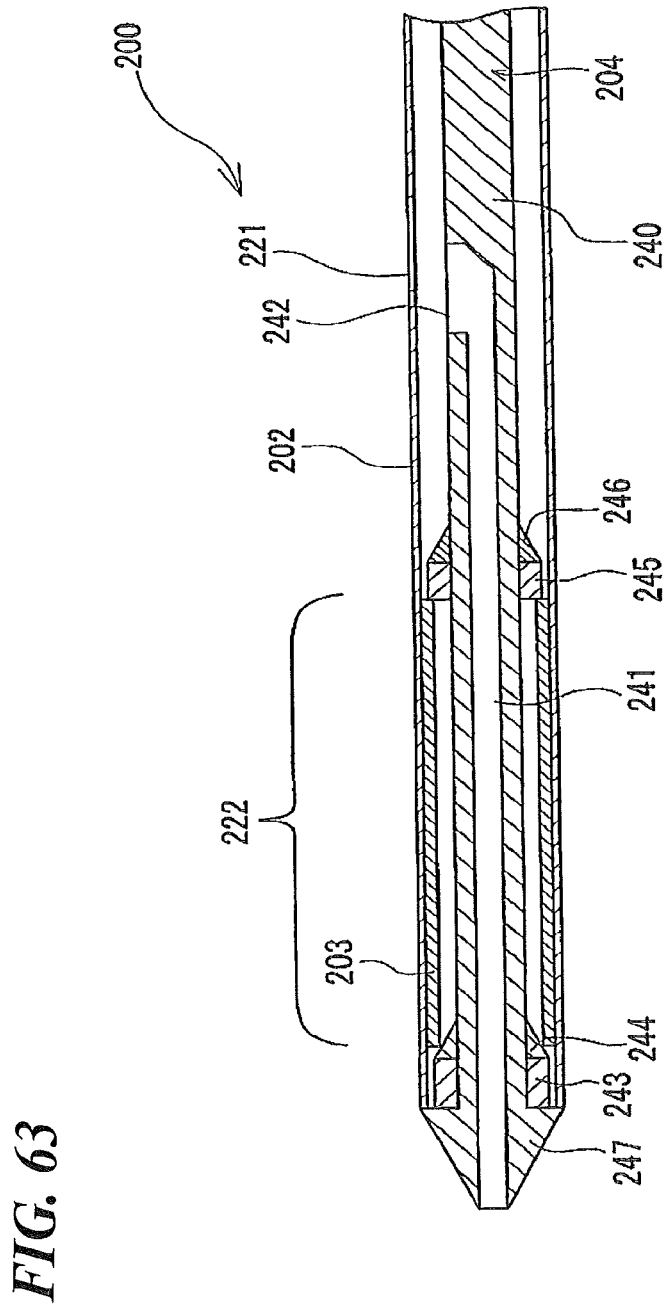
FIG. 63 is an enlarged longitudinal cross-sectional view of the vicinity of a distal portion of the living organ dilator shown in FIG. 62.

As shown in FIGS. 62 and 63, the sheath 202 is a tubular body, and is open at its distal and proximal ends. The distal opening functions as a discharge port for the stent 203 when the stent 203 is set indwelling in a stenosed lesion in a body lumen. By being pushed out via the distal opening, the stent 203 is relieved from the stress load so as to expand, thereby restoring its shape before compression. A distal portion of the sheath 202 is a stent accommodating part 222 for accommodating the stent 203 therein. In addition, the sheath 202 has a side hole 221 provided on the proximal side relative to the accommodating part 222. The side hole 221 is for leading out the guide wire to the exterior.

The outside diameter of the sheath 202 is preferably about 1.0 to 4.0 mm, particularly 1.5 to 3.0 mm. The inside diameter of the sheath 202 is preferably about 1.0 to 2.5 mm. The length of the sheath 202 is preferably 300 to 2500 mm, particularly about 300 to 2000 mm.

In addition, as shown in FIG. 62, a sheath hub 206 is fixed to a proximal portion of the sheath 202. The sheath hub 206 composes a sheath hub body, and a valve element (not shown) which is accommodated in the sheath hub body and holds the inner tube 204 in a slidable and liquid-tight manner. Besides, the sheath hub 206 has a side port 261 which is branched toward a skewly proximal side from the vicinity of the center of the sheath hub body. In addition, the sheath hub 206 preferably has an inner tube lock mechanism for restricting movement of the inner tube 204.

As shown in FIGS. 62 and 63, the inner tube 204 is composed of a shaft-shaped inner tube body part 240, a distal portion 247 which is provided at the distal end of the inner tube body part 240 and protrudes from the distal end of the sheath 202, and an inner tube hub 207 fixed to a proximal portion of the inner tube body part 240.

The distal portion 247 protrudes from the distal end of the sheath 202, and is preferably formed in a tapered manner to be gradually reduced in diameter toward the distal end, as shown in FIG. 63. This configuration facilitates insertion into a stenosed lesion. In addition, the inner tube 204 preferably has a stopper which is provided on the distal side of the stent 203 and inhibits the sheath from moving in the distal direction. The proximal end of the distal portion 247 can make contact with the distal end of the sheath 202, thereby functioning as the just-mentioned stopper.

In addition, as shown in FIG. 63, the inner tube 204 has two projected portions 243 and 245 for holding the self-expandable stent 203. The projected portions 243 and 245 are preferably annular projected portions. On the proximal side of the distal portion 247 of the inner tube 204, the projected portion 243 is provided for holding the stent. At a predetermined distance on the proximal side of the stent-holding projected portion 243, the projected portion 245 is provided for pushing out the stent. The stent 203 is disposed between these two projected portions 243 and 245. The outside diameter of the projected portions 243 and 245 are so set that the projected portions 243 and 245 can make contact with the compressed stent 203 described later. Therefore, the stent 203 is restrained by the projected portion 243 from moving toward the distal side, and is restrained by the projected portion 245 from moving toward the proximal side. Further, when the inner tube 204 is moved toward the distal side, the stent 203 is pushed by the projected portion 245 toward the distal side, to be discharged from the sheath 202. Further, as shown in FIG. 63, a tapered portion 246 gradually reduced in diameter along the proximal direction is preferably provided at the proximal side of the stent push-out projected portion 245. Similarly, as shown in FIG. 63, a tapered portion 244 gradually reduced in diameter along the proximal direction is preferably provided at the proximal side of the stent-holding projected portion 243. This configuration inhibits or prevents the projected portions from being caught on the distal end of the sheath when the inner tube 204 is again accommodated into the sheath 202 after the inner tube 204 is protruded from the distal end of the sheath 202 and the stent 203 is discharged from the sheath. The projected portions 243 and 245 may be composed of separate members formed from a radiopaque material. This helps ensure that the position of the stent can be adequately grasped under radiography, whereby the procedure is made easier.

As shown in FIG. 63, the inner tube 204 is composed of a lumen 241 which extends from the distal end thereof to at least the proximal side of the stent accommodating part 222 of the sheath 202, and an inner tube side hole 242 which communicates with the lumen 241 on the proximal side relative to the stent accommodating part. In the living organ dilator 200 in this embodiment, the lumen 241 terminates in the part where the side hole 242 is formed. The lumen 241 is provided for inserting one end of a guide wire from the distal end of the living organ dilator 200, passing the guide wire partly through the inner tube and leading out the guide wire from a side surface of the inner tube to the exterior. The inner tube side hole 242 is located slightly on the distal end side of the living organ dilator 200 relative to a sheath side hole 221. It is preferable that the center of the inner tube side hole 242 is spaced from the center of the sheath side hole 221 to the distal side by 0.5 to 10 mm.

The living organ dilator is not limited to those of the above-mentioned type. The lumen 241 may extend to the proximal end of the inner tube. In that case, the side hole 221 in the sheath is unnecessary. The inner tube 204 penetrates the sheath 202, and protrudes from the proximal opening of the sheath 202. As shown in FIG. 62, an inner tube hub 207 is secured to a proximal portion of the inner tube 204.

The stent disclosed here by way of example with reference to the illustrated and described embodiments is comprised of linear components which are deformed to exhibit a force for maintaining dilation when the stent is set indwelling in vivo. The linear components deformed when the stent is set indwelling in vivo are composed of non-biodegradable metallic linear components, and a plurality of biodegradable material-made linear components which are bonded to the non-biodegradable metallic linear components. Further, when left indwelling in vivo, the stent exhibits the force for maintaining the dilation owing to both the non-biodegradable metallic linear components and the biodegradable material-made linear components. After a predetermined period of time, biodegradation of the biodegradable material-made linear components proceeds, which results in a lowering of the dilation-maintaining force.

Therefore, when the stent is left indwelling, a sufficient force for maintaining dilation of a blood vessel is exhibited owing to the non-biodegradable metallic linear components and the biodegradable material-made linear components. Then, with the lapse of a predetermined period of time, the biodegradation of the biodegradable material-made linear components proceeds, resulting in the dilation-maintaining force being gradually lowered, the stent gradually increasing in flexibility, and its property for following up to deformation of the blood vessel being enhanced. With the biodegradable material-made linear components completely or fully biodegraded, the stent becomes composed only of the non-biodegradable metallic linear components. Consequently, the stent increases in flexibility, and its property for following up to deformation of the blood vessel is enhanced.

The stent disclosed here is a stent which is composed of linear components and which, when set indwelling in vivo, is deformed to come into close contact with a tissue in vivo. The linear components include a multiplicity of bent or curved easily deformable parts which are deformed when the stent is set indwelling in vivo, and joint parts which interjoin the easily deformable parts and are little deformed when the stent is set indwelling in vivo. The easily deformable parts are formed of an easily deformable metal, while the joint parts are formed of a biodegradable material.

Therefore, when the predetermined period of time is passed after the stent is left indwelling, the joint parts undergo biodegradation and stop contributing to maintaining the stent shape. As a result, the easily deformable parts come to be embedded in grown endothelial tissues in discrete state. Accordingly, the curing in the stent indwelling lesion can be performed again. Specifically, in the cases of performing dilation by PTCA or again performing a stent-setting procedure in the stent indwelling lesion, the stent previously left indwelling does not obstruct the curing because the stent has been split up.

Another stent according to the embodiments disclosed by way of example here has a structure in which a plurality of annular members formed in an annular form from linear components are arrayed in the axial direction of the stent, with the adjacent annular members being interconnected by a link part or parts. Each of the annular members has a discontinuous part provided in the linear component, and a joint part joining the discontinuous part. The joint part is formed of a biodegradable material, and degradation (decomposition) of the joint part results in disconnecting the annular member at the discontinuous part.

Therefore, with the lapse of a predetermined period of time after the stent is left indwelling, the joint parts undergo biodegradation, resulting in disconnecting the annular members at the discontinuous parts.

Accordingly, the curing in the stent indwelling lesion can be performed again. Specifically, in the cases of performing dilation by PTCA or again performing a stent-setting procedure in the stent indwelling lesion, the stent previously left indwelling does not obstruct the curing because the stent has been disconnected.

The detailed description above describes various aspects and embodiments of a stent and living organ dilator. However it is to be understood that the invention is not limited to the precise embodiments described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

The invention claimed is:

1. A stent configured to closely contact tissue in vivo by being deformed when set indwelling in vivo, the stent comprising:
a plurality of axially arranged annular members, with axially adjacent annular members being interconnected by at least one link part; and
a metallic wavy-linear annular member positioned at each end of the stent;
wherein said plurality of axially arranged annular members comprise a plurality of linear components configured to deform and exhibit a force for maintaining dilation when the stent is set indwelling in vivo, the linear components comprising a plurality of metallic linear components and a plurality of biodegradable material-made linear components;
wherein the at least one link part is defined by one of the metallic linear components; and
wherein, after a predetermined period of time when the stent is left indwelling in vivo and biodegradation of the biodegradable material-made linear components proceeds, the plurality of metallic linear components and the at least one link part remain intact such that a unitary metallic structure is maintained in vivo; and
wherein the metallic linear components are zigzag in shape and the biodegradable material-made linear components are zigzag in shape, the metallic linear components comprising a plurality of metallic linear spiral members extending in a spiral manner in relation to an axial direction of the stent, the plurality of metallic linear spiral members being interconnected by the biodegradable material-made linear components.

2. The stent according to claim 1, wherein the metallic linear spiral members extending in a spiral direction, the biodegradable material-made linear components each extending in a direction different from the spiral direction in which the metallic linear spiral members extend.

3. The stent according to claim 1, wherein the metallic linear components have at least one joint part which protrudes from the at least one link part in a direction of the biodegradable material-made linear components.

4. The stent according to claim 3, wherein the biodegradable material-made linear components envelop only a free end of the at least one joint part.

5. The stent according to claim 3, wherein an end portion of the biodegradable material-made liner component is joined to the at least one joint part.

6. The stent according to claim 1, wherein each annular member comprises a plurality of circumferentially arranged annular components surrounding a central axis of the stent and each elongated in an axial direction of the stent, each annular component possessing a centrally located opening and being in a collapsed form, with circumferentially adjacent annular components connected at a connection part, at least some of the connection parts connecting circumferentially adjacent annular components of a first annular member being connected by way of the link part to respective connection parts connecting circumferentially adjacent annular components of an axially adjacent second annular member, the connection parts and the link parts being composed of the metallic linear components, and at least some of the annular components each being configured such that one part of the annular component not connected to the connection part is composed of the biodegradable material-made linear component, while a remaining part is composed of the metallic linear component.

7. The stent according to claim 1, comprising means for restraining disconnection between the metallic linear component and the biodegradable material-made linear component, the means for restraining disconnection being positioned at a joint between the metallic linear component and the biodegradable material-made linear component.

8. The stent according to claim 1, wherein the biodegradable material-made linear components are connected to the metallic linear components at respective joints, the biodegradable material-made linear components covering an outer surface and/or an inner surface of the metallic linear component at the joint.

9. The stent according to claim 1, wherein the linear components deformed when the stent is set indwelling in vivo comprise a multiplicity of bent or curved more easily deformable parts which are deformed when the stent is set indwelling in vivo, and joint parts which join the more easily deformable parts and are less easily deformed when the stent is set indwelling, the more easily deformable parts being comprised of the metallic linear components, and the joint parts being comprised of the biodegradable material-made linear components.

10. The stent according to claim 9, wherein each joint part joins free ends of two respective more easily deformable parts.

11. The stent according to claim 9, wherein the joint parts and the more easily deformable parts include means for restraining disconnection of the more easily deformable parts and the respective joint parts.

12. The stent according to claim 9, wherein the joint part covers an outer surface and/or an inner surface of the more easily deformable part.

13. The stent according to claim 9, wherein the joint part covers an entire surface of the more easily deformable part.

14. The stent according to claim 1, wherein the metallic linear component is a plastically deformable metallic linear component, the stent is a tubular body possessing a diameter permitting insertion into a lumen in vivo, and the stent is expanded when a radially outwardly directed dilating force is exerted on the stent from inside the stent.

15. The stent according to claim 1, wherein the metallic linear component is a superelastic metallic linear component, the stent possesses a hollow cylindrical shape and is compressed in a direction of a center axis of the stent when inserted into a living body, and the stent expands externally to restore a pre-compression shape when left indwelling in vivo.

16. A living organ dilator comprising a tubular shaft body part, a foldable and dilatable balloon provided at a distal portion of the shaft body part, and the stent according to claim 14 which is positioned to cover the balloon in a folded state and which is expandable by expansion of the balloon.

17. A living organ dilator comprising a sheath and the stent according to claim 15 which is accommodated in a distal portion of the sheath, and an inner tube for pushing out the stent from a distal end of the sheath, the inner tube being slidably inserted in the sheath.

* * * * *